United States Patent
Connolly et al.

(10) Patent No.: US 10,125,148 B2
(45) Date of Patent: *Nov. 13, 2018

(54) PYRAZOLOPYRIMIDINE MACROCYCLES AS INHIBITORS OF HUMAN IMMUNODEFICIENCY VIRUS REPLICATION

(71) Applicant: VIIV HEALTHCARE UK (NO. 5) LIMITED, Brentford, Middlesex (GB)

(72) Inventors: Timothy P. Connolly, Wallingford, CT (US); Stanley D'Andrea, Wallingford, CT (US); John F. Kadow, Wallingford, CT (US); David R. Langley, Wallingford, CT (US); B. Narasimhulu Naidu, Wallingford, CT (US); Manoj Patel, Wallingford, CT (US); Kevin Peese, Wallingford, CT (US); Michael A. Walker, Wallingford, CT (US); Zhongyu Wang, Wallingford, CT (US); Zhizhen Barbara Zheng, Wallingford, CT (US)

(73) Assignee: ViiV HEALTHCARE UK (NO. 5) LIMITED, Brentford, Middlesex (GB)

( * ) Notice: Subject to any disclaimer, the term of this patent is extended or adjusted under 35 U.S.C. 154(b) by 62 days.

This patent is subject to a terminal disclaimer.

(21) Appl. No.: 15/119,475

(22) PCT Filed: Feb. 19, 2014

(86) PCT No.: PCT/US2014/017070
§ 371 (c)(1),
(2) Date: Aug. 17, 2016

(87) PCT Pub. No.: WO2015/126376
PCT Pub. Date: Aug. 27, 2015

(65) Prior Publication Data
US 2017/0008909 A1 Jan. 12, 2017

(51) Int. Cl.
*C07D 498/16* (2006.01)
*C07D 498/22* (2006.01)
*A61K 31/519* (2006.01)
*A61K 45/06* (2006.01)

(52) U.S. Cl.
CPC .......... *C07D 498/22* (2013.01); *A61K 31/519* (2013.01); *A61K 45/06* (2013.01); *C07D 498/16* (2013.01)

(58) Field of Classification Search
None
See application file for complete search history.

(56) References Cited

U.S. PATENT DOCUMENTS 8,906,929 B2 * 12/2014 Naidu ................. A61K 31/519
514/229.5
9,834,566 B2 * 12/2017 Kadow ................ C07D 498/16

FOREIGN PATENT DOCUMENTS

| WO | WO 2012/033735 A1 | 3/2012 |
| WO | WO 2014/028384 A1 | 2/2014 |
| WO | WO 2015/126743 A1 | 8/2015 |

* cited by examiner

*Primary Examiner* — Noble E Jarrell
(74) *Attorney, Agent, or Firm* — Robert H. Brink; Edward R. Gimmi; William R. Majarian

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

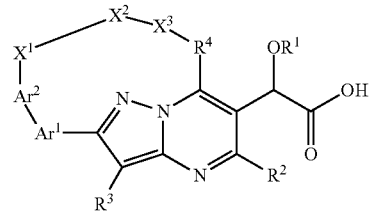

4 Claims, No Drawings

PYRAZOLOPYRIMIDINE MACROCYCLES AS INHIBITORS OF HUMAN IMMUNODEFICIENCY VIRUS REPLICATION

This application is a 371 of International Application No. PCT/US2014/017070, filed 19 Feb. 2014, which is incorporated herein in its entirety.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 35.3 million people worldwide are infected with the virus (UNAIDS Report on the Global AIDS Epidemic 2013). In addition to the large number of individuals already infected, the virus continues to spread. Estimates from 2012 point to close to 2.3 million new infections in that year alone. In the same year there were approximately 1.6 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130034, WO2010130842, WO2011015641, WO2011076765, WO2012003497, WO2012003498, WO2012033735, WO2012065963 and WO2012066442.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

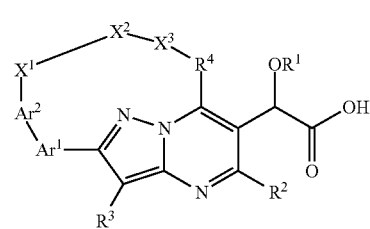

where:
R$^1$ is hydrogen, alkyl, or cycloalkyl;
R$^2$ is hydrogen or alkyl;
R$^3$ is hydrogen, alkyl or halo;
R$^4$ is cycloalkyl or Ar$^3$;
or R$^4$ is azetidinyl, pyrrolidinyl, piperidinyl, piperazinyl, morpholinyl, homopiperidinyl, homopiperazinyl, or homomorpholinyl, and is substituted with 0-3 alkyl substituents;
R$^5$ is hydrogen or alkyl;
Ar$^1$ is phenyl substituted with 0-3 substituents selected from cyano, halo, alkyl, haloalkyl, alkoxy, and haloalkoxy;
Ar$^2$ is phenyl, pyridinyl, pyridazinyl, pyrimidinyl, pyrazinyl, or trizainyl, and is substituted with 0-3 substituents selected from cyano, halo, alkyl, haloalkyl, alkoxy, haloalkoxy, and CON(R$^5$)$_2$;
Ar$^3$ is phenyl, chromanyl, or dihydrobenzoxazinyl, and is substituted with 0-3 substituents selected from cyano, halo, alkyl, haloalkyl, alkoxy, and haloalkoxy;
X$^1$ is CH, CH$_2$, O, S, or NR$^5$;
X$^2$ is alkylene or alkenylene; and
X$^3$ is CH, CH$_2$, CH$_2$O, O, S, or NR$^5$;
or a pharmaceutically acceptable salt thereof.

Another aspect of the invention is a compound of Formula I where:

$R^1$ is hydrogen or alkyl;
$R^2$ is hydrogen or alkyl;
$R^3$ is hydrogen, alkyl or halo;
$R^4$ is cycloalkyl or $Ar^3$;
or $R^4$ is azetidinyl, pyrrolidinyl, piperidinyl, piperazinyl, morpholinyl, homopiperidinyl, homopiperazinyl, or homomorpholinyl, and is substituted with 0-3 alkyl substituents;
$R^5$ is hydrogen or alkyl;
$Ar^1$ is phenyl substituted with 0-3 substituents selected from cyano, halo, alkyl, haloalkyl, alkoxy, and haloalkoxy;
$Ar^2$ is phenyl, pyridinyl, pyridazinyl, pyrimidinyl, pyrazinyl, or trizainyl, and is substituted with 0-3 substituents selected from cyano, halo, alkyl, haloalkyl, alkoxy, and haloalkoxy;
$Ar^3$ is phenyl, chromanyl, or dihydrobenzoxazinyl, and is substituted with 0-3 substituents selected from cyano, halo, alkyl, haloalkyl, alkoxy, and haloalkoxy;
$X^1$ is $CH_2$, O, S, or $NR^5$;
$X^2$ is alkylene or alkenylene; and
$X^3$ is CH, $CH_2$, O, S, or $NR^5$;
or a pharmaceutically acceptable salt thereof.

Another aspect of the invention is a compound of Formula I where $R^1$ is alkyl; $R^2$ is alkyl; $R^3$ is hydrogen; $R^4$ is $Ar^3$ or is azetidinyl, pyrrolidinyl, piperidinyl, piperazinyl, morpholinyl, homopiperidinyl, homopiperazinyl, or homomorpholinyl substituted with 0-3 alkyl substituents; $Ar^1$ is phenyl substituted with 0-3 substituents selected from cyano, halo, alkyl, haloalkyl, alkoxy, and haloalkoxy; $Ar^2$ is phenyl substituted with 0-3 substituents selected from cyano, halo, alkyl, haloalkyl, alkoxy, and haloalkoxy; $Ar^3$ is dihydrobenzoxazinyl substituted with 0-3 substituents selected from cyano, halo, alkyl, haloalkyl, alkoxy, and haloalkoxy; $X^1$ is $CH_2$ or O; $X^2$ is alkylene or alkenylene; and $X^3$ is CH, $CH_2$ or O; or a pharmaceutically acceptable salt thereof.

Another aspect of the invention is a compound of Formula I where $R^1$ is alkyl; $R^2$ is alkyl; $R^3$ is hydrogen; $R^4$ is $Ar^3$ or is piperidinyl substituted with 0-1 alkyl substituents; $Ar^1$ is phenyl; $Ar^2$ is phenyl; $Ar^3$ is dihydrobenzoxazinyl substituted with 0-1 halo or alkyl substituents; $X^1$ is $CH_2$ or O; $X^2$ is alkylene or alkenylene; and $X^3$ is CH, $CH_2$ or O; or a pharmaceutically acceptable salt thereof.

Another aspect of the invention is a compound of formula I where $R^1$ is alkyl; $R^2$ is alkyl; $R^3$ is hydrogen; $R^4$ is $Ar^3$ or is piperidinyl substituted with 0-1 alkyl substituents; $Ar^1$ is phenyl; $Ar^2$ is phenyl substituted with 0-3 substituents selected from cyano, halo, alkyl, haloalkyl, alkoxy, haloalkoxy, and $CON(R^5)_2$; $Ar^3$ is dihydrobenzoxazinyl substituted with 0-1 halo or alkyl substituents; $X^1$ is $CH_2$ or O; $X^2$ is alkylene or alkenylene; and $X^3$ is CH, $CH_2$ or O; or a pharmaceutically acceptable salt thereof.

Another aspect of the invention is a compound of Formula I where $R^1$ is alkyl, $R^2$ is alkyl and $R^3$ is hydrogen.

Another aspect of the invention is a compound of Formula I where $R^4$ is $Ar^3$ or is azetidinyl, pyrrolidinyl, piperidinyl, piperazinyl, morpholinyl, homopiperidinyl, homopiperazinyl, or homomorpholinyl substituted with 0-3 alkyl substituents.

Another aspect of the invention is a compound of Formula I where $R^4$ is $Ar^3$.

Another aspect of the invention is a compound of Formula I where $R^4$ is azetidinyl, pyrrolidinyl, piperidinyl, piperazinyl, morpholinyl, homopiperidinyl, homopiperazinyl, or homomorpholinyl substituted with 0-3 alkyl substituents.

Another aspect of the invention is a compound of Formula I where $R^4$ is piperidinyl substituted with 0-3 alkyl substituents.

Another aspect of the invention is a compound of Formula I where $Ar^1$ is phenyl substituted with 0-3 substituents selected from cyano, halo, alkyl, haloalkyl, alkoxy, and haloalkoxy.

Another aspect of the invention is a compound of Formula I where $Ar^1$ is phenyl.

Another aspect of the invention is a compound of Formula I where $Ar^2$ is phenyl substituted with 0-3 substituents selected from cyano, halo, alkyl, haloalkyl, alkoxy, haloalkoxy, and $CON(R^5)_2$.

Another aspect of the invention is a compound of Formula I where $Ar^2$ is pyridinyl, pyridazinyl, pyrimidinyl, pyrazinyl, or trizainyl, and is substituted with 0-3 substituents selected from cyano, halo, alkyl, haloalkyl, alkoxy, haloalkoxy, and $CON(R^5)_2$.

Another aspect of the invention is a compound of Formula I where $Ar^3$ is phenyl, chromanyl, or dihydrobenzoxazinyl, and is substituted with 0-3 substituents selected from cyano, halo, alkyl, haloalkyl, alkoxy, and haloalkoxy.

Another aspect of the invention is a compound of Formula I where $Ar^3$ is phenyl substituted with 0-3 substituents selected from cyano, halo, alkyl, haloalkyl, alkoxy, and haloalkoxy.

Another aspect of the invention is a compound of Formula I where $X^1$ is $CH_2$ or O; $X^2$ is alkylene or alkenylene; and $X^3$ is CH, $CH_2$ or O.

Unless specified otherwise, these terms have the following meanings "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Alkyleneoxy" means a straight or branched divalent alkyloxy group composed of 1 to 6 carbons, for example, —$CH_2CH_2CH_2O$—. "Alkenyleneoxy" means a straight or branched divalent alkeneoxy group composed of 2 to 6 carbons with at least one double bond, for example, —CH=$CHCH_2O$—. "Halo" includes fluoro, chloro, bromo, and iodo. "Halo" includes all halogenated isomers from monohalo substituted to perhalo substituted in substituents defined with halo, for example, "Haloalkyl" "haloalkoxy", "halophenyl", and "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents.

Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV replication. A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv in 293T cells using the LipofectAMINE PLUS kit from Invitrogen (Carlsbad, Calif.) according to the manufacturer, and the pseudotype virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. This provides a simple and easy method for quantitating the extent of virus growth and consequently, the antiviral activity of test compounds. Luciferase was quantitated using the Dual Luciferase kit from Promega (Madison, Wis.).

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under two serum conditions, 10% FBS, or 45 mg/ml human serum albumin/10% FBS, and the results from at least 2 experiments were used to calculate the $EC_{50}$ values. The anti-viral activity shown in Table 1 was determined in 10% FBS.

TABLE 1

| Example | $EC_{50}$ μM |
|---|---|
| 1 | 0.039 |
| 2 | 0.026 |
| 3 | 0.026 |
| 4 | 0.023 |
| 5 | 0.022 |
| 6 | 0.031 |
| 7 | 0.029 |
| 8 | 0.005 |
| 9 | 0.006 |
| 10 | 0.011 |
| 11 | 0.003 |
| 12 | 0.003 |
| 13 | 0.004 |
| 14 | 0.009 |
| 15 | 0.008 |
| 16 | 0.008 |
| 17 | 0.009 |
| 18 | 0.007 |
| 19 | 0.033 |
| 20 | 0.133 |
| 21 | 0.150 |
| 22 | 0.013 |
| 23 | 0.024 |
| 24 | 0.004 |
| 25 | 0.004 |
| 26 | 0.049 |
| 27 | 0.045 |
| 28 | 0.027 | n.d. = not determined

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCM" for dichloromethane, "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "DEAD" for diethyl azodicarboxylate and "DIAD" for diisopropyl azodicarboxylate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compound I-1 and I-2 are commercially available or synthesized by reactions known in the art. Intermediates I-3 can be prepared by procedure known in the art or as set forth in the examples below using compound I-1 and compound I-2. Intermediates I-3 can be transformed to intermediates I-5 via intermediates I-4 using conditions known to those skilled in the art. Intermediates I-5 can be oxidized to intermediates I-6 by reactions known in the art, including Davis oxidation. Intermediates I-6 can be oxidized to intermediates I-7 by known conditions, including Dess-Martin oxidation. Intermediates I-7 can be reduced to chiral intermediates I-8 using known conditions in the presence of catalytic chiral ligands. Intermediates I-8 can be converted to the intermediates I-9 by known conditions, including tertiary-butyl acetate and perchloric acid. Sequential coupling of aryl groups to Intermediates I-9 using conditions known in the art, including Suzuki coupling, can provide intermediates 10 and 11. Boronate or boronic acid coupling reagents are commercially available or are prepared by reactions known in the art (for example, PCT Appln. WO20090662285). Intermediates I-11 can be converted to intermediates I-12 by conditions known in the art, including ring closing metathesis. Hydrolysis of intermediates I-12 can provide products I-13 which can be converted to I-14 using conditions known in the art.

Scheme I

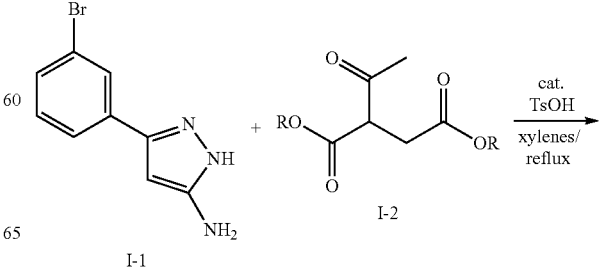

11
-continued
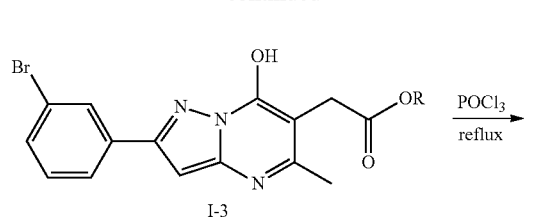
I-3
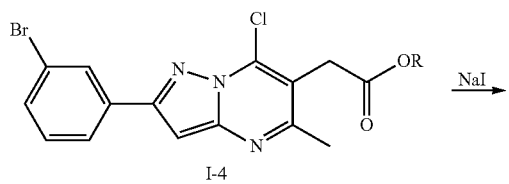
I-4
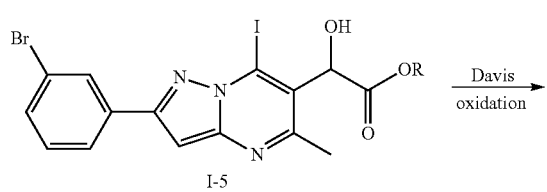
I-5
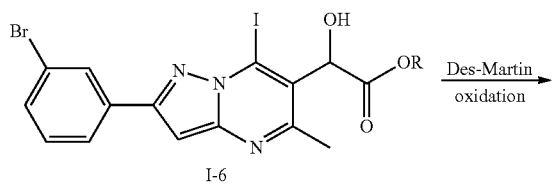
I-6
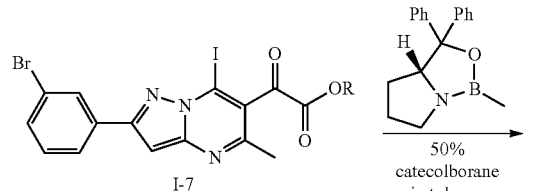
I-7
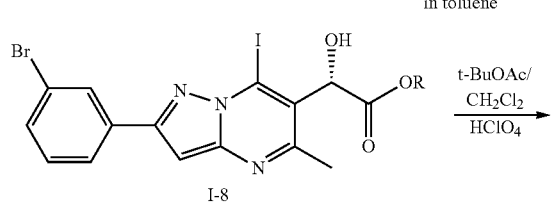
I-8
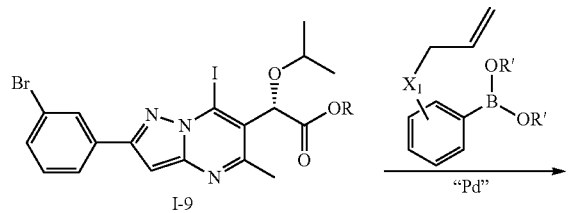
I-9
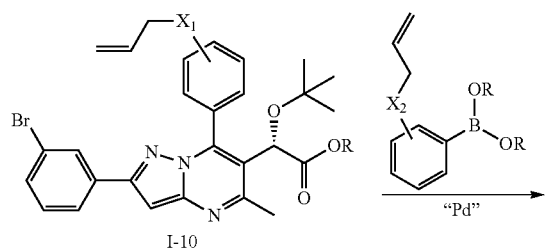
I-10
12
-continued
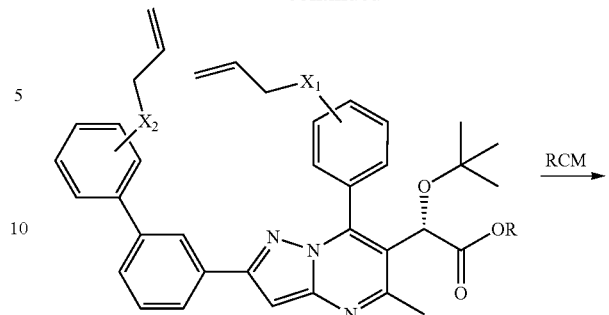
I-11
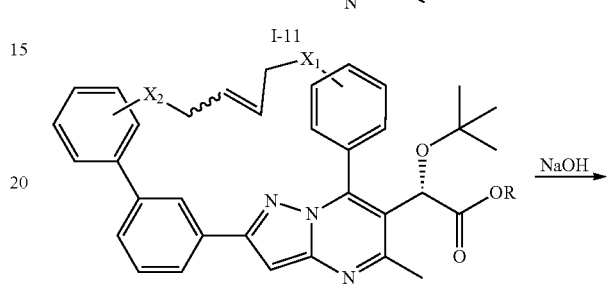
I-12
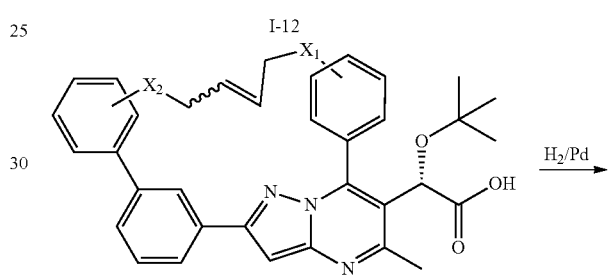
I-13
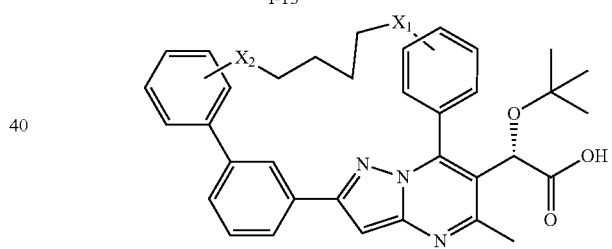
Intermediate I-4 can be transformed to final compounds II-5 and II-6 by methods known in the art as outlined in Scheme II.
Scheme II
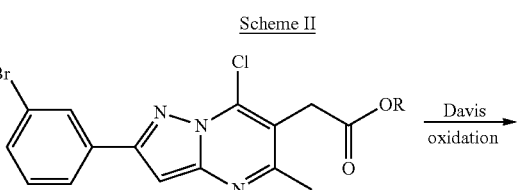
I-4
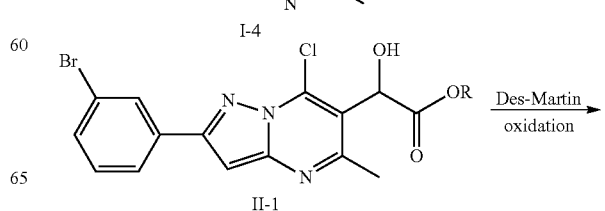
II-1

13
-continued
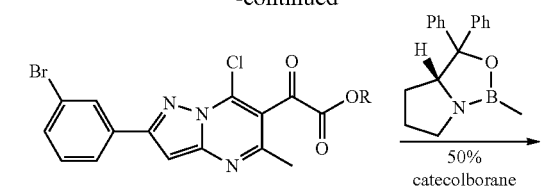
II-2
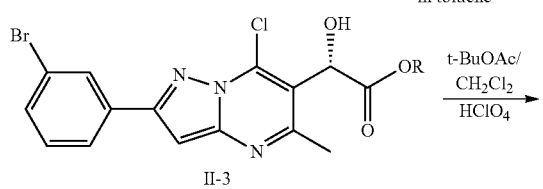
II-3
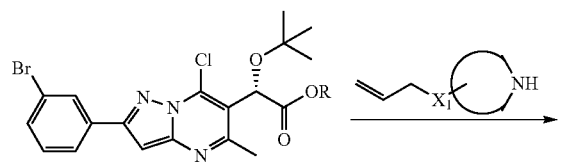
II-4
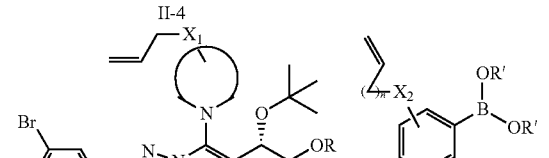
II-5
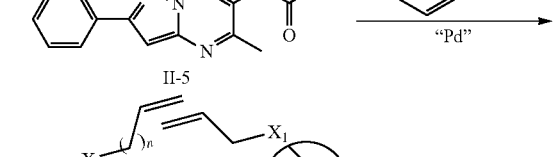
II-6
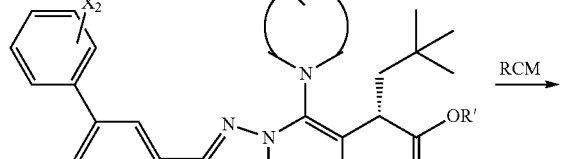
II-7
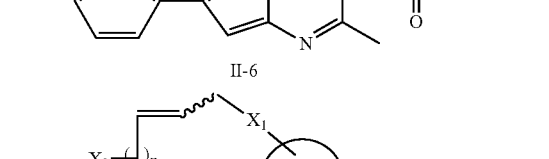
II-8
14
-continued
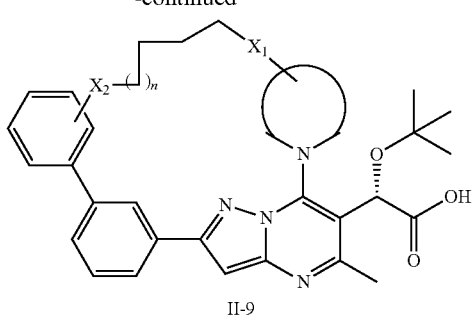
II-9
Intermediates II-5 can be transformed to final compounds III-4 and III-6 by methods known in the art as outlined in Scheme III.
Scheme III
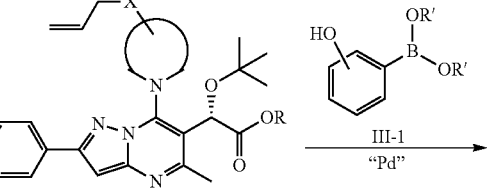
II-5
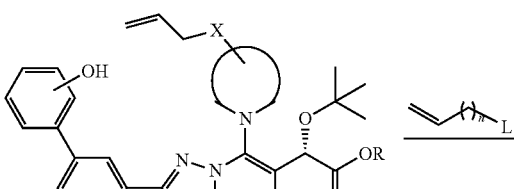
III-1
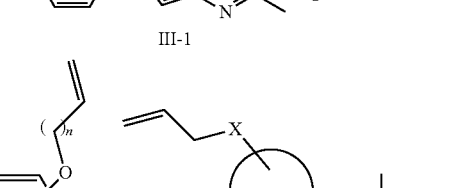
III-2
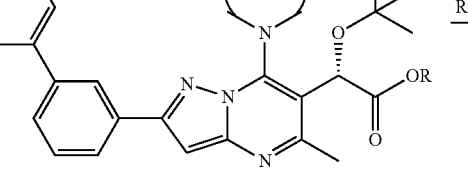
III-3

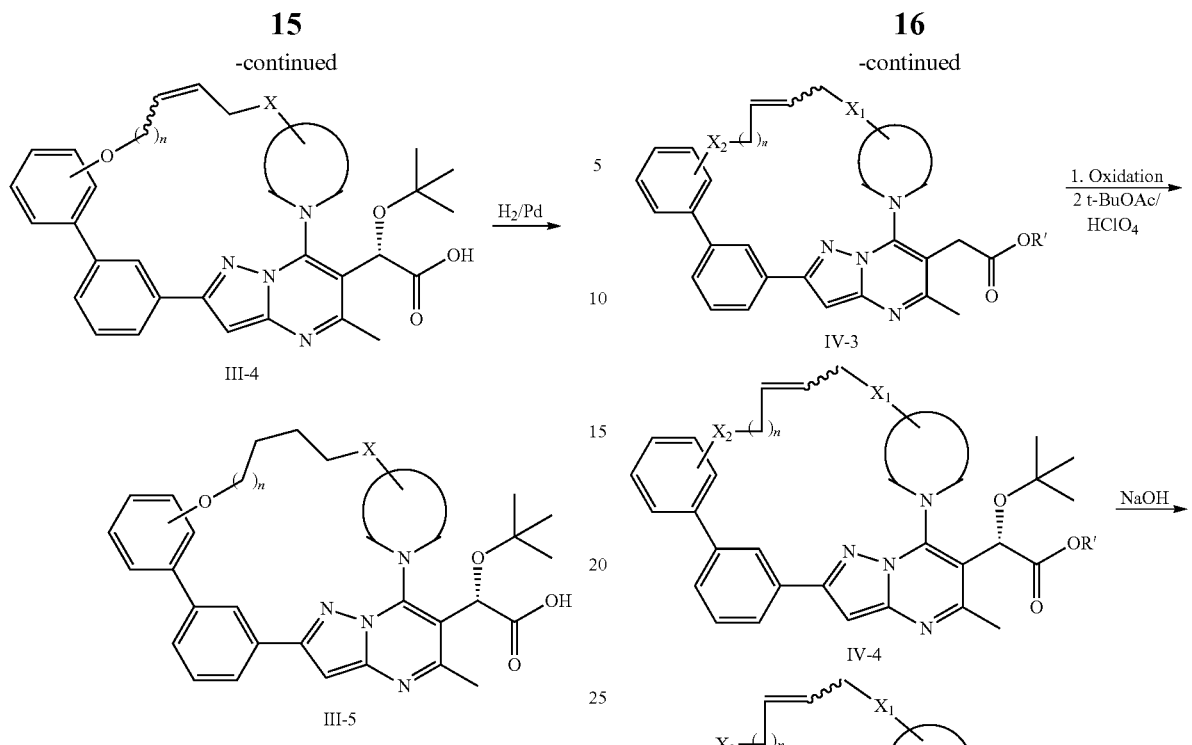
Intermediates I-4 can be transformed to final compounds IV-5 and IV-6 by methods known in the art as outlined in Scheme IV.
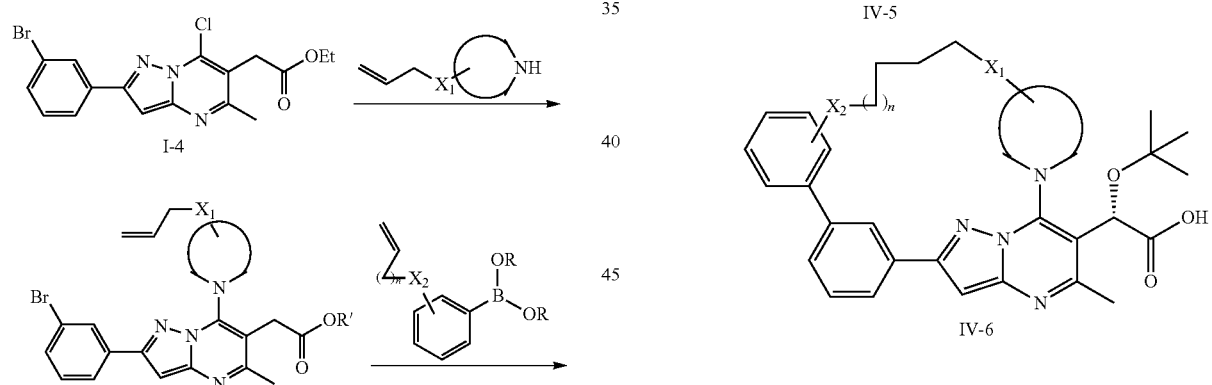
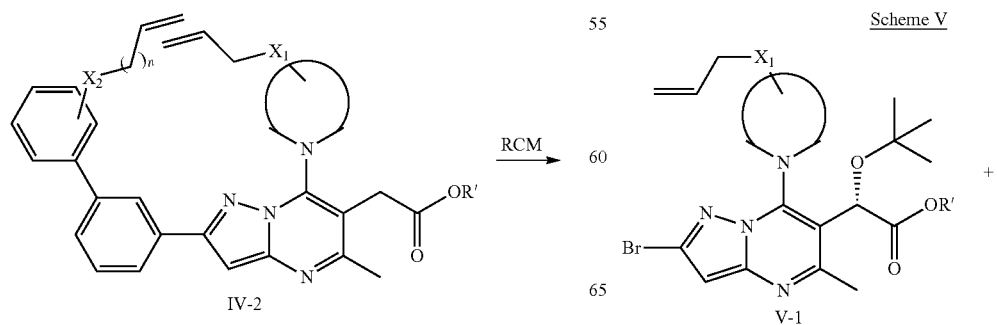
Intermediates V-1 can be transformed to final compounds V-4 and V-5 by methods known in the art as outlined in Scheme V.

-continued

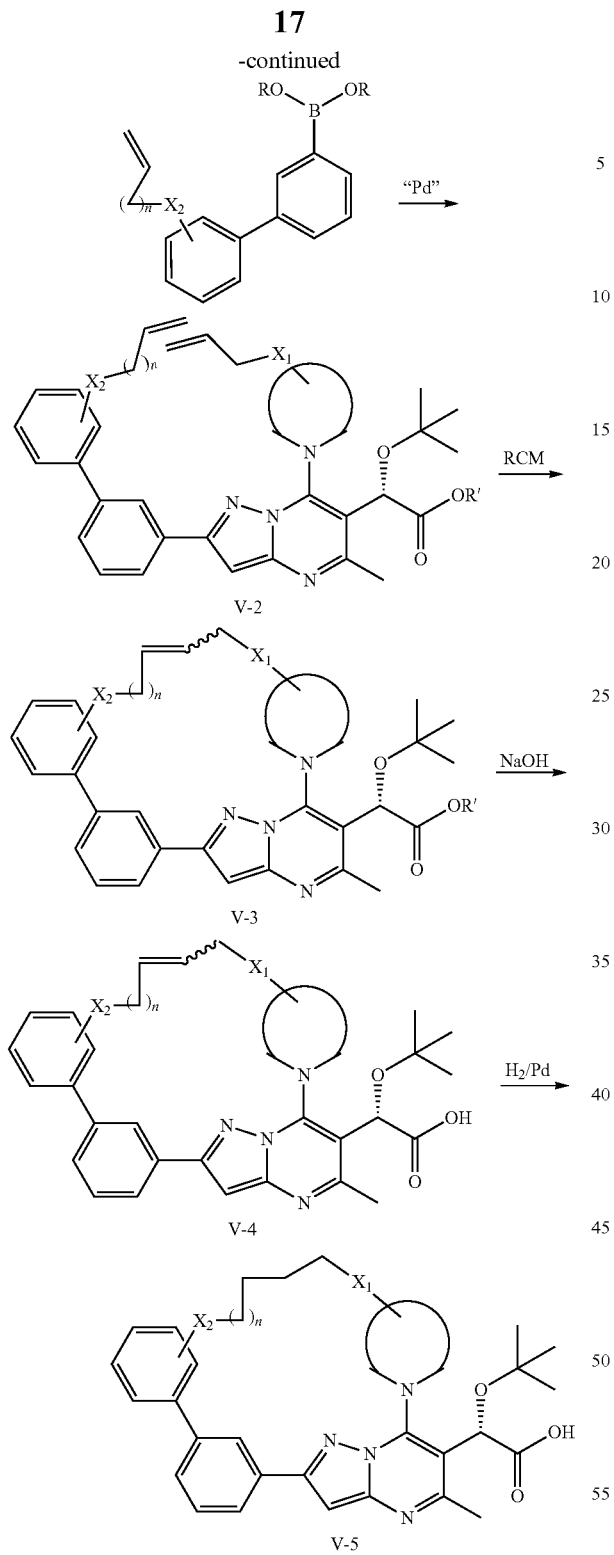

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 μm) using either mobile phase A: 9:1 H$_2$O/acetonitrile with 10 mM NH$_4$OAc and mobile phase B: A: 9:1 acetonitrile/H$_2$O with: 10 mM NH$_4$OAc or mobile phase A: 95:5 H$_2$O/MeOH with 20 mM NH$_4$OAc and mobile phase B: 95:5 MeOH/H$_2$O with 20 mM NH$_4$OAc.

INTERMEDIATE 1

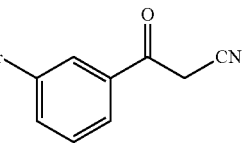

3-(3-bromophenyl)-3-oxopropanenitrile

Acetonitrile (21.86 mL, 419 mmol) was added to a stirred suspension of 60% NaH (7.25 g, 181 mmol) in THF (150 mL). Then, methyl 3-bromobenzoate (30 g, 140 mmol) was added and the mixture was heated at 75° C. for 4 h. After cooling to room temperature, water followed by 1N HCl (200 mL) was added and the mixture was extracted with ethyl acetate (500 mL), washed with sat. NaHCO$_3$ solution (200 mL), dried (Na$_2$SO$_4$), filtered and concentrated to afford 3-(3-bromophenyl)-3-oxopropanenitrile (29 g, 129 mmol, 93% yield) as light yellow solid. $^1$H NMR (500 MHz, CDCl$_3$) δ 8.09 (t, J=1.7 Hz, 1H), 7.90-7.86 (m, 1H), 7.83 (ddd, J=8.0, 2.0, 1.1 Hz, 1H), 7.45 (t, J=7.9 Hz, 1H), 4.08 (s, 2H).

INTERMEDIATE 2

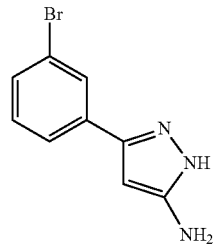 [SMILES: Nc1cc(-c2cccc(Br)c2)n[nH]1]

3-(3-bromophenyl)-1H-pyrazol-5-amine

A mixture of 3-(3-bromophenyl)-3-oxopropanenitrile (35 g, 156 mmol) and hydrazine hydrate (11.34 mL, 234 mmol) in ethanol (600 mL) was refluxed for 16 h. Mixture was then cooled and concentrated in vacuo. Crude product was diluted with dichloromethane and stirred for 5 min. Solids were filtered and dried to afford 3-(3-bromophenyl)-1H-pyrazol-5-amine (30 g, 126 mmol, 81% yield) as off-white solid. $^1$H NMR (400 MHz, DMSO-d$_6$) δ 12.02 (br. s., 0.4H), 11.66 (br. s., 0.6H), 7.86 (t, J=1.6 Hz, 1H), 7.67 (d, J=7.5 Hz, 1H), 7.45 (d, J=6.8 Hz, 1H), 7.37-7.18 (m, 1H), 5.78 (br. s., 1H), 5.08 (br. s., 1.2H), 4.68 (br. s., 0.8H). LCMS (M+H)=240.1.

INTERMEDIATE 3

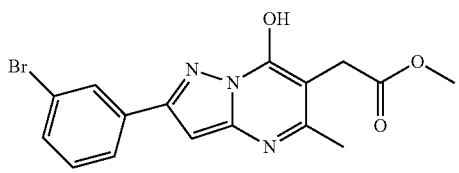

Methyl 2-(2-(3-bromophenyl)-7-hydroxy-5-methyl-pyrazolo[1,5-a]pyrimidin-6-yl)acetate A 3-lit three neck flask was fitted with a mechanical stirrer and a heating mantle. A suspension of 3-(3-bromophenyl)-1H-pyrazol-5-amine (84.9 g, 357 mmol), dimethyl 2-acetylsuccinate (73.8 g, 392 mmol) and tosic acid monohydrate (1.357 g, 7.13 mmol) in o-xylene (1500 mL) was heated to refluxed (135° C. measured internal temp) for 3.5 h. The heating was turned off, the reaction was diluted with hexanes (1000 mL) and was allowed to cool slowly overnight. The solids were collected by filtration. The filter cake was washed with hexanes and dried under vacuum overnight to afford methyl 2-(2-(3-bromophenyl)-7-hydroxy-5-methyl-pyrazolo[1,5-a]pyrimidin-6-yl)acetate (132.21 g, 334 mmol, 94% yield) as a white powdery solid. $^1$H NMR (500 MHz, DMSO-$d_6$) δ: 12.47 (s, 1H), 8.18 (t, J=1.7 Hz, 1H), 8.02 (dt, J=7.1, 1.3 Hz, 1H), 7.65-7.60 (m, 1H), 7.45 (t, J=7.9 Hz, 1H), 6.69 (s, 1H), 3.63 (s, 3H), 3.58 (s, 2H), 2.34 (s, 3H). LCMS (M+H)=376.4.

INTERMEDIATE 4

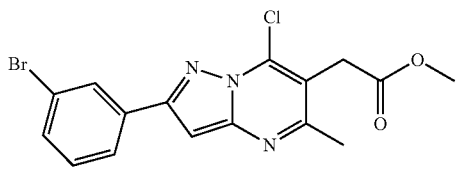 [SMILES: COC(=O)Cc1c(C)nc2cc(-c3cccc(Br)c3)nn2c1Cl]

2-(2-(3-Bromophenyl)-7-chloro-5-methylpyrazolo[1,5-a]pyrimidin-6-yl)acetate

A mixture of methyl 2-(2-(3-bromophenyl)-7-hydroxy-5-methylpyrazolo[1,5-a]pyrimidin-6-yl)acetate (133 g, 354 mmol) and N,N-dimethylaniline (62.7 ml, 495 mmol) in POCl$_3$ (450 ml) was heated (120° C. oil bath) for 2.5 h. The reaction was cooled, then concentrated under reduced pressure. The residue was dried from toluene (3×300 mL), and the residue, suspended in EtOAc (600 mL) was poured onto ice water at a rate that maintained the cold temperature. The emulsion was then diluted (EtOAc, 300 mL) and the combined layers were pulled through a filter paper to collect solids. The solids were washed with several portions of EtOAc, then air dried. The filtered solids were suspended in EtOAc and hexanes (500 ml, of each) and stirred for 10 min, then filtered. The filter cake was washed with hexanes and dried under vacuum to afford methyl 2-(2-(3-bromophenyl)-7-chloro-5-methylpyrazolo[1,5-a]pyrimidin-6-yl)acetate (121.7 g, 300 mmol, 85% yield) as pale green solid. $^1$H NMR (500 MHz, DMSO-$d_6$) δ: 8.25 (t, J=1.8 Hz, 1H), 8.09 (dt, J=7.8, 1.3 Hz, 1H), 7.63-7.70 (m, 1H), 7.45-7.54 (m, 1H), 7.40 (s, 1H), 4.04 (s, 2H), 3.71 (s, 3H), 2.58 (s, 3H). LC/MS (085-04, M+H)=396.1.

INTERMEDIATE 5

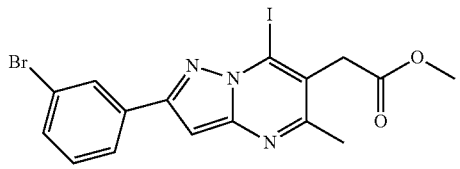 [SMILES: COC(=O)Cc1c(C)nc2cc(-c3cccc(Br)c3)nn2c1I]

Methyl 2-(2-(3-bromophenyl)-7-iodo-5-methylpyrazolo[1,5-a]pyrimidin-6-yl)acetate Methyl 2-(2-(3-bromophenyl)-7-chloro-5-methylpyrazolo[1,5-a]pyrimidin-6-yl)acetate (1 g, 2.53 mmol) and NaI (1.519 g, 10.14 mmol) were suspended in acetonitrile (10 mL) and the resulting mixture was heated at 80° C. for 5 h. After cooling to room temp, mixture was diluted with ethyl acetate (50 mL) and washed with water (25 mL) and aqueous Na$_2$S$_2$O$_3$ (25 mL), dried (Na$_2$SO$_4$), filtered and concentrated. Crude was then triturated with ethyl acetate/hexane to afford methyl 2-(2-(3-bromophenyl)-7-iodo-5-methylpyrazolo[1,5-a]pyrimidin-6-yl)acetate (1 g, 2.057 mmol, 81% yield) as off white solid. $^1$H NMR (400 MHz, CDCl$_3$) δ: 8.20 (t, J=1.8 Hz, 1H), 7.95 (dt, J=7.8, 1.3 Hz, 1H), 7.55 (ddd, J=8.0, 2.0, 1.0 Hz, 1H), 7.36 (t, J=7.9 Hz, 1H), 7.08 (s, 1H), 4.02 (s, 2H), 3.79 (s, 3H), 2.66 (s, 3H). LCMS (M+H)=486.1.

INTERMEDIATE 6

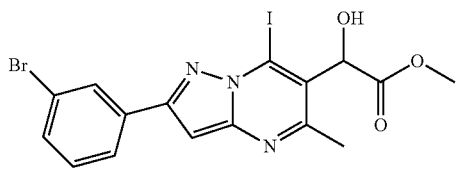 [SMILES: COC(=O)C(O)c1c(C)nc2cc(-c3cccc(Br)c3)nn2c1I]

Methyl 2-(2-(3-bromophenyl)-7-iodo-5-methylpyrazolo[1,5-a]pyrimidin-6-yl)-2-hydroxyacetate To a stirred solution of 0.9M KHMDS/THF (2.55 mL, 2.297 mmol) in THF (8 mL) at −78° C. was added dropwise a THF (10 mL) solution of methyl 2-(2-(3-bromophenyl)-7-iodo-5-methylpyrazolo[1,5-a]pyrimidin-6-yl)acetate (859 mg, 1.767 mmol) over 5 min. After 30 min, a THF (10 mL) solution of 3-phenyl-2-(phenylsulfonyl)-1,2-oxaziridine (600 mg, 2.297 mmol) was added to the resulting red reaction mixture and stirred for additional 30 min at −78° C. Then, the resulting orange reaction mixture was quenched with sat. NH$_4$Cl (50 mL), diluted with EtOAc (200 mL), washed with water (100 mL), brine (100 mL), dried (Na$_2$SO$_4$), filtered and concentrated to give light solid. This solid was triturated with small amount of ethyl acetate and solids were filtered, washed with hexanes and dried under high vacuo to afford methyl 2-(2-(3-bromophenyl)-7-iodo-5-methylpyrazolo[1,5-a]pyrimidin-6-yl)-2-hydroxyacetate (600 mg, 1.195 mmol, 67.6% yield) as light yellow solid. $^1$H NMR (500 MHz, CDCl$_3$) δ: 8.21 (t, J=1.7 Hz, 1H), 7.96 (dt, J=7.8, 1.2 Hz, 1H), 7.59-7.55 (m, 1H), 7.37 (t, J=7.8 Hz, 1H), 7.09 (s, 1H), 5.78 (s, 1H), 3.87 (s, 3H), 3.54 (br. s., 1H), 2.61 (s, 3H). LCMS (M+H)=504.05.

INTERMEDIATE 7

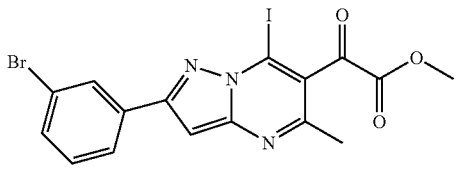 [SMILES: COC(=O)C(=O)c1c(C)nc2cc(-c3cccc(Br)c3)nn2c1I]

Methyl 2-(2-(3-bromophenyl)-7-iodo-5-methylpyrazolo[1,5-a]pyrimidin-6-yl)-2-oxoacetate To a mixture of methyl 2-(2-(3-bromophenyl)-7-iodo-5-methylpyrazolo[1,5-a]pyrimidin-6-yl)-2-hydroxyacetate (2.6 g, 5.18 mmol) in CH$_2$Cl$_2$ (100 mL) was added Dess-Martin Periodinane (2.196 g, 5.18 mmol) and the resulting mixture was stirred at room temperature for 1 h. The reaction mixture was diluted with ethyl acetate (500 mL), washed with sat. NaHCO$_3$ solution (100 mL), dried (Na$_2$SO$_4$), filtered and concentrated. The residue was purified by silica gel chromatography (5-70% EtOAc/hexane) to afford desired methyl 2-(2-(3-bromophenyl)-7-iodo-5-methylpyrazolo[1,5-a]pyrimidin-6-yl)-2-oxoacetate (1.7 g, 3.40 mmol, 65.6% yield) as off-white solid. $^1$H NMR (500 MHz, CDCl$_3$) δ: 8.21 (t, J=1.7 Hz, 1H), 7.96 (dt, J=7.7, 1.3 Hz, 1H), 7.61-7.58 (m, 1H), 7.39 (t, J=7.9 Hz, 1H), 7.14 (s, 1H), 4.03 (s, 3H), 2.57 (s, 3H). LCMS (M+H)=501.0.

INTERMEDIATE 8

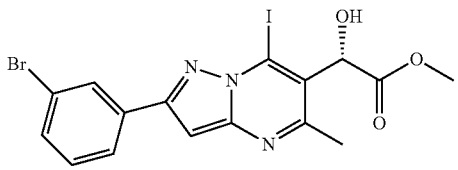 [SMILES: COC(=O)[C@@H](O)c1c(C)nc2cc(-c3cccc(Br)c3)nn2c1I]

(S)-Methyl 2-(2-(3-bromophenyl)-7-iodo-5-methylpyrazolo[1,5-a]pyrimidin-6-yl)-2-hydroxyacetate To a stirred yellow solution of methyl 2-(2-(3-bromophenyl)-7-iodo-5-methylpyrazolo[1,5-a]pyrimidin-6-yl)-2-oxoacetate (1.7 g, 3.40 mmol) in anhydrous toluene (100 mL) was added 1.1M (R)-1-methyl-3,3-diphenylhexahydropyrrolo[1,2-c][1,3,2]oxazaborole/toluene (1.236 mL, 1.360 mmol). The mixture was cooled to −35° C. and a solution of catechoborane/toluene (1.166 mL, 4.76 mmol) was added over 5 min. After 30 min, the reaction mixture was slowly warmed to −15° C. and stirred for additional 2 h. and diluted with EtOAc (600 mL) and sat. Na$_2$CO$_3$ (100 mL). The mixture was stirred vigorously for 30 min, and the organic phase washed with sat Na$_2$CO$_3$ (2×100 mL), dried (Na$_2$SO$_4$), filtered, concentrated and the residue was purified by silica gel chromatography (5-100% EtOAc/hexane) to afford desired (S)-methyl 2-(2-(3-bromophenyl)-7-iodo-5-methylpyrazolo[1,5-a]pyrimidin-6-yl)-2-hydroxyacetate (1 g, 1.992 mmol, 58.6% yield) as off-white solid. $^1$H NMR (500 MHz, CDCl$_3$) δ: 8.21 (t, J=1.7 Hz, 1H), 7.96 (dt, J=7.8, 1.2 Hz, 1H), 7.59-7.55 (m, 1H), 7.37 (t, J=7.8 Hz, 1H), 7.09 (s, 1H), 5.78 (s, 1H), 3.87 (s, 3H), 3.54 (br. s., 1H), 2.61 (s, 3H). LCMS (M+H)=504.05.

INTERMEDIATE 9

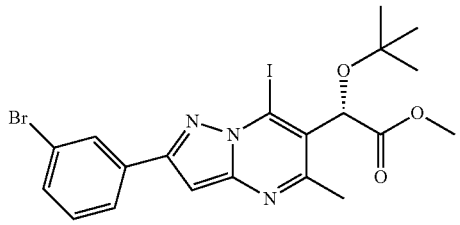 [SMILES: COC(=O)[C@@H](OC(C)(C)C)c1c(C)nc2cc(-c3cccc(Br)c3)nn2c1I]

(S)-Methyl 2-(2-(3-bromophenyl)-7-iodo-5-methylpyrazolo[1,5-a]pyrimidin-6-yl)-2-(tert-butoxy)acetate To a stirred solution of (S)-methyl 2-(2-(3-bromophenyl)-7-iodo-5-methylpyrazolo[1,5-a]pyrimidin-6-yl)-2-hydroxyacetate (1 g, 1.992 mmol) in CH$_2$Cl$_2$ (30 mL) and t-butyl acetate (21.00 mL) at rt was added 70% perchloric acid (0.513 mL, 5.97 mmol). After 3 h, the reaction mixture was diluted with CH$_2$Cl$_2$ (100 mL), carefully quenched with sat. NaHCO$_3$ (50 mL), organic layer separated and washed with brine (100 mL), dried (Na$_2$SO$_4$), filtered and concentrated to give yellow liquid. This was purified by flash column chromatography on silica gel column using (10-50% EtOAc/Hex as eluant) to afford (S)-methyl 2-(2-(3-bromophenyl)-7-iodo-5-methylpyrazolo[1,5-a]pyrimidin-6-yl)-2-(tert-butoxy)acetate (800 mg, 1.433 mmol, 72.0% yield) as yellow solid. $^1$H NMR (500 MHz, CDCl$_3$) δ: 8.20 (s, 1H), 7.95 (d, J=7.7 Hz, 1H), 7.56 (d, J=7.9 Hz, 1H), 7.37 (t, J=7.9 Hz, 1H), 7.08 (s, 1H), 5.59 (s, 1H), 3.76 (s, 3H), 2.70 (s, 3H), 1.32 (s, 9H). LCMS (M+H)=560.15.

INTERMEDIATE 10

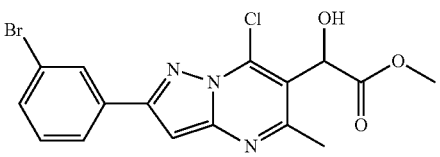

Methyl 2-(2-(3-bromophenyl)-7-chloro-5-methylpyrazolo[1,5-a]pyrimidin-6-yl)-2-hydroxyacetate To a stirred solution of 0.91M KHMDS/THF (95 mL, 95 mmol) in THF (50 mL) at −78° C. was added dropwise a solution of methyl 2-(2-(3-bromophenyl)-7-chloro-5-methylpyrazolo[1,5-a]pyrimidin-6-yl)acetate (25 g, 63.3 mmol) in THF (300 mL). After 1 h, 3-phenyl-2-(phenylsulfonyl)-1,2-oxaziridine (24.8 g, 95 mmol) in THF (100 mL) was added over the course of 10 min. This red reaction mixture was stirred at −78° C. for 2 h. Then, the resulting orange solution was quenched with sat. aq. NH₄Cl (400 mL), diluted with EtOAc (400 mL), and partitioned with a sep. funnel. The organic phase was washed with water and brine. The organic phase was dried (Na₂SO₄), filtered, and concentrated to give a light brown solid. Trituration with hexanes followed by trituration with ether (5×50 mL) gave 21 g of a yellow solid: methyl 2-(2-(3-bromophenyl)-7-chloro-5-methylpyrazolo[1,5-a]pyrimidin-6-yl)-2-hydroxyacetate (as a 1:1 complex with benzenesulfonamide). ¹H NMR (400 MHz, CDCl3) δ 8.20 (t, J=1.8 Hz, 1H), 7.95 (dq, J=7.8, 0.8 Hz, 1H), 7.57 (ddd, J=8.0, 2.0, 1.0 Hz, 1H), 7.37 (t, J=7.9 Hz, 1H), 6.95 (s, 1H), 5.79 (s, 1H), 3.87 (s, 3H), 3.59 (d, J=1.8 Hz, 1H), 2.65 (s, 3H). LCMS (M+H)=410 and 412.

INTERMEDIATE 11

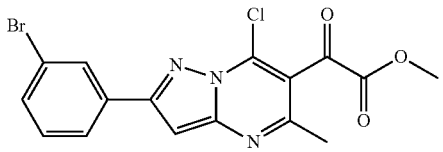 [SMILES: COC(=O)C(=O)c1c(C)nc2cc(-c3cccc(Br)c3)nn2c1Cl]

Methyl 2-(2-(3-bromophenyl)-7-chloro-5-methylpyrazolo[1,5-a]pyrimidin-6-yl)-2-oxoacetate To a stirred inseparable mixture of methyl 2-(2-(3-bromophenyl)-7-chloro-5-methylpyrazolo[1,5-a]pyrimidin-6-yl)-2-hydroxyacetate (12.9 g, 31.4 mmol) and benzenesulfonamide (2.96 g, 18.85 mmol) in CH₂Cl₂ (700 mL) was added Dess-Martin Periodinane (13.3 g, 31.4 mmol). Stir for 60 min at rt at which time the reaction appeared complete by TLC (1:1 hexane/EtOAc). The reaction was placed in the refrigerator for 2 h and then filtered through a medium fritted glass funnel. The brown homogeneous solution was treated with 140 mL of sat.aq. Na₂CO₃ and stirred rapidly for 30 min. The organic phase was separated and washed with additional sat.aq. Na₂CO₃ in a separatory funnel. The organic phase was dried (Na₂SO₄) and filtered through celite. The filtrate was then filtered through 170 g of silica gel with the aid of another 1 L of CH₂Cl₂. The light yellow filtrate was concentrated in vacuo to give 9.5 g of a yellow solid which after further drying gave 8.43 g (66%) of methyl 2-(2-(3-bromophenyl)-7-chloro-5-methylpyrazolo[1,5-a]pyrimidin-6-yl)-2-oxoacetate as a light yellow solid. ¹H NMR (400 MHz, CDCl3) δ 8.21 (t, J=1.6 Hz, 1H), 7.96 (d, J=7.8 Hz, 1H), 7.60 (dt, J=8.0, 0.9 Hz, 1H), 7.39 (t, J=7.9 Hz, 1H), 7.02 (s, 1H), 4.03 (s, 3H), 2.65 (s, 3H). LCMS (M+H)=408 and 410.

INTERMEDIATE 12

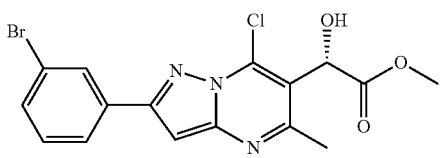 [SMILES: COC(=O)[C@@H](O)c1c(C)nc2cc(-c3cccc(Br)c3)nn2c1Cl]

(S)-Methyl 2-(2-(3-bromophenyl)-7-chloro-5-methylpyrazolo[1,5-a]pyrimidin-6-yl)-2-hydroxyacetate To a stirred solution of methyl 2-(2-(3-bromophenyl)-7-chloro-5-methylpyrazolo[1,5-a]pyrimidin-6-yl)-2-oxoacetate (14 g, 34.3 mmol) in anhydrous toluene (400 mL) was added 1.1M (R)-1-methyl-3,3-diphenylhexahydropyrrolo[1,2-c][1,3,2]oxazaborole/toluene (12.5 mL, 13.7 mmol). The mixture was cooled to −35° C. and then a 4.17M solution of catechoborane/toluene (11.7 mL, 48 mmol) was added over the course of 10 min. After 30 min, the reaction mixture was slowly warmed to −15° C. and stirred for additional 2 h. At this point the reaction mixture was diluted with EtOAc (300 mL) and treated with sat.aq. Na₂CO₃ (50 mL). The mixture was stirred vigorously for 10 min. The organic phase was separated and washed with sat. aq. Na₂CO₃ (5×100 mL), 0.1N HCl (1×100 mL), and brine. The organic phase was dried (Na₂SO₄), filtered, and concentrated. The residue was triturated with ether to obtain 12 g (77%) of the desired (S)-methyl 2-(2-(3-bromophenyl)-7-chloro-5-methylpyrazolo[1,5-a]pyrimidin-6-yl)-2-hydroxyacetate as a colorless oil. ¹H NMR (400 MHz, CDCl₃) δ 8.20 (t, J=1.8 Hz, 1H), 7.95 (dq, J=7.8, 0.8 Hz, 1H), 7.57 (ddd, J=8.0, 2.0, 1.0 Hz, 1H), 7.37 (t, J=7.9 Hz, 1H), 6.95 (s, 1H), 5.79 (s, 1H), 3.87 (s, 3H), 3.59 (d, J=1.8 Hz, 1H), 2.65 (s, 3H). LCMS (M+H)=410 and 412.

INTERMEDIATE 13

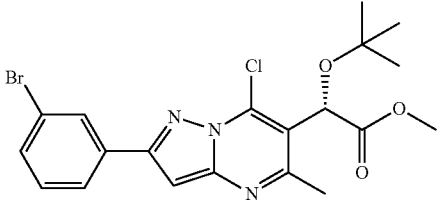 [SMILES: COC(=O)[C@@H](OC(C)(C)C)c1c(C)nc2cc(-c3cccc(Br)c3)nn2c1Cl]

(S)-Methyl 2-(2-(3-bromophenyl)-7-chloro-5-methylpyrazolo[1,5-a]pyrimidin-6-yl)-2-(tert-butoxy)acetate A mixture of (S)-methyl 2-(2-(3-bromophenyl)-7-chloro-5-methylpyrazolo[1,5-a]pyrimidin-6-yl)-2-hydroxyacetate (7.81 g, 19.02 mmol), t-butylacetate (160 mL) in DCM (330 mL) was added perchloric acid (3.43 mL, 57.1 mmol) and the mixture was stirred at rt for 3 h. It was then quenched with sat.aq. NaHCO₃ (adjusted to pH=7-8 by the addition of solid NaHCO₃). This mixture was diluted with EtOAc and the organic phase was washed with water. The organic phase was dried (MgSO₄), filtered, and concentrated in vacuo to obtain ~7 g of crude product as an oil. Filtration through 70 g of silica gel eluting with CH₂Cl₂ gave (S)-methyl 2-(2-(3-bromophenyl)-7-chloro-5-methylpyrazolo[1,5-a]pyrimidin-6-yl)-2-(tert-butoxy)acetate (5.71 g, 12.23 mmol, 64.3% yield). ¹H NMR (400 MHz, CDCl₃) δ 8.20 (t, J=1.6 Hz, 1H), 7.95 (dt, J=7.8, 1.1 Hz, 1H), 7.63-7.53 (m, 1H), 7.37 (t, J=7.9 Hz, 1H), 6.94 (s, 1H), 5.69 (s, 1H), 3.76 (s, 3H), 2.70 (s, 3H), 1.30 (s, 9H). LCMS (M+H)=466 and 468.

INTERMEDIATE 14

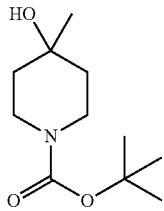

tert-Butyl
4-hydroxy-4-methylpiperidine-1-carboxylate

Under an $N_2$ atmosphere, a 3N MeMgBr/ether (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. $NH_4Cl$. Another 20 mL of ether was added and the mixture was partitioned in a separatory funnel. The organic phase was set aside and the aqueous phase was extracted with another 20 mL of ether. The combined ether extracts were dried over $MgSO_4$, filtered and evaporated to obtain an oil, which was then purified by biotage, eluting with 0-50% EtOAc/hexane to obtain tert-butyl 4-hydroxy-4-methylpiperidine-1-carboxylate (4.30 g, 18.0 mmol, 90% yield) as a colorless oil. $^1$H NMR (500 MHz, $CDCl_3$) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

INTERMEDIATE 15

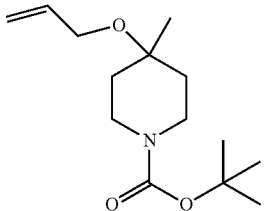 [SMILES: C=CCOC1(C)CCN(C(=O)OC(C)(C)C)CC1]

tert-Butyl
4-(allyloxy)-4-methylpiperidine-1-carboxylate

To a mixture of tert-butyl 4-hydroxy-4-methylpiperidine-1-carboxylate (4.30 g, 20.0 mmol) in DMF (50 mL) at 0° C. was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. $NH_4Cl$. The reaction mixture was extracted with ether. The organic phase was dried over $MgSO_4$, filtered and concentrated to obtain a colorless oil, which was then purified by biotage, eluting with 0-25% EtOAc/hexane to isolate 3.1 g (61%) of tert-butyl 4-(allyloxy)-4-methylpiperidine-1-carboxylate as a colorless oil. $^1$H NMR (500 MHz, $CDCl_3$) δ 6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

INTERMEDIATE 16

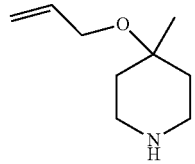

4-(Allyloxy)-4-methylpiperidine hydrochloride

A mixture of tert-butyl 4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. $^1$H NMR (500 MHz, METHANOL-$d_4$) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H).

INTERMEDIATE 17

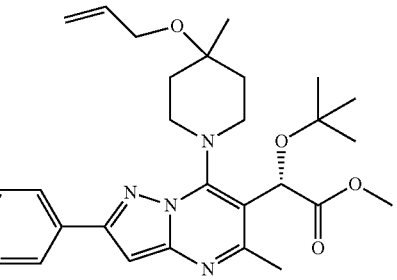

(S)-Methyl 2-(7-(4-(allyloxy)-4-methylpiperidin-1-yl)-2-(3-bromophenyl)-5-methylpyrazolo[1,5-c]pyrimidin-6-yl)-2-(tert-butoxy)acetate (S)-methyl 2-(2-(3-bromophenyl)-7-chloro-5-methylpyrazolo[1,5-a]pyrimidin-6-yl)-2-(tert-butoxy)acetate (10.9 g, 23.3 mmol) was dissolved in DMF (100 mL). After flushing with $N_2$, 4-(allyloxy)-4-methylpiperidine.HCl (7.34 g, 35.0 mmol) and Hunig's Base (12.22 mL, 70.0 mmol) were added to the reaction mixture. After stirring for 18 h at rt, the reaction was heated at 50° C. for 3 h to complete the reaction. The reaction mixture was concentrated in vacuo at 50° C. to remove most of the DMF. The residue was partitioned between EtOAc and 0.01N HCl. The organic phase was washed with water and brine. Then, the organic phase was dried ($MgSO_4$), filtered, and concentrated in vacuo. The residue was dissolved in about 600 mL of hot hexanes and cooled for 18 h in the freezer to give a crystalline solid. Filtration gave 6.5 g of (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate. The filtrate was purified by Biotage (10-50% EtOAc)

to give another 5.71 g of (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate. The combined yield of the desired product was 12.21 g (89%). $^1$H NMR (400 MHz, METHANOL-$d_4$) δ 8.23 (t, J=1.8 Hz, 1H), 8.01 (dt, J=7.8, 1.3 Hz, 1H), 7.60-7.55 (m, 1H), 7.43-7.37 (m, 1H), 6.90 (s, 1H), 6.18-5.95 (m, 2H), 5.48 (d, J=17.3 Hz, 1H), 5.25 (d, J=10.0 Hz, 1H), 4.11-4.06 (m, 2H), 3.77 (s, 3H), 2.59 (s, 3H), 2.14-1.95 (m, 3H), 1.82-1.71 (m, 1H), 1.37 (s, 3H), 1.28 (s, 9H). LCMS (M+H)=585 and 587.

INTERMEDIATE 18

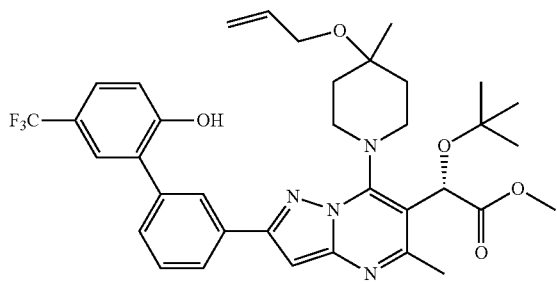 [SMILES: C=CCOC1(C)CCN(c2c([C@H](OC(C)(C)C)C(=O)OC)c(C)nc3cc(-c4cccc(-c5cc(C(F)(F)F)ccc5O)c4)nn23)CC1]

(S)-Methyl 2-(7-(4-(allyloxy)-4-methylpiperidin-1-yl)-2-(2'-hydroxy-5'-(trifluoromethyl)-[1,1'-biphenyl]-3-yl)-5-methylpyrazolo[1,5-a]pyrimidin-6-yl)-2-(tert-butoxy)acetate A mixture of (2-hydroxy-5-(trifluoromethyl)phenyl)boronic acid (106 mg, 0.512 mmol), (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (150 mg, 0.256 mmol), Na$_2$CO$_3$ (0.320 mL, 0.640 mmol) in DMF (1 mL) was vacuum, back-filled with N$_2$ for 3 times. To this mixture added Pd(Ph$_3$P)$_4$ (29.6 mg, 0.026 mmol) and heated at 95° C. in a microwave tube for 1 h. The mixture was then diluted with EtOAc, washed with water. The organic layer was dried over MgSO$_4$, filtered and concentrated to obtain 150 mg of an oil, which was then purified by biotage, eluting with 50% EtOAc/hexane to isolate (S)-methyl 2-(7-(4-(allyloxy)-4-methylpiperidin-1-yl)-2-(2'-hydroxy-5'-(trifluoromethyl)-[1,1'-biphenyl]-3-yl)-5-methylpyrazolo[1,5-a]pyrimidin-6-yl)-2-(tert-butoxy)acetate (89 mg, 52%) as a white solid. $^1$H NMR (400 MHz, CDCl$_3$) δ 8.14 (s, 1H), 8.07 (d, J=7.8 Hz, 1H), 7.65-7.54 (m, 3H), 7.49 (d, J=7.6 Hz, 1H), 7.12 (d, J=8.3 Hz, 1H), 6.85 (s, 1H), 6.28 (br. s., 1H), 6.05-5.83 (m, 2H), 5.39 (d, J=17.4 Hz, 1H), 5.09 (br. s., 1H), 4.01 (d, J=4.4 Hz, 2H), 3.76 (s, 3H), 2.62 (s, 3H), 2.08-1.93 (m, 3H), 1.73 (br. s., 1H), 1.36 (s, 3H), 1.29-1.22 (m, 9H), 4 protons from piperidine were missing. LCMS (M+1)=667.6.

INTERMEDIATE 19

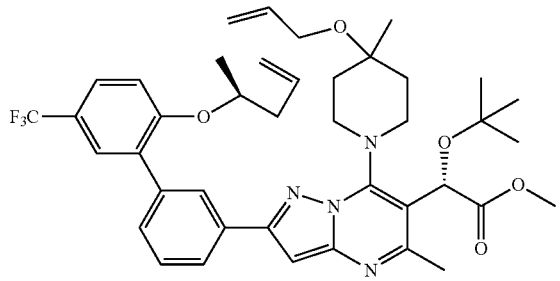 [SMILES: C=CCOC1(C)CCN(c2c([C@H](OC(C)(C)C)C(=O)OC)c(C)nc3cc(-c4cccc(-c5cc(C(F)(F)F)ccc5O[C@@H](C)CC=C)c4)nn23)CC1]

(S)-Methyl 2-(7-(4-(allyloxy)-4-methylpiperidin-1-yl)-5-methyl-2-(2'-((S)-pent-4-en-2-yloxy)-5'-(trifluoromethyl)-[1,1'-biphenyl]-3-yl)pyrazolo[1,5-a]pyrimidin-6-yl)-2-(tert-butoxy)acetate A mixture of (S)-methyl 2-(7-(4-(allyloxy)-4-methylpiperidin-1-yl)-2-(2'-hydroxy-5'-(trifluoromethyl)-[1,1'-biphenyl]-3-yl)-5-methylpyrazolo[1,5-a]pyrimidin-6-yl)-2-(tert-butoxy)acetate (89 mg, 0.133 mmol), (R)-pent-4-en-2-ol (34.5 mg, 0.400 mmol), triphenylphosphine (105 mg, 0.400 mmol) and DEAD (69.7 mg, 0.400 mmol) in THF (2 mL) was stirred at rt for 3 h. It was then concentrated and diluted with EtOAc. The mixture was washed with water. The organic layer was dried over MgSO$_4$, filtered and concentrated to obtain 100 mg of a yellow oil, which was then purified by biotage, eluting with 30% EtOAc/hexane to isolate (S)-methyl 2-(7-(4-(allyloxy)-4-methylpiperidin-1-yl)-5-methyl-2-(2'-((S)-pent-4-en-2-yloxy)-5'-(trifluoromethyl)-[1,1'-biphenyl]-3-yl)pyrazolo[1,5-a]pyrimidin-6-yl)-2-(tert-butoxy)acetate (74 mg, 75%) as an oil. LCMS (M+1)=735.8.

INTERMEDIATE 20

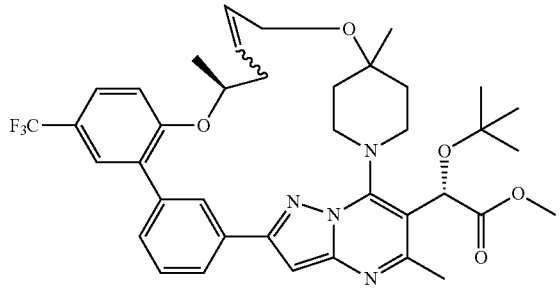 [SMILES: COC(=O)[C@@H](OC(C)(C)C)c1c(C)nc2cc3nn2c1N1CCC(C)(CC1)OCC=CC[C@H](C)Oc1ccc(C(F)(F)F)cc1-c1cccc-3c1]

Methyl (2S)-2-(tert-butoxy)-2-[(22S)-4,22,28-trimethyl-17-(trifluoromethyl)-21,27-dioxa-1,5,7,8-tetraazahexacyclo[26.2.2.1[6,9].1[10,14].0[2,7].0[15,20]]tetratriaconta-2,4,6(34),8,10(33),11,13,15(20),16,18,24-undecaen-3-yl]acetate A mixture of (S)-methyl 2-(7-(4-(allyloxy)-4-methylpiperidin-1-yl)-5-methyl-2-(2'-((S)-pent-4-en-2-yloxy)-5'-(trifluoromethyl)-[1,1'-biphenyl]-3-yl)pyrazolo[1,5-a]pyrimidin-6-yl)-2-(tert-butoxy)acetate (74 mg, 0.101 mmol), (1,3-dimesitylimidazolidin-2-ylidene)(2- isopropoxybenzylidene)ruthenium(VI) chloride (6.31 mg, 10.07 μmol), copper(I) iodide (19.18 mg, 0.101 mmol) in ClCH$_2$CH$_2$Cl (80 mL) was refluxed for 3 h. It was then concentrated and purified by biotage, eluting with 20% EtOAc/hexane to isolate of methyl (2S)-2-(tert-butoxy)-2-[(22S,24E/Z)-4,22,28-trimethyl-17-(trifluoromethyl)-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (50 mg, 70%) as an off-white solid. The product is a mixture of cis/trans isomers. LCMS (M+1)=707.3.

INTERMEDIATE 21

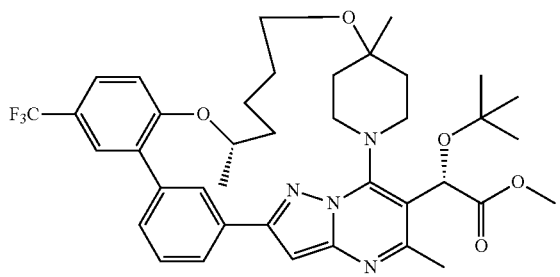

Methyl (2S)-2-(tert-butoxy)-2-[(22S)-4,22,28-trimethyl-17-(trifluoromethyl)-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate A mixture of methyl (2S)-2-(tert-butoxy)-2-[(22S,24Z)-4,22,28-trimethyl-17-(trifluoromethyl)-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (50 mg, 0.071 mmol), Pd/C (7.53 mg, 7.07 μmol) in MeOH (2 mL) was stirred under a H$_2$ balloon for 2 h. It was then filtered, concentrated and purified by biotage, eluting with 20% EtOAc/hexane to isolate methyl (2S)-2-(tert-butoxy)-2-[(22S)-4,22,28-trimethyl-17-(trifluoromethyl)-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (38 mg, 75%) as an off-white solid. LCMS (M+1)=709.3.

EXAMPLE 1

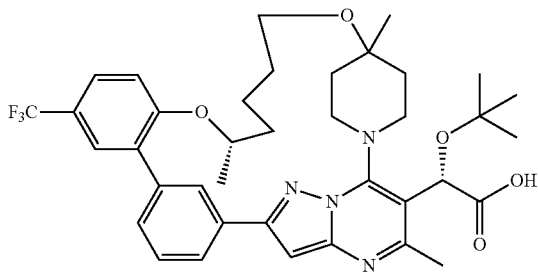 [SMILES: Cc1nc2cc3nn2c(c1[C@H](OC(C)(C)C)C(=O)O)N1CCC(C)(CC1)OCCCC[C@H](C)Oc1ccc(C(F)(F)F)cc1-c1cccc-3c1]

(2S)-2-(tert-Butoxy)-2-[(22S)-4,22,28-trimethyl-17-(trifluoromethyl)-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl] acetic acid A mixture of methyl (2S)-2-(tert-butoxy)-2-[(22S)-4,22,28-trimethyl-17-(trifluoromethyl)-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (38 mg, 0.054 mmol) and 1N NaOH (0.268 mL, 0.268 mmol) in MeOH (2 mL) was refluxed for 3 h. It was then filtered and purified by prep HPLC to isolate (2S)-2-(tert-butoxy)-2-[(22S)-4,22,28-trimethyl-17-(trifluoromethyl)-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid (20 mg, 51%) as a white solid. $^1$H NMR (600 MHz, DMSO-d6) δ 8.49 (s, 1H), 7.99 (d, J=7.9 Hz, 1H), 7.70 (d, J=8.6 Hz, 1H), 7.60-7.51 (m, 2H), 7.38 (t, J=7.4 Hz, 2H), 7.10 (s, 1H), 5.67 (br. s., 1H), 4.84-4.76 (m, 1H), 4.47 (t, J=12.2 Hz, 1H), 3.59 (t, J=11.7 Hz, 3H), 2.80 (d, J=11.2 Hz, 1H), 2.52 (d, J=7.5 Hz, 6H), 1.98-1.86 (m, 3H), 1.78-1.62 (m, 4H), 1.58-1.43 (m, 3H), 1.19-1.15 (m, 14H), 1.12 (d, J=5.9 Hz, 3H). LCMS (M+1)=695.3.

INTERMEDIATE 22

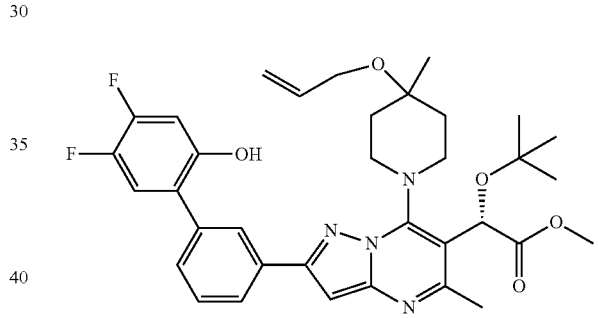

(S)-Methyl 2-(7-(4-(allyloxy)-4-methylpiperidin-1-yl)-2-(4',5'-difluoro-2'-hydroxy-[1,1'-biphenyl]-3-yl)-5-methylpyrazolo[1,5-a]pyrimidin-6-yl)-2-(tert-butoxy)acetate To (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (0.20 g, 0.33 mmol, 1 equiv), (4,5-difluoro-2-hydroxyphenyl)boronic acid (174 mg, 1.00 mmol, 3 equiv), and Pd(PPh$_3$)$_4$ (39 mg, 0.033 mmol, 0.1 equiv) was added DMF (3.3 mL that had been degassed by sparging with nitrogen for 10 min). Na$_2$CO$_3$ (0.33 mL of a 2 M aqueous solution, 0.66 mmol, 2 equiv) was added and the reaction was heated to 90° C. for 3 h. Upon cooling to ambient temperature, the reaction was diluted with EtOAc and washed with water. The EtOAc layer was dried (Na$_2$SO$_4$) and concentrated in vacuo. The crude product was purified by flash column chromatography (0-60% acetone in hexane) to provide the product as a yellow foam (0.15 g, 69%). LCMS (ESI, M+1): 649.3.

INTERMEDIATE 23

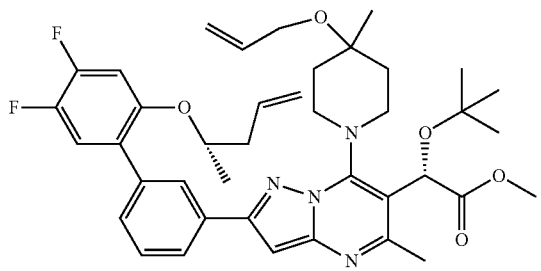 [SMILES: C=CCOC1(C)CCN(c2c([C@H](OC(C)(C)C)C(=O)OC)c(C)nc3cc(-c4cccc(-c5cc(F)c(F)cc5O[C@@H](C)CC=C)c4)nn23)CC1]

(S)-Methyl 2-(7-(4-(allyloxy)-4-methylpiperidin-1-yl)-2-(4',5'-difluoro-2'-((S)-pent-4-en-2-yloxy)-[1,1'-biphenyl]-3-yl)-5-methylpyrazolo[1,5-a]pyrimidin-6-yl)-2-(tert-butoxy)acetate To a solution of (S)-methyl 2-(7-(4-(allyloxy)-4-methylpiperidin-1-yl)-2-(4',5'-difluoro-2'-hydroxy-[1,1'-biphenyl]-3-yl)-5-methylpyrazolo[1,5-a]pyrimidin-6-yl)-2-(tert-butoxy)acetate (0.15 g, 0.23 mmol, 1 equiv), (R)-pent-4-en-2-ol (40 mg, 0.46 mmol, 2 equiv), and PPh$_3$ (0.12 g, 0.46 mmol, 2 equiv) in THF (2.3 mL) was added DEAD (0.21 mL of a 40% solution in THF, 0.46 mmol, 2 equiv). After stirring 18 h, the reaction was concentrated in vacuo directly onto silica gel and purified by flash column chromatography (0-10% EtOAc in hexane) to provide the product as a white foam (0.12 g, 72%). LCMS (ESI, M+1): 717.35.

EXAMPLE 2

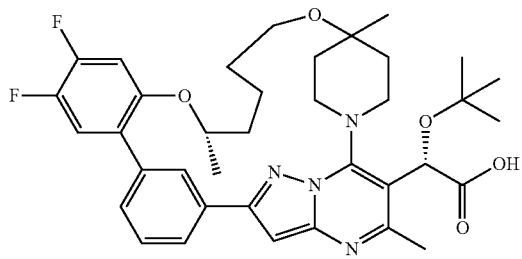 [SMILES: Cc1nc2cc3nn2c(c1[C@H](OC(C)(C)C)C(=O)O)N1CCC(C)(CC1)OCCCC[C@H](C)Oc1cc(F)c(F)cc1-c1cccc-3c1]

(2S)-2-(tert-Butoxy)-2-[(22S)-17,18-difluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid A solution of (S)-methyl 2-(7-(4-(allyloxy)-4-methylpiperidin-1-yl)-2-(4',5'-difluoro-2'-((S)-pent-4-en-2-yloxy)-[1,1'-biphenyl]-3-yl)-5-methylpyrazolo[1,5-a]pyrimidin-6-yl)-2-(tert-butoxy)acetate (80 mg, 0.112 mmol, 1 equiv) in DCE (56 mL) was heated to 90° C. The Hoyveda Grubbs 2$^{nd}$ generation catalyst (10 mg, 0.017 mmol, 0.15 equiv) was added. The pale green brown solution was stirred for 5 h and then allowed to cool to ambient temperature. The reaction was concentrated in vacuo and the crude product was used as is. LCMS (ESI, M+1): 689.3. The residue was then taken up in MeOH (2.4 mL) and NaBH$_4$ (14 mg, 0.36 mmol, 5 equiv) was added. After stirring 1 h, the reaction was diluted with EtOAc and washed with 0.5 N HCl. The EtOAc layer was dried (Na$_2$SO$_4$) and concentrated in vacuo. The residue was dissolved in 3:2:1 MeOH:THF:water (2.4 mL) and LiOH (17 mg, 0.726 mmol, 10 equiv) was added. The reaction was heated at 60° C. for 3 h. Upon cooling to ambient temperature, the reaction was purified via preparative HPLC to afford desired product (12 mg, 18%). $^1$H NMR (600 MHz, DMSO-d$_6$) δ 8.47 (s, 1H), 7.93 (d, J=7.7 Hz, 1H), 7.51 (t, J=7.7 Hz, 1H), 7.41-7.29 (m, 3H), 7.07-7.04 (m, 1H), 5.56 (s, 1H), 4.63 (br. s., 1H), 4.44 (t, J=12.3 Hz, 1H), 3.40 (br. s., 1H), 3.31 (br. s., 1H), 2.88 (q, J=7.0 Hz, 2H), 2.79 (d, J=10.3 Hz, 1H), 2.50 (s, 3H), 1.97-1.43 (m, 10H), 1.16 (br. s., 3H), 1.13 (s, 9H), 1.06 (d, J=5.5 Hz, 3H); LCMS (ESI, M): 662.3.

INTERMEDIATE 24

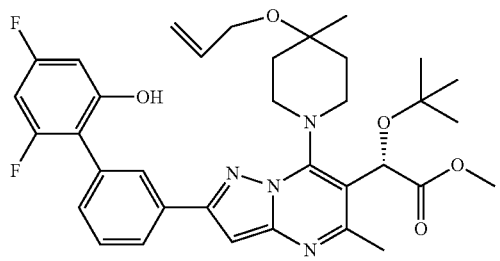 [SMILES: C=CCOC1(C)CCN(c2c([C@H](OC(C)(C)C)C(=O)OC)c(C)nc3cc(-c4cccc(-c5c(O)cc(F)cc5F)c4)nn23)CC1]

(S)-Methyl 2-(7-(4-(allyloxy)-4-methylpiperidin-1-yl)-2-(2',4'-difluoro-6'-hydroxy-[1,1'-biphenyl]-3-yl)-5-methylpyrazolo[1,5-a]pyrimidin-6-yl)-2-(tert-butoxy)acetate To (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (0.129 g, 0.216 mmol, 1 equiv), (3,5-difluoro-2-hydroxyphenyl)boronic acid (75 mg, 0.431 mmol, 2 equiv), and Pd(PPh$_3$)$_4$ (25 mg, 0.022 mmol, 0.1 equiv) was added DMF (2.2 mL that had been degassed by sparging with nitrogen for 10 min). Na$_2$CO$_3$ (0.22 mL of a 2 M aqueous solution, 0.431 mmol, 2 equiv) was added and the reaction was heated to 90° C. for 3 h. Upon cooling to ambient temperature, the reaction was diluted with EtOAc and washed with water. The EtOAc layer was dried (Na$_2$SO$_4$) and concentrated in vacuo. The crude product was purified by flash column chromatography (0-100% EtOAc in hexane) to provide the product as a yellow foam (0.102 g, 73%). $^1$H NMR (400 MHz, CDCl$_3$) δ 8.07 (d, J=7.8 Hz, 1H), 8.01 (s, 1H), 7.59 (t, J=7.8 Hz, 1H), 7.39 (d, J=7.5 Hz, 1H), 6.81 (s, 1H), 6.61 (d, J=9.8 Hz, 1H), 6.57-6.50 (m, J=2.5 Hz, 1H), 6.16-5.91 (m, 3H), 5.47-5.36 (m, 1H), 5.17-5.05 (m, 1H), 4.30-4.10 (m, 3H), 4.00 (d, J=4.5 Hz, 2H), 2.62 (s, 3H), 2.06 (s, 3H), 1.80-1.65 (m, 1H), 1.36 (s, 3H), 1.31-1.20 (m, 12H); 19F NMR (376 MHz, CDCl$_3$) δ −110.22 (br. s., 1F), −112.15 (br. s., 1F); LCMS (ESI, M+1): 649.3.

INTERMEDIATE 25

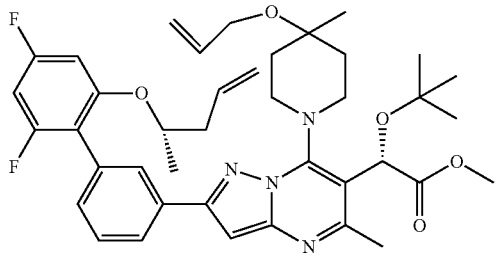 [SMILES: C=CCOC1(C)CCN(c2c([C@H](OC(C)(C)C)C(=O)OC)c(C)nc3cc(-c4cccc(-c5c(F)cc(F)cc5O[C@@H](C)CC=C)c4)nn23)CC1]

(S)-Methyl 2-(7-(4-(allyloxy)-4-methylpiperidin-1-yl)-2-(2',4'-difluoro-6'-((S)-pent-4-en-2-yloxy)-[1,1'-biphenyl]-3-yl)-5-methylpyrazolo[1,5-a]pyrimidin-6-yl)-2-(tert-butoxy)acetate To a solution of (S)-methyl 2-(7-(4-(allyloxy)-4-methylpiperidin-1-yl)-2-(2',4'-difluoro-6'-hydroxy-[1,1'-biphenyl]-3-yl)-5-methylpyrazolo[1,5-a]pyrimidin-6-yl)-2-(tert-butoxy)acetate (0.102 g, 0.157 mmol, 1 equiv), (R)-pent-4-en-2-ol (0.049 mL, 0.472 mmol, 3 equiv), and PPh$_3$ (0.82 g, 0.314 mmol, 2 equiv) in THF (1.6 mL) was added DIAD (0.061, 0.46 mmol, 2 equiv). After stirring 3 h, the reaction was diluted with EtOAc. EtOAc solution washed with water, dried (Na$_2$SO$_4$), and concentrated in vacuo. The crude product was purified by flash column chromatography (0-80% EtOAc in hexane) to provide the product as a colorless film (0.090 g, 80%). $^1$H NMR (400 MHz, CDCl$_3$) [note: 4H of piperidine not observed] δ 8.05 (d, J=7.5 Hz, 1H), 7.98 (s, 1H), 7.49 (t, J=7.8 Hz, 1H), 7.39 (d, J=7.5 Hz, 1H), 6.82 (s, 1H), 6.61-6.50 (m, 2H), 5.99 (dd, J=11.2, 5.9 Hz, 2H), 5.77-5.61 (m, 1H), 5.41 (d, J=17.1 Hz, 1H), 5.17-5.07 (m, 1H), 5.05-4.96 (m, 2H), 4.37 (d, J=6.0 Hz, 1H), 4.20 (dd, J=19.2, 7.2 Hz, 2H), 4.01 (d, J=4.5 Hz, 2H), 2.63 (s, 3H), 2.42-2.32 (m, 1H), 2.31-2.20 (m, 1H), 2.09-1.91 (m, 3H), 1.82-1.68 (m, 1H), 1.36 (br. s., 3H), 1.28-1.20 (m, 15H); $^{19}$F NMR (376 MHz, CDCl$_3$) δ -110.49 (br. s., 1F), -111.70 (br. s., 1F); LCMS (ESI, M+1): 717.3.

INTERMEDIATE 26

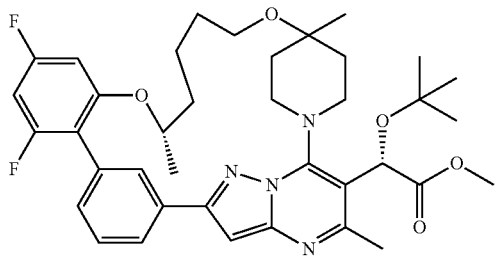 [SMILES: COC(=O)[C@@H](OC(C)(C)C)c1c(C)nc2cc3nn2c1N1CCC(C)(CC1)OCCCC[C@H](C)Oc1cc(F)cc(F)c1-c1cccc-3c1]

Methyl (2S)-2-(tert-butoxy)-2-[(22S)-16,18-difluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate A solution of (S)-methyl 2-(7-(4-(allyloxy)-4-methylpiperidin-1-yl)-2-(2',4'-difluoro-6'-((S)-pent-4-en-2-yloxy)-[1, 1'-biphenyl]-3-yl)-5-methylpyrazolo[1,5-a]pyrimidin-6-yl)-2-(tert-butoxy)acetate (90 mg, 0.126 mmol, 1 equiv) in toluene (100 mL) was heated to 80° C. The Hoyveda Grubbs 2$^{nd}$ generation catalyst (4 mg, 0.006 mmol, 0.05 equiv) was added. The pale green brown solution was stirred for 2 h and more Hoyveda Grubbs 2$^{nd}$ generation catalyst (4 mg, 0.006 mmol, 0.05 equiv) was added. After 1 h, the reaction was allowed to cool to ambient temperature. The reaction loaded directly onto silica and was purified by flash column chromatography (0-100% EtOAc/hex) to provide product (42 mg). LCMS (ESI, M+1): 689.25. The product thus obtained was dissolved in MeOH (2 mL) and 10% Pd/C (13 mg, 0.012 mmol, 0.2 equiv) was added. The reaction was put under a balloon of H$_2$. After 18 h, the reaction was filtered through celite eluting with MeOH and the filtrate was concentrated in vacuo. The crude product was purified by flash column chromatography (0-100% EtOAc in hexane) to provide the product as a white solid (0.038 g, 90%). $^1$H NMR (400 MHz, DMSO-d$_6$) δ 8.28-8.15 (m, 1H), 8.00-7.89 (m, 1H), 7.55-7.46 (m, 1H), 7.31-7.23 (m, 1H), 7.08-7.00 (m, 2H), 6.93-6.82 (m, 1H), 5.62-5.50 (m, 1H), 4.75-4.61 (m, 1H), 4.57-4.44 (m, 1H), 3.54-3.37 (m, 4H), 2.82-2.71 (m, 1H), 2.55 (s, 3H), 1.96-1.85 (m, 4H), 1.72-1.53 (m, 4H), 1.48-1.38 (m, 2H), 1.20-1.16 (m, 3H), 1.14 (s, 9H), 1.08 (d, J=6.0 Hz, 3H); $^{19}$F NMR (376 MHz, DMSO-d$_6$) δ -109.64 (br. s., 1F), -112.06 (s, 1F); LCMS (ESI, M+1): 663.6.

EXAMPLE 3

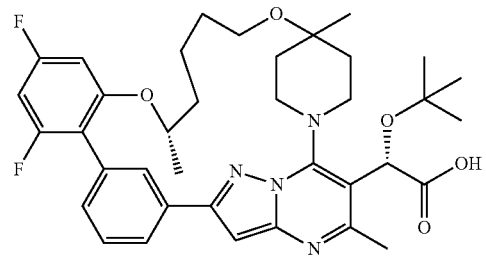 [SMILES: Cc1nc2cc3nn2c(c1[C@H](OC(C)(C)C)C(=O)O)N1CCC(C)(CC1)OCCCC[C@H](C)Oc1cc(F)cc(F)c1-c1cccc-3c1]

(2S)-2-(tert-Butoxy)-2-[(22S)-16,18-difluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid To a solution of methyl (2S)-2-(tert-butoxy)-2-[(22S)-16,18-difluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (46 mg, 0.055 mmol, 1 equiv) in 10:1 MeOH:water (1.1 mL) was added LiOH.H$_2$O (46 mg, 1.10 mmol, 20 equiv). The reaction was heated to 60° C. for 2 h. Upon cooling to ambient temperature, the reaction was filtered and purified via preparative HPLC to afford desired product (23 mg, 64%). $^1$H NMR (400 MHz, DMSO-d$_6$) δ 8.28-8.15 (m, 1H), 8.00-7.89 (m, 1H), 7.55-7.46 (m, 1H), 7.31-7.23 (m, 1H), 7.08-7.00 (m, 2H), 6.93-6.82 (m, 1H), 5.62-5.50 (m, 1H), 4.75-4.61 (m, 1H), 4.57-4.44 (m, 1H), 3.54-3.37 (m, 4H), 2.82-2.71 (m, 1H), 2.55 (s, 3H), 1.96-1.85 (m, 4H), 1.72-1.53 (m, 4H), 1.48-1.38 (m, 2H), 1.20-1.16 (m, 3H), 1.14 (s, 9H), 1.08 (d, J=6.0 Hz, 3H); $^{19}$F NMR (376 MHz, DMSO-d$_6$) δ -109.64 (br. s., 1F), -112.06 (s, 1F); LCMS (ESI, M+1): 663.6.

INTERMEDIATE 27

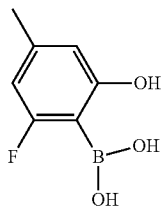

(2-Fluoro-6-hydroxy-4-methylphenyl)boronic acid

A solution of (2-fluoro-6-methoxy-4-methylphenyl)boronic acid (1 g, 5.44 mmol) in DCM (2 mL) was cooled to 0° C. and BBr$_3$ (1.542 mL, 16.31 mmol) was added. The mixture was then stirred at rt for 2 h. It was then poured into ice and extracted with EtOAc. The organic layer was dried over MgSO$_4$, filtered and concentrated to obtain (2-fluoro-6-hydroxy-4-methylphenyl)boronic acid (650 mg, 100%) as a white solid. $^1$H NMR (400 MHz, CDCl$_3$) δ 6.89-6.58 (m, 2H), 2.48-2.33 (m, 3H).

INTERMEDIATE 28

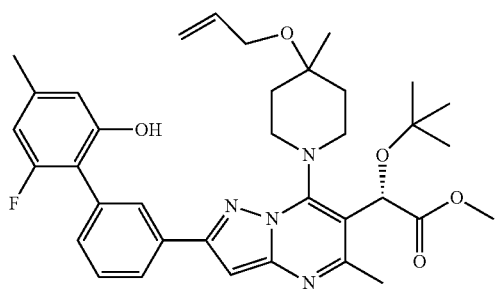 [SMILES: C=CCOC1(C)CCN(c2c([C@H](OC(C)(C)C)C(=O)OC)c(C)nc3cc(-c4cccc(-c5c(O)cc(C)cc5F)c4)nn23)CC1]

(S)-Methyl 2-(7-(4-(allyloxy)-4-methylpiperidin-1-yl)-2-(2'-fluoro-6'-hydroxy-4'-methylbiphenyl-3-yl)-5-methylpyrazolo[1,5-a]pyrimidin-6-yl)-2-tert-butoxyacetate A mixture of 3-fluoro-5-methyl-2-(4,4,5,5-tetramethyl-1,3,2-dioxaborolan-2-yl)phenol (103 mg, 0.410 mmol), (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (120 mg, 0.205 mmol) and 2M Na$_2$CO$_3$ (0.256 mL, 0.512 mmol) in DMF (1 mL)) was vacuum, back-filled with N$_2$ for 3 times. To this mixture was added Pd(Ph$_3$P)$_4$ (23.68 mg, 0.020 mmol) and heated at 95° C. in a microwave tube for 1 h. The mixture was then diluted with EtOAc, washed with water. The organic layer was dried over MgSO$_4$, filtered and concentrated to obtain 250 mg of an oil, which was then purified by biotage, eluting with 25% acetone/hexane to isolate (S)-methyl 2-(7-(4-(allyloxy)-4-methylpiperidin-1-yl)-2-(2'-fluoro-6'-hydroxy-4'-methylbiphenyl-3-yl)-5-methylpyrazolo[1,5-a]pyrimidin-6-yl)-2-tert-butoxyacetate (120 mg, 93%) as a white solid. $^1$H NMR (500 MHz, CDCl$_3$) δ 8.08 (d, J=8.2 Hz, 1H), 8.03 (s, 1H), 7.60 (t, J=7.7 Hz, 1H), 7.43 (d, J=7.4 Hz, 1H), 6.83 (s, 1H), 6.69 (s, 1H), 6.63 (d, J=9.9 Hz, 1H), 6.08-5.85 (m, 2H), 5.49-5.38 (m, 1H), 5.12 (br. s., 1H), 4.02 (d, J=4.6 Hz, 2H), 3.76 (s, 3H), 2.63 (s, 3H), 2.38 (s, 3H), 2.07-1.93 (m, 2H), 1.80-1.68 (m, 1H), 1.65-1.55 (m, 1H), 1.37 (br. s., 3H), 1.27 (s, 9H), 4 protons from piperidine were missing. LCMS (M+1)=631.6.

INTERMEDIATE 29

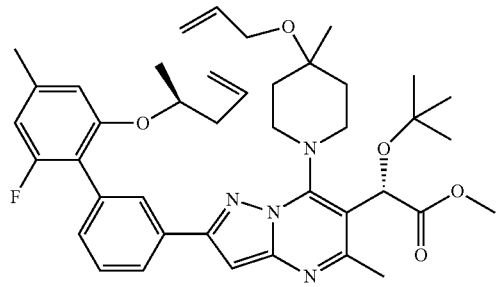 [SMILES: C=CCOC1(C)CCN(c2c([C@H](OC(C)(C)C)C(=O)OC)c(C)nc3cc(-c4cccc(-c5c(F)cc(C)cc5O[C@@H](C)CC=C)c4)nn23)CC1]

(S)-Methyl 2-(7-(4-(allyloxy)-4-methylpiperidin-1-yl)-2-(2'-fluoro-4'-methyl-6'-((S)-pent-4-en-2-yloxy)-[1,1'-biphenyl]-3-yl)-5-methylpyrazolo[1,5-a]pyrimidin-6-yl)-2-(tert-butoxy)acetate A mixture of (S)-methyl 2-(7-(4-(allyloxy)-4-methylpiperidin-1-yl)-2-(2'-fluoro-6'-hydroxy-4'-methyl-[1,1'-biphenyl]-3-yl)-5-methylpyrazolo[1,5-a]pyrimidin-6-yl)-2-(tert-butoxy)acetate (120 mg, 0.190 mmol), (R)-pent-4-en-2-ol (49.2 mg, 0.571 mmol), triphenylphosphine (150 mg, 0.571 mmol) and DEAD (99 mg, 0.571 mmol) in THF (2 mL) was stirred at rt for 3 h. It was then concentrated and diluted with EtOAc. The mixture was then washed with water. The organic layer was dried over MgSO$_4$, filtered and concentrated to obtain 120 mg of a yellow oil, which was then purified by biotage, eluting with 20% EtOAc/hexane to isolate (S)-methyl 2-(7-(4-(allyloxy)-4-methylpiperidin-1-yl)-2-(2'-fluoro-4'-methyl-6'-((S)-pent-4-en-2-yloxy)-[1,1'-biphenyl]-3-yl)-5-methylpyrazolo[1,5-a]pyrimidin-6-yl)-2-(tert-butoxy)acetate (95 mg, 57%) as an oil. LCMS (M+1)=699.3.

INTERMEDIATE 30

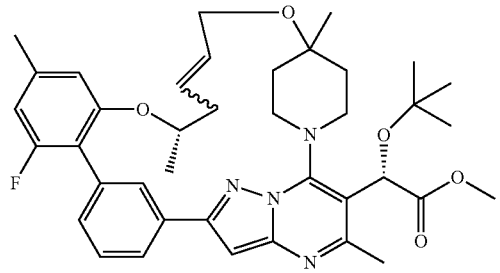 [SMILES: COC(=O)[C@@H](OC(C)(C)C)c1c(C)nc2cc3nn2c1N1CCC(C)(CC1)OCC=CC[C@H](C)Oc1cc(C)cc(F)c1-c1cccc-3c1]

Methyl (2S)-2-(tert-butoxy)-2-[(22S)-16-fluoro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate A mixture of (S)-methyl 2-(7-(4-(allyloxy)-4-methylpiperidin-1-yl)-2-(2'-fluoro-4'-methyl-6'-((S)-pent-4-en-2- yloxy)-[1,1'-biphenyl]-3-yl)-5-methylpyrazolo[1,5-a]pyrimidin-6-yl)-2-(tert-butoxy)acetate (20 mg, 0.029 mmol), (1,3-dimesitylimidazolidin-2-ylidene)(2-isopropoxybenzylidene)ruthenium(VI) chloride (1.793 mg, 2.86 μmol) and copper(I) iodide (5.45 mg, 0.029 mmol) in ClCH$_2$CH$_2$Cl (25 mL) was refluxed for 3 h. It was then concentrated to obtain 25 mg of a dark green solid. The crude material was then purified by biotage, eluting with 25% EtOAc/hexane to isolate methyl (2S)-2-(tert-butoxy)-2-[(22S,24E)-16-fluoro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (15 mg, 78%) as a white foam. The product is a mixture of cis/trans isomers. LCMS (M+1)=671.3.

EXAMPLE 4

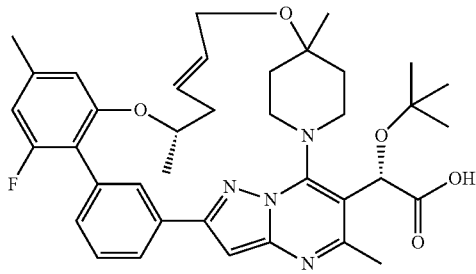 [SMILES: Cc1cc(F)c2c(c1)O[C@@H](C)C/C=C/COC1(C)CCN(CC1)c1c([C@H](OC(C)(C)C)C(=O)O)c(C)nc3cc(nn13)-c1cccc-2c1]

(2S)-2-(tert-Butoxy)-2-[(22S,24E)-16-fluoro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid A mixture of methyl (2S)-2-(tert-butoxy)-2-[(22S)-16-fluoro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (15 mg, 0.022 mmol) and 1N NaOH (0.112 mL, 0.112 mmol) in MeOH (1 mL) was refluxed for 3 h. It was then cooled to rt, filtered and purified by prep HPLC to isolate 2S)-2-(tert-butoxy)-2-[(22S)-16-fluoro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid (7 mg, 46%) as a white solid. $^1$H NMR (600 MHz, DMSO-d6) δ 8.16 (s, 1H), 7.95-7.90 (m, 1H), 7.51 (t, J=7.7 Hz, 1H), 7.24 (d, J=7.3 Hz, 1H), 7.08 (s, 1H), 6.85 (s, 1H), 6.73-6.67 (m, 1H), 6.14 (br. s., 1H), 5.81-5.70 (m, 1H), 5.64 (d, J=15.4 Hz, 1H), 4.76 (t, J=11.9 Hz, 1H), 4.61-4.49 (m, 1H), 3.97-3.90 (m, 1H), 3.88-3.79 (m, 1H), 3.52-3.48 (m, 1H), 3.27-3.21 (m, 1H), 2.78-2.69 (m, 1H), 2.52 (s, 3H), 2.36 (s, 3H), 2.30-2.21 (m, 1H), 2.16-2.06 (m, 1H), 2.01 (d, J=13.2 Hz, 1H), 1.86 (d, J=12.5 Hz, 1H), 1.70-1.54 (m, 2H), 1.21 (s, 3H), 1.17 (s, 9H), 1.07 (d, J=5.9 Hz, 3H). LCMS (M+1)=657.3.

INTERMEDIATE 31

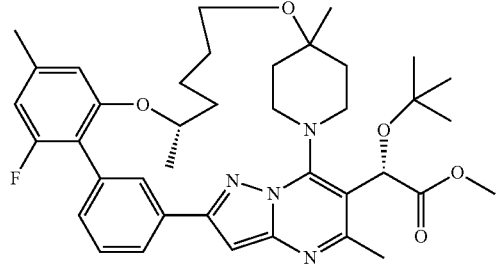 [SMILES: COC(=O)[C@@H](OC(C)(C)C)c1c(C)nc2cc3nn2c1N1CCC(C)(CC1)OCCCC[C@H](C)Oc1cc(C)cc(F)c1-c1cccc-3c1]

Methyl (2S)-2-(tert-butoxy)-2-[(22S)-16-fluoro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate To a mixture of methyl (2S)-2-(tert-butoxy)-2-[(22S)-16-fluoro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (75 mg, 0.112 mmol) and Hoveyda-Grubb catalyst (10 mg) in MeOH (2 mL) was added NaBH$_4$ (4.23 mg, 0.112 mmol) 5 times slowly during an hour. It was then stirred at rt for another hour. The mixture was then extracted with EtOAc, washed with water. The organic layer was dried over MgSO$_4$, filtered and concentrated to obtain 80 mg of an oil, which was then purified by biotage, eluting with 20% EtOAc/hexane to isolate methyl (2S)-2-(tert-butoxy)-2-[(22S)-16-fluoro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (65 mg, 86%) as a white solid. $^1$H NMR (400 MHz, CDCl$_3$) δ 8.34 (s, 1H), 7.81 (d, J=8.1 Hz, 1H), 7.49 (t, J=7.6 Hz, 1H), 7.32 (d, J=8.3 Hz, 1H), 6.89 (s, 1H), 6.68-6.56 (m, 2H), 5.94 (s, 1H), 4.67 (t, J=11.9 Hz, 1H), 4.54 (br. s., 1H), 3.76 (s, 4H), 3.51 (br. s., 1H), 3.38 (br. s., 1H), 3.20 (d, J=10.5 Hz, 1H), 2.85 (d, J=12.5 Hz, 1H), 2.60 (s, 3H), 2.41 (s, 3H), 1.97 (br. s., 3H), 1.85-1.46 (m, 7H), 1.28-1.24 (m, 12H), 1.17 (d, J=5.9 Hz, 3H). LCMS (M+1)=673.3.

EXAMPLE 5

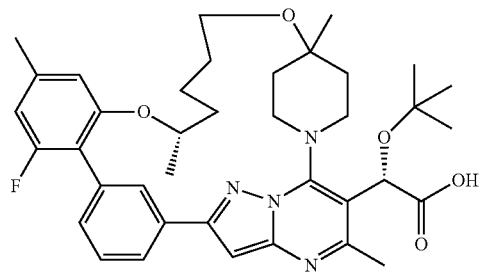 [SMILES: Cc1cc(F)c2c(c1)O[C@@H](C)CCCCOC1(C)CCN(CC1)c1c([C@H](OC(C)(C)C)C(=O)O)c(C)nc3cc(nn13)-c1cccc-2c1]

(2S)-2-(tert-Butoxy)-2-[(22S)-16-fluoro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid A mixture of methyl (2S)-2-(tert-butoxy)-2-[(22S)-16-fluoro-4,18,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate (65 mg, 0.097 mmol) and 1N NaOH (0.483 mL, 0.483 mmol) in MeOH (1 mL) was refluxed for 3 h. It was then filtered and purified by prep HPLC to obtain (2S)-2-(tert-butoxy)-2-[(22S)-16-fluoro-4,18,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl] acetic acid (30 mg, 45%) as a white solid. $^1$H NMR (400 MHz, CDCl$_3$) δ 8.37 (s, 1H), 7.81 (d, J=7.8 Hz, 1H), 7.49 (t, J=7.6 Hz, 1H), 7.34 (d, J=8.1 Hz, 1H), 6.91 (s, 1H), 6.64-6.57 (m, 2H), 6.00 (br. s., 1H), 4.80-4.65 (m, 1H), 4.55 (br. s., 1H), 3.87-3.76 (m, 1H), 3.51 (br. s., 2H), 3.38 (br. s., 1H), 2.91 (br. s., 1H), 2.59 (s, 3H), 2.41 (s, 3H), 2.12-1.50 (m, 10H), 1.30 (s, 9H), 1.26 (s, 3H), 1.17 (d, J=6.1 Hz, 3H). LCMS (M+1)=659.3.

INTERMEDIATE 32

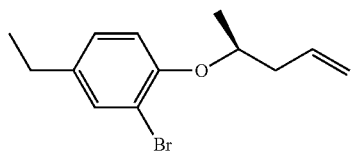

(S)-2-Bromo-4-ethyl-1-(pent-4-en-2-yloxy)benzene

A mixture of 2-bromo-4-ethylphenol (500 mg, 2.487 mmol), (R)-pent-4-en-2-ol (428 mg, 4.97 mmol), triphenylphosphine (1305 mg, 4.97 mmol) and DEAD (866 mg, 4.97 mmol) in THF (20 mL) was stirred at rt for 3 h. It was then concentrated and purified by biotage, eluting with 10% EtOAc/hexane to isolate (S)-2-bromo-4-ethyl-1-(pent-4-en-2-yloxy)benzene (500 mg, 75%) as a colorless oil. $^1$H NMR (400 MHz, CDCl$_3$) δ 7.47-7.37 (m, 1H), 7.12-7.00 (m, 1H), 6.86 (d, J=8.3 Hz, 1H), 5.93 (ddt, J=17.1, 10.0, 7.1 Hz, 1H), 5.23-5.02 (m, 2H), 4.41 (sxt, J=6.0 Hz, 1H), 2.68-2.49 (m, 3H), 2.49-2.35 (m, 1H), 1.36 (d, J=6.1 Hz, 3H), 1.23 (t, J=7.6 Hz, 3H).

INTERMEDIATE 33

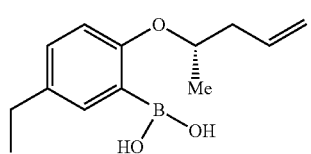 [SMILES: C=CC[C@H](C)Oc1ccc(CC)cc1B(O)O]

(S)-(5-Ethyl-2-(pent-4-en-2-yloxy)phenyl)boronic acid 2.5 M BuLi (0.178 mL, 0.446 mmol) was added to a solution of (S)-2-bromo-4-ethyl-1-(pent-4-en-2-yloxy)benzene (100 mg, 0.372 mmol) in THF (2 mL) at −78° C. After 1 h, triisopropyl borate (349 mg, 1.858 mmol) was added. The reaction was warmed to rt and stirred at rt for 16 h. The reaction was quenched with 2 N aq HCl and stirred for 20 min at rt. It was then extracted with ether. The organic phase was dried with Na$_2$SO$_4$, filtered, and concentrated in vacuo to obtain (S)-(5-ethyl-2-(pent-4-en-2-yloxy)phenyl)boronic acid as an colorless oil (90 mg, 83%). It was then used in the next step without purification.

INTERMEDIATE 34

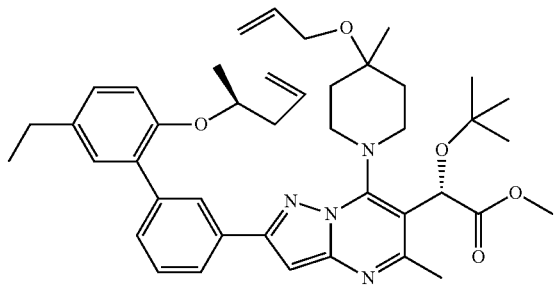 [SMILES: C=CCOC1(C)CCN(c2c([C@H](OC(C)(C)C)C(=O)OC)c(C)nc3cc(-c4cccc(-c5cc(CC)ccc5O[C@@H](C)CC=C)c4)nn23)CC1]

(S)-Methyl 2-(7-(4-(allyloxy)-4-methylpiperidin-1-yl)-2-(5'-ethyl-2'-((S)-pent-4-en-2-yloxy)-[1,1'-biphenyl]-3-yl)-5-methylpyrazolo[1,5-a]pyrimidin-6-yl)-2-(tert-butoxy)acetate A mixture of (S)-(5-ethyl-2-(pent-4-en-2-yloxy)phenyl) boronic acid (70.0 mg, 0.239 mmol), (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy) acetate (70 mg, 0.120 mmol) and 2M Na$_2$CO$_3$ (0.149 mL, 0.299 mmol) in DMF (1 mL) was vacuum, back-filled with N$_2$ for 3 times. To this mixture was added Pd(Ph$_3$P)$_4$ (13.81 mg, 0.012 mmol) and heated at 95° C. in a microwave tube for 1 h. It was then diluted with EtOAc. The mixture was washed with water. The organic layer was dried over MgSO$_4$, filtered and concentrated to obtain 100 mg of an oil, which was then purified by biotage, eluting with 25% EtOAc/hexane to isolate (S)-methyl 2-(7-(4-(allyloxy)-4-methylpiperidin-1-yl)-2-(5'-ethyl-2'-((S)-pent-4-en-2-yloxy)-[1,1'-biphenyl]-3-yl)-5-methylpyrazolo[1,5-a]pyrimidin-6-yl)-2-(tert-butoxy)acetate (68 mg, 82%) as a white solid. LCMS (M+1)=695.4.

INTERMEDIATE 35

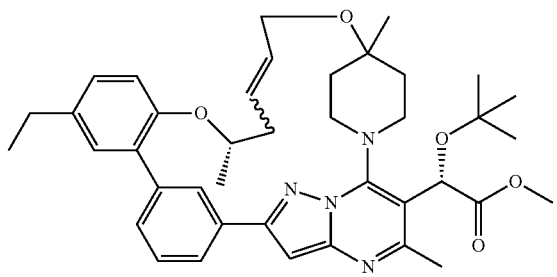 [SMILES: CCc1ccc2c(c1)-c1cccc(c1)-c1cc3nc(C)c([C@H](OC(C)(C)C)C(=O)OC)c(n3n1)N1CCC(C)(CC1)OCC=CC[C@H](C)O2]

Methyl (2S)-2-(tert-butoxy)-2-[(22S)-17-ethyl-4,22,28-trimethyl-21,27-dioxa-1,5,7,8-tetraazahexacyclo [26.2.2.1⁶,⁹.1¹⁰,¹⁴.0²,⁷.0¹⁵,²⁰]tetratriaconta-2,4,6(34), 8,10(33),11,13,15(20),16,18,24-undecaen-3-yl] acetate A mixture of (S)-methyl 2-(7-(4-(allyloxy)-4-methylpiperidin-1-yl)-2-(5'-ethyl-2'-((S)-pent-4-en-2-yloxy)-[1,1'-biphenyl]-3-yl)-5-methylpyrazolo[1,5-a]pyrimidin-6-yl)-2-(tert-butoxy)acetate (68 mg, 0.098 mmol), (1,3-dimesitylimidazolidin-2-ylidene)(2-isopropoxybenzylidene)ruthenium(VI) chloride (6.13 mg, 9.79 μmol) and copper(I) iodide (18.64 mg, 0.098 mmol) in ClCH$_2$CH$_2$Cl (90 mL) was refluxed for 3 h. It was then concentrated to obtain methyl (2S)-2-(tert-butoxy)-2-[(22S)-17-ethyl-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (60 mg, 92%) as a dark green solid. The product is a mixture of cis/trans isomers. LCMS (M+1)=667.3.

EXAMPLE 6

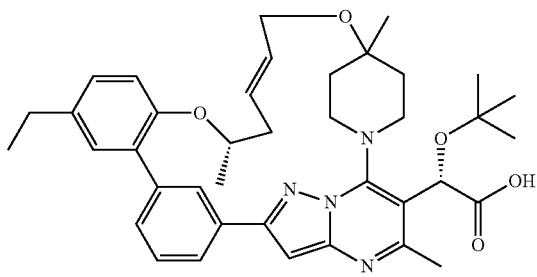 [SMILES: CCc1ccc2c(c1)-c1cccc(c1)-c1cc3nc(C)c([C@H](OC(C)(C)C)C(=O)O)c(n3n1)N1CCC(C)(CC1)OC/C=C/C[C@H](C)O2]

(2S)-2-(tert-Butoxy)-2-[(22S)-17-ethyl-4,22,28-trimethyl-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34), 8,10(33),11,13,15(20),16,18,24-undecaen-3-yl]acetic acid A mixture of methyl (2S)-2-(tert-butoxy)-2-[(22S)-17-ethyl-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (10 mg, 0.015 mmol) and 1N NaOH (0.075 mL, 0.075 mmol) in MeOH (1 mL) was refluxed for 3 h. It was then cooled to rt, filtered and purified by prep HPLC to obtain (2S)-2-(tert-butoxy)-2-[(22S)-17-ethyl-4,22,28-trimethyl-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34),8,10 (33),11,13,15(20),16,18,24-undecaen-3-yl]acetic acid (3 mg, 30.6%) as a white solid. $^1$H NMR (400 MHz, methanol-d4) δ 8.51 (s, 1H), 7.85 (d, J=7.8 Hz, 1H), 7.51 (t, J=7.7 Hz, 1H), 7.30 (d, J=7.6 Hz, 1H), 7.15 (dd, J=8.6, 2.2 Hz, 1H), 7.08 (d, J=2.2 Hz, 1H), 7.00 (d, J=8.6 Hz, 1H), 6.93 (s, 1H), 6.49-6.34 (m, 1H), 5.91 (s, 1H), 5.69 (d, J=15.4 Hz, 1H), 4.99-4.92 (m, 1H), 4.60-4.47 (m, 1H), 4.12-3.91 (m, 2H), 3.72 (t, J=11.6 Hz, 1H), 3.46 (d, J=11.2 Hz, 1H), 2.89 (d, J=11.0 Hz, 1H), 2.71-2.59 (m, 5H), 2.29 (t, J=6.2 Hz, 2H), 2.09 (d, J=13.2 Hz, 1H), 1.99-1.91 (m, 1H), 1.84-1.68 (m, 2H), 1.29 (s, 3H), 1.28-1.21 (m, 12H), 1.08 (d, J=5.9 Hz, 3H). LCMS (M+1)=653.3.

INTERMEDIATE 36

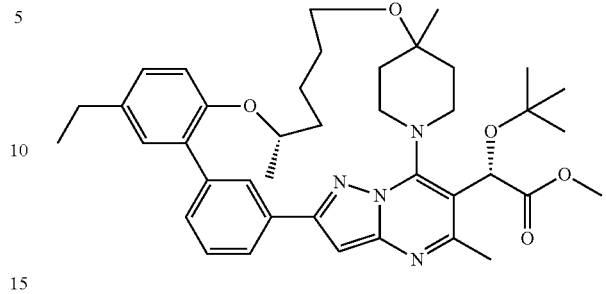

Methyl (2S)-2-(tert-butoxy)-2-[(22S)-17-ethyl-4,22, 28-trimethyl-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34), 8,10(33),11,13,15(20),16,18-decaen-3-yl]acetate To a mixture of (2S)-2-(tert-butoxy)-2-[(22S)-17-ethyl-4,22,28-trimethyl-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34),8,10 (33),11,13,15(20),16,18,24-undecaen-3-yl]acetate (75 mg, 0.112 mmol) and Hoveyda-Grubb 2$^{nd}$ catalyst (10 mg) in MeOH (2 mL) was added NaBH$_4$ (4.23 mg, 0.112 mmol) 5 times in an hour. It was then stirred at rt for another hour. The mixture was then diluted with EtOAc, washed with water. The organic layer was dried over MgSO$_4$, filtered and concentrated to obtain 80 mg of an oil, which was then purified by biotage, eluting with 20% EtOAc/hexane to isolate methyl (2S)-2-(tert-butoxy)-2-[(22S)-17-ethyl-4,22, 28-trimethyl-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34),8,10 (33),11,13,15(20),16,18-decaen-3-yl]acetate (65 mg, 86%) as a white solid. $^1$H NMR (400 MHz, CDCl$_3$) δ 8.34 (s, 1H), 7.81 (d, J=8.1 Hz, 1H), 7.49 (t, J=7.6 Hz, 1H), 7.32 (d, J=8.3 Hz, 1H), 6.89 (s, 1H), 6.68-6.56 (m, 2H), 5.94 (s, 1H), 4.67 (t, J=11.9 Hz, 1H), 4.54 (br. s., 1H), 3.76 (s, 4H), 3.51 (br. s., 1H), 3.38 (br. s., 1H), 3.20 (d, J=10.5 Hz, 1H), 2.85 (d, J=12.5 Hz, 1H), 2.60 (s, 3H), 2.41 (s, 3H), 1.97 (br. s., 3H), 1.85-1.46 (m, 7H), 1.28-1.24 (m, 12H), 1.17 (d, J=5.9 Hz, 3H). LCMS (M+1)=673.3.

EXAMPLE 7

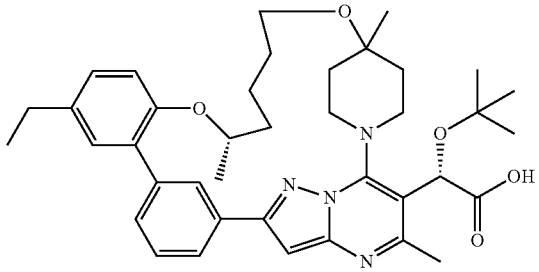 [SMILES: CCc1ccc2c(c1)-c1cccc(c1)-c1cc3nc(C)c([C@H](OC(C)(C)C)C(=O)O)c(n3n1)N1CCC(C)(CC1)OCCCC[C@H](C)O2]

(2S)-2-(tert-Butoxy)-2-[(22S)-17-ethyl-4,22,28-trimethyl-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34), 8,10(33),11,13,15(20),16,18-decaen-3-yl]acetic acid A mixture of methyl (2S)-2-(tert-butoxy)-2-[(22S)-17-ethyl-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetate (50 mg, 0.075 mmol) and 1N NaOH (0.374 mL, 0.374 mmol) in MeOH (1 mL) was refluxed for 3 h. It was then filtered and purified by prep HPLC to obtain (2S)-2-(tert-butoxy)-2-[(22S)-17-ethyl-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid (35 mg, 68%) as a white solid. $^1$H NMR (500 MHz, DMSO-d6) δ 8.45 (s, 1H), 7.84 (d, J=7.6 Hz, 1H), 7.48 (t, J=7.6 Hz, 1H), 7.28 (d, J=7.6 Hz, 1H), 7.11 (d, J=7.9 Hz, 1H), 7.06 (s, 1H), 7.01 (s, 1H), 6.98 (d, J=8.5 Hz, 1H), 5.59 (br. s., 1H), 4.53 (d, J=5.8 Hz, 1H), 4.41 (t, J=12.4 Hz, 1H), 3.52 (t, J=11.6 Hz, 1H), 3.32 (br. s., 2H), 3.23 (br. s., 1H), 2.72 (s, 1H), 2.54-2.49 (m, 2H), 2.47 (s, 3H), 1.95-1.75 (m, 3H), 1.60 (br. s., 4H), 1.51-1.32 (m, 3H), 1.15-1.06 (m, 15H), 0.99 (d, J=5.8 Hz, 3H). LCMS (M+1)=655.4.

INTERMEDIATE 37

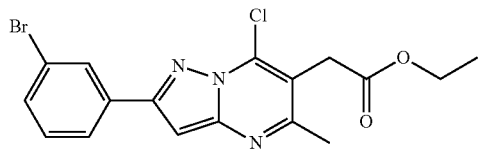 [SMILES: CCOC(=O)Cc1c(C)nc2cc(-c3cccc(Br)c3)nn2c1Cl]

Ethyl 2-(2-(3-bromophenyl)-7-chloro-5-methylpyrazolo[1,5-a]pyrimidin-6-yl)acetate Prepared according to the procedure for intermediate 4. $^1$H NMR (500 MHz, CDCl$_3$) δ 8.20 (t, J=1.7 Hz, 1H), 7.95 (qd, J=0.8, 7.8 Hz, 1H), 7.56 (ddd, J=1.0, 2.0, 8.0 Hz, 1H), 7.36 (t, J=7.9 Hz, 1H), 6.94 (s, 1H), 4.25 (q, J=7.1 Hz, 2H), 3.93 (s, 2H), 2.65 (s, 3H), 1.32 (t, J=7.1 Hz, 3H).

INTERMEDIATE 38

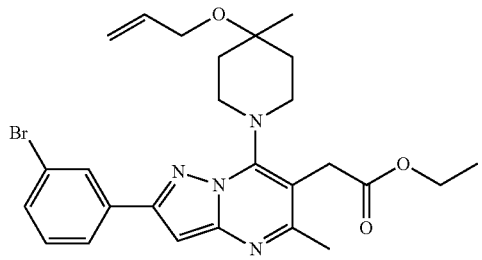 [SMILES: C=CCOC1(C)CCN(c2c(CC(=O)OCC)c(C)nc3cc(-c4cccc(Br)c4)nn23)CC1]

Ethyl 2-(7-(4-(allyloxy)-4-methylpiperidin-1-yl)-2-(3-bromophenyl)-5-methylpyrazolo[1,5-a]pyrimidin-6-yl)acetate A mixture of ethyl 2-(2-(3-bromophenyl)-7-chloro-5-methylpyrazolo[1,5-a]pyrimidin-6-yl)acetate (28 g, 68.5 mmol) in DMF (150 ml) was treated with 4-(allyloxy)-4-methylpiperidine.HCl (14.3 g, 74.6 mmol) and Hunig's Base (35.9 ml, 206 mmol), and the mixture was heated (60° C. oil bath) for 16 h. At this point LCMS indicates completion of reaction. Mixture was then cooled, diluted with Et$_2$O and washed with water (3×100 mL) and brine (100 mL), then dried (Na$_2$SO$_4$), filtered, and concentrated under reduced pressure. The residue was then purified by Biotage (5-50% EtOAc/hexane) to afford ethyl 2-(7-(4-(allyloxy)-4-methylpiperidin-1-yl)-2-(3-bromophenyl)-5-methylpyrazolo[1,5-a]pyrimidin-6-yl)acetate (32.6 g, 61.8 mmol, 90% yield) as viscous oil. $^1$H NMR (500 MHz, CDCl$_3$) δ 8.16 (t, J=1.7 Hz, 1H), 7.94 (dt, J=7.8, 1.3 Hz, 1H), 7.54-7.49 (m, 1H), 7.37-7.30 (m, 1H), 6.79 (s, 1H), 6.13-5.99 (m, 1H), 5.51-5.40 (m, 1H), 5.26 (dd, J=10.4, 1.4 Hz, 1H), 4.24 (q, J=7.1 Hz, 2H), 4.03 (dt, J=5.2, 1.6 Hz, 2H), 3.82 (br. s, 4H), 3.32 (br. s., 2H), 2.54 (s, 3H), 1.99 (d, J=13.2 Hz, 2H), 1.86 (br. s., 2H), 1.36 (s, 3H), 1.31 (t, J=7.1 Hz, 3H). LCMS (M+H)=528.8.

INTERMEDIATE 39

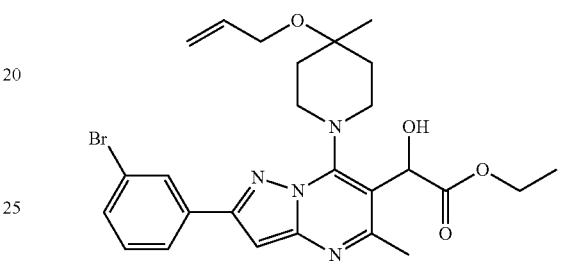

Ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate To a stirred solution of 1M KHMDS/THF (49.3 mL, 49.3 mmol) in THF (150 mL) at −78° C. was added dropwise a THF (100 mL) solution of ethyl 2-(7-(4-(allyloxy)-4-methylpiperidin-1-yl)-2-(3-bromophenyl)-5-methylpyrazolo[1, 5-a]pyrimidin-6-yl)acetate (20 g, 37.9 mmol) over 5 min. After 30 min, a THF (100 mL) solution of 3-phenyl-2-(phenylsulfonyl)-1,2-oxaziridine (12.88 g, 49.3 mmol) was added and stirred for additional 30 min at −78° C. Then, the resulting dark reaction mixture was quenched with sat. NH$_4$Cl (50 mL), diluted with EtOAc (200 mL), washed with water (100 mL), brine (100 mL), dried (Na$_2$SO$_4$), filtered and concentrated. The residue was then purified by Biotage (5-50% EtOAc/hexane) to afford ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate (17 g, 31.3 mmol, 82% yield) as white foam. Impurities were present by NMR. Used as is in the next step without further purification. $^1$H NMR (500 MHz, CDCl$_3$) δ 8.16 (t, J=1.7 Hz, 1H), 7.99-7.92 (m, 1H), 7.58-7.50 (m, 2H), 7.34 (t, J=7.9 Hz, 1H), 6.83 (s, 1H), 6.18-6.06 (m, 1H), 5.57 (d, J=5.4 Hz, 1H), 5.48 (d, J=17.0 Hz, 1H), 5.27 (d, J=10.2 Hz, 1H), 4.83 (br. s., 2H), 4.35 (dq, J=10.8, 7.1 Hz, 1H), 4.23 (dq, J=10.9, 7.1 Hz, 1H), 4.06-3.99 (m, 2H), 2.65 (s, 3H), 2.00 (d, J=14.2 Hz, 2H), 1.84 (d, J=13.4 Hz, 2H), 1.36 (s, 3H), 1.29-1.26 (m, 3H). LCMS (M+H)=545.3.

INTERMEDIATE 40

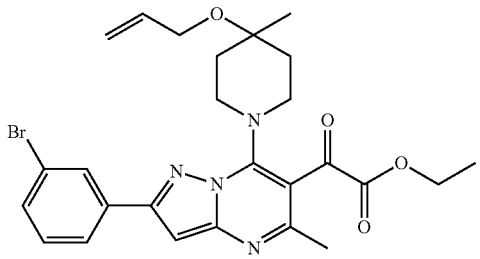 [SMILES: C=CCOC1(C)CCN(c2c(C(=O)C(=O)OCC)c(C)nc3cc(-c4cccc(Br)c4)nn23)CC1]

Ethyl 2-(7-(4-(allyloxy)-4-methylpiperidin-1-yl)-2-(3-bromophenyl)-5-methylpyrazolo[1,5-a]pyrimidin-6-yl)-2-oxoacetate To a solution of ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate (32 g, 58.9 mmol) in dry DCM (500 mL) was added Dess-Martin periodinane (24.97 g, 58.9 mmol). The resulting bright orange-red solution was stirred for 90 min. The reaction was quenched by stirring with a saturated solution of Na$_2$S$_2$O$_3$ (100 mL) and sat. NaHCO$_3$ (100 mL) for 25 min to quench any unreacted Dess-Martin reagent. The reaction mixture was poured into a reparatory funnel and organic layer separated. The aqueous layer was further extracted with EtOAc. The two organic components were separately washed with brine, then combined, dried (Na$_2$SO$_4$), filtered, and concentrated under reduced pressure. The residue was then purified via Biotage (5-40%) EtOAc/hexane to afford ethyl 2-(7-(4-(allyloxy)-4-methylpiperidin-1-yl)-2-(3-bromophenyl)-5-methylpyrazolo[1,5-a]pyrimidin-6-yl)-2-oxoacetate (22.6 g, 41.7 mmol, 70.9% yield) as off-white solid. $^1$H NMR (500 MHz, CDCl$_3$) δ 8.12 (t, J=1.7 Hz, 1H), 7.91 (dt, J=7.8, 1.3 Hz, 1H), 7.56 (ddd, J=8.0, 2.0, 0.9 Hz, 1H), 7.37 (t, J=7.9 Hz, 1H), 6.82 (s, 1H), 6.00 (ddt, J=17.2, 10.4, 5.2 Hz, 1H), 5.44-5.36 (m, 1H), 5.24-5.17 (m, 1H), 4.46-4.35 (m, 2H), 3.98 (dt, J=5.1, 1.5 Hz, 2H), 3.80-3.71 (m, 2H), 3.69-3.60 (m, 2H), 2.60 (s, 3H), 2.03-1.88 (m, 4H), 1.46-1.40 (m, 3H), 1.31 (s, 3H). LCMS (M+H)=543.3.

INTERMEDIATE 41

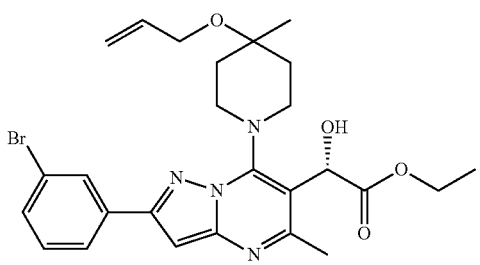 [SMILES: C=CCOC1(C)CCN(c2c([C@H](O)C(=O)OCC)c(C)nc3cc(-c4cccc(Br)c4)nn23)CC1]

(S)-Ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate To a stirred yellow solution of ethyl 2-(7-(4-(allyloxy)-4-methylpiperidin-1-yl)-2-(3-bromophenyl)-5-methylpyrazolo[1,5-a]pyrimidin-6-yl)-2-oxoacetate (22 g, 40.6 mmol) in anhydrous toluene (800 mL) was added 1M (R)-1-methyl-3,3-diphenylhexahydropyrrolo[1,2-c][1,3,2]oxazaborole/toluene (16.25 mL, 16.25 mmol). The mixture was cooled to −35° C. and catechoborane (7.11 mL, 56.9 mmol) was added over 5 min. After 30 min, the reaction mixture was slowly warmed to −15° C. and stirred for additional 2 h. A this point LCMS indicated approx 60% conversion, so mixture was cooled to −35° C. and 3.5 mL of catechoborane was added and stirred at −15° C. for 2 h. At his point LCMS indicates completion of reaction. Mixture was then diluted with EtOAc (1 L) and sat. Na$_2$CO$_3$ (300 mL). The mixture was stirred vigorously for 30 min, and the organic phase washed with sat Na$_2$CO$_3$ (2×200 mL) each time vigorously stirring for 30 min, dried (Na$_2$SO$_4$), filtered, concentrated and the residue was purified by silica gel chromatography (5-70% EtOAc/hexane) to afford desired (S)-ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate (17 g, 31.3 mmol, 77% yield) as off-white solid. $^1$H NMR (500 MHz, CDCl$_3$) δ 8.19-8.10 (m, 1H), 7.95 (d, J=7.9 Hz, 1H), 7.58-7.52 (m, 1H), 7.33 (t, J=7.8 Hz, 1H), 6.86-6.82 (m, 1H), 6.10 (dd, J=10.8, 5.1 Hz, 1H), 5.57 (d, J=5.2 Hz, 1H), 5.48 (d, J=16.9 Hz, 1H), 5.27 (d, J=10.2 Hz, 1H), 4.35 (dq, J=10.8, 7.2 Hz, 1H), 4.23 (dq, J=10.7, 7.1 Hz, 1H), 4.03 (dt, J=5.2, 1.5 Hz, 2H), 2.65 (s, 3H), 2.00 (d, J=14.5 Hz, 2H), 1.84 (br. s., 2H), 1.36 (s, 3H), 1.29-1.24 (m, 3H). LCMS (M+H)=543.4.

INTERMEDIATE 42

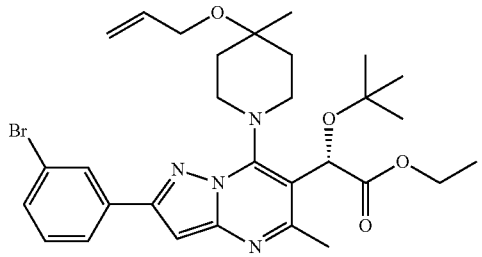 [SMILES: C=CCOC1(C)CCN(c2c([C@H](OC(C)(C)C)C(=O)OCC)c(C)nc3cc(-c4cccc(Br)c4)nn23)CC1]

(S)-Ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate To a stirred solution of (S)-ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate (8.5 g, 15.64 mmol) in DCM (250 mL) and t-butyl acetate (175 mL) was added perchloric acid (4.03 mL, 46.9 mmol) at rt. After 3 h, the reaction mixture was diluted with DCM (100 mL), carefully quenched with sat. NaHCO$_3$ (50 mL), organic layer separated and washed with brine (100 mL), dried (Na$_2$SO$_4$), filtered and concentrated to give yellow liquid. This was purified by flash column chromatography on silica gel column using (10-50% EtOAc/Hex as eluant) to afford the desired (S)-ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (5 g, 8.34 mmol, 53.3% yield) as light yellow solid. 3 g of starting material was also recovered. $^1$H NMR (500 MHz, CDCl$_3$) δ 8.23-8.11 (m, 1H), 7.94 (d, J=7.7 Hz, 1H), 7.56-7.51 (m, 1H), 7.33 (t, J=7.9 Hz, 1H), 6.81 (s, 1H), 6.10 (br. s., 1H), 6.00 (br. s., 1H), 5.49 (d, J=16.6 Hz, 1H), 5.28 (d, J=10.2 Hz, 1H), 4.30-4.14 (m, 2H), 4.10-4.00 (m, 2H), 2.65 (s, 3H), 2.09-1.85 (m, 3H), 1.74 (br. s., 1H), 1.38 (s, 3H), 1.28-1.16 (m, 12H). 4 missing piperidine hydrogens. LCMS (M+H)=601.5.

INTERMEDIATE 43

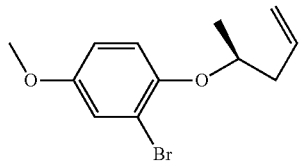

(S)-2-Bromo-4-methoxy-1-(pent-4-en-2-yloxy)benzene

A mixture of 2-bromo-4-methoxyphenol (300 mg, 1.478 mmol), (R)-pent-4-en-2-ol (255 mg, 2.96 mmol), triphenylphosphine (775 mg, 2.96 mmol) and DEAD (515 mg, 2.96 mmol) in THF (20 mL) was stirred at rt for 3 h. It was then concentrated and purified by biotage, eluting with 10% EtOAc/hexane to isolate (S)-2-bromo-4-methoxy-1-(pent-4-en-2-yloxy)benzene (300 mg, 75%) as a colorless oil. $^1$H NMR (400 MHz, CDCl$_3$) δ 7.12 (d, J=2.9 Hz, 1H), 6.93-6.87 (m, 1H), 6.84-6.78 (m, 1H), 5.92 (ddt, J=17.2, 10.2, 7.1 Hz, 1H), 5.21-5.09 (m, 2H), 4.32 (sxt, J=6.1 Hz, 1H), 3.78 (s, 3H), 2.62-2.48 (m, 1H), 2.46-2.35 (m, 1H), 1.33 (d, J=6.1 Hz, 3H).

INTERMEDIATE 44

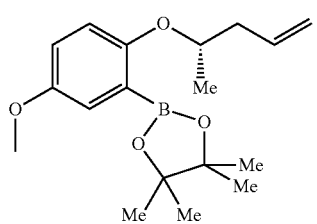 [SMILES: C=CC[C@H](C)Oc1ccc(OC)cc1B1OC(C)(C)C(C)(C)O1]

(S)-2-(5-Methoxy-2-(pent-4-en-2-yloxy)phenyl)-4,4,5,5-tetramethyl-1,3,2-dioxaborolane To a solution of (S)-2-bromo-4-methoxy-1-(pent-4-en-2-yloxy)benzene (180 mg, 0.664 mmol) in THF (2 mL) was added BuLi (0.498 mL, 0.797 mmol, 1.6 M in hexane) at −78° C. It was then stirred at this temperature for 0.5 h, 2-isopropoxy-4,4,5,5-tetramethyl-1,3,2-dioxaborolane (0.271 mL, 1.328 mmol) was added and stirred at −78° C. for 0.5 h. The reaction mixture was warmed to rt and stirred at rt for 3 h. It was then quenched with water, extracted with EtOAc. The organic layer was dried over MgSO$_4$, filtered and concentrated to obtain (S)-2-(5-methoxy-2-(pent-4-en-2-yloxy)phenyl)-4,4,5,5-tetramethyl-1,3,2-dioxaborolane (0.25 g, 50% pure, 59%) as an oil. It was then used directly in the next step.

INTERMEDIATE 45

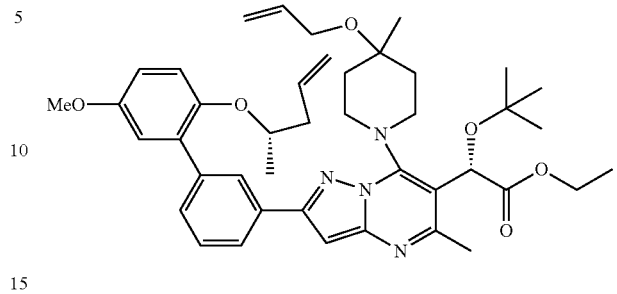

(S)-Ethyl 2-(7-(4-(allyloxy)-4-methylpiperidin-1-yl)-2-(5'-methoxy-2'-((S)-pent-4-en-2-yloxy)-[1,1'-biphenyl]-3-yl)-5-methylpyrazolo[1,5-a]pyrimidin-6-yl)-2-(tert-butoxy)acetate A mixture of (S)-2-(5-methoxy-2-(pent-4-en-2-yloxy)phenyl)-4,4,5,5-tetramethyl-1,3,2-dioxaborolane (106 mg, 0.334 mmol), (S)-ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (100 mg, 0.167 mmol) and 2 M Na$_2$CO$_3$ (0.208 mL, 0.417 mmol) in DMF (1 mL) was vacuum, back-filled with N$_2$ for 3 times. To this mixture was added Pd(Ph$_3$P)$_4$ (19.74 mg, 0.017 mmol) and heated at 95° C. in a microwave tube for 1 h. The mixture was then diluted with EtOAc, washed with water. The organic layer was dried over MgSO$_4$, filtered and concentrated to obtain an oil, which was purified by biotage, eluting with 25% acetone/hexane to isolate (S)-ethyl 2-(7-(4-(allyloxy)-4-methylpiperidin-1-yl)-2-(5'-methoxy-2'-((S)-pent-4-en-2-yloxy)-[1,1'-biphenyl]-3-yl)-5-methylpyrazolo[1,5-a]pyrimidin-6-yl)-2-(tert-butoxy)acetate (81 mg, 68%) as a white solid. LCMS (M+1)=711.4.

INTERMEDIATE 46

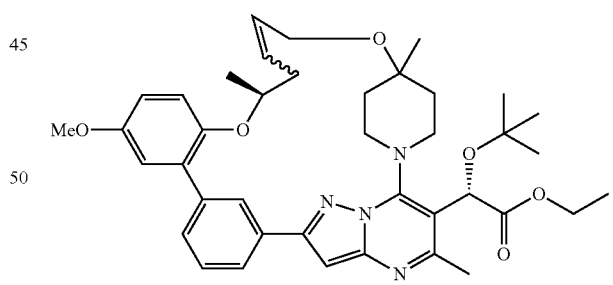

Ethyl (2S)-2-(tert-butoxy)-2-[(22S)-17-methoxy-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6 (34),8,10(33),11,13,15(20),16,18,24-undecaen-3-yl] acetate A mixture of (S)-ethyl 2-(7-(4-(allyloxy)-4-methylpiperidin-1-yl)-2-(5'-methoxy-2'-((S)-pent-4-en-2-yloxy)-[1,1'-biphenyl]-3-yl)-5-methylpyrazolo[1,5-a]pyrimidin-6-yl)-2-(tert-butoxy)acetate (80 mg, 0.113 mmol), (1,3-dimesitylimidazolidin-2-ylidene)(2- isopropoxybenzylidene)ruthenium(VI) chloride (7.05 mg, 0.011 mmol) and copper(I) iodide (21.43 mg, 0.113 mmol) in ClCH$_2$CH$_2$Cl (90 mL) was refluxed for 3 h. It was then concentrated and filtered to obtain ethyl (2S)-2-(tert-butoxy)-2-[(22S,24)-17-methoxy-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (75 mg, 98%) as a dark green solid. The product is a mixture of cis/trans isomers. LCMS (M+1)=683.3.

INTERMEDIATE 47

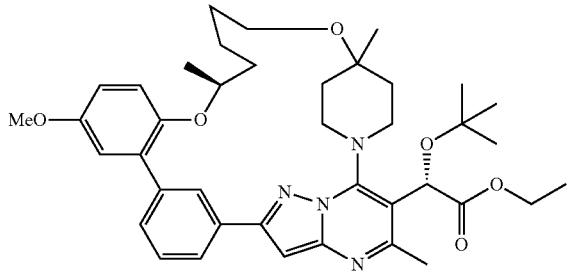 [SMILES: CCOC(=O)[C@@H](OC(C)(C)C)c1c(C)nc2cc3nn2c1N1CCC(C)(CC1)OCCCC[C@H](C)Oc1ccc(OC)cc1-c1cccc-3c1]

Ethyl (2S)-2-(tert-butoxy)-2-[(22S)-17-methoxy-4, 22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6 (34),8,10(33),11,13,15(20),16,18-decaen-3-yl] acetate To a solution of above crude ethyl (2S)-2-(tert-butoxy)-2-[(22S,24Z)-17-methoxy-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (60 mg, 0.088 mmol) in EtOH (2 mL) was added NaBH$_4$ (3.32 mg, 0.088 mmol) five times in an hour. It was then diluted with EtOAc and washed with water. The organic layer was dried over MgSO$_4$, filtered and concentrated to obtain an oil, which was then purified by biotage, eluting with 20% EtOAc/hexane to isolate ethyl (2S)-2-(tert-butoxy)-2-[(22S)-17-methoxy-4,22,28-trimethyl-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34),8,10 (33),11,13,15(20),16,18-decaen-3-yl]acetate (50 mg, 83%) as a white foam. $^1$H NMR (400 MHz, CDCl$_3$) δ 8.58 (s, 1H), 7.80 (d, J=8.1 Hz, 1H), 7.51 (t, J=7.7 Hz, 1H), 7.37 (d, J=7.8 Hz, 1H), 6.97-6.85 (m, 4H), 5.91 (s, 1H), 4.68-4.56 (m, 1H), 4.52-4.43 (m, 1H), 4.29-4.18 (m, 2H), 3.84 (s, 3H), 3.83-3.74 (m, 1H), 3.49 (d, J=7.1 Hz, 1H), 3.40 (br. s., 1H), 3.28 (d, J=13.0 Hz, 1H), 2.90 (d, J=12.0 Hz, 1H), 2.62 (s, 3H), 1.99 (t, J=10.5 Hz, 3H), 1.87-1.47 (m, 7H), 1.28-1.22 (m, 15H), 1.14 (d, J=6.1 Hz, 3H). LCMS (M+1)=685.3.

EXAMPLE 8

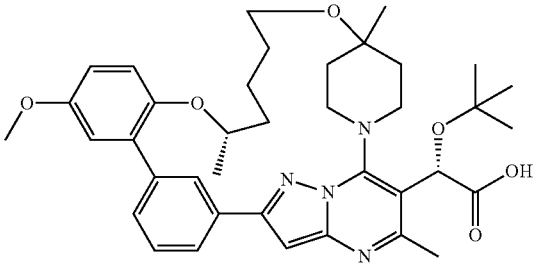 [SMILES: COc1ccc2c(c1)-c1cccc(c1)-c1cc3nc(C)c([C@H](OC(C)(C)C)C(=O)O)c(n3n1)N1CCC(C)(CC1)OCCCCC[C@H](C)O2]

(2S)-2-(tert-Butoxy)-2-[(22S)-17-methoxy-4,22,28-trimethyl-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34), 8,10(33),11,13,15(20),16,18-decaen-3-yl]acetic acid A mixture of ethyl (2S)-2-(tert-butoxy)-2-[(22S)-17-methoxy-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetate (50 mg, 0.073 mmol) and 1N NaOH (0.730 mL, 0.730 mmol) in MeOH (2 mL) was refluxed for 3 h. It was then cooled to rt and purified by prep HPLC to obtain (2S)-2-(tert-butoxy)-2-[(22S)-17-methoxy-4,22,28-trimethyl-21,27-dioxa-1,5,7, 8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl] acetic acid (30 mg, 59%) as a white solid. $^1$H NMR (400 MHz, CDCl$_3$) δ 8.62 (s, 1H), 7.80 (d, J=7.8 Hz, 1H), 7.51 (t, J=7.7 Hz, 1H), 7.38 (d, J=7.6 Hz, 1H), 6.98-6.84 (m, 4H), 5.97 (br. s., 1H), 4.67 (t, J=12.2 Hz, 1H), 4.51-4.39 (m, 1H), 3.88-3.77 (m, 4H), 3.59-3.45 (m, 2H), 3.39 (d, J=4.6 Hz, 1H), 2.95 (d, J=11.2 Hz, 1H), 2.59 (s, 3H), 2.04 (d, J=6.1 Hz, 3H), 1.84-1.44 (m, 7H), 1.31-1.24 (m, 12H), 1.14 (d, J=6.1 Hz, 3H). LCMS (M+1)=657.3.

INTERMEDIATE 48

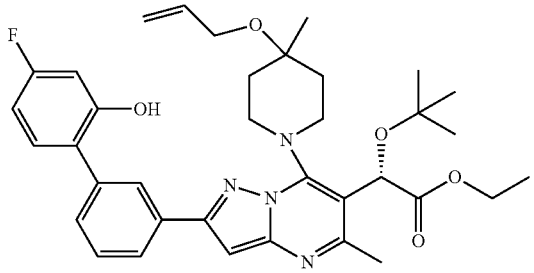 [SMILES: C=CCOC1(C)CCN(c2c([C@H](OC(C)(C)C)C(=O)OCC)c(C)nc3cc(-c4cccc(-c5ccc(F)cc5O)c4)nn23)CC1]

(S)-Ethyl 2-(7-(4-(allyloxy)-4-methylpiperidin-1-yl)-2-(4'-fluoro-2'-hydroxy-[1,1'-biphenyl]-3-yl)-5-methylpyrazolo[1,5-a]pyrimidin-6-yl)-2-(tert-butoxy) acetate A mixture of (S)-ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (200 mg, 0.334 mmol), (4-fluoro-2-hydroxyphenyl)boronic acid (62.4 mg, 0.400 mmol) and 2M Na$_2$CO$_3$ (0.417 mL, 0.834 mmol) in DMF (3 mL) was vacuum, back-filled with $N_2$ for 3 times. To this was then added $Pd(Ph_3P)_4$ (38.5 mg, 0.033 mmol) and heated at 90° C. for 3 h. The mixture was then diluted with EtOAc, washed with water. The organic layer was dried over $MgSO_4$, filtered and concentrated to obtain 200 mg of an oil, which was then purified by biotage, eluting with 25% acetone/hexane to isolate (S)-ethyl 2-(7-(4-(allyloxy)-4-methylpiperidin-1-yl)-2-(4'-fluoro-2'-hydroxy-[1,1'-biphenyl]-3-yl)-5-methylpyrazolo[1,5-a]pyrimidin-6-yl)-2-(tert-butoxy)acetate (140 mg, 66%) as a white solid. $^1$H NMR (400 MHz, $CDCl_3$) δ 8.08 (s, 1H), 8.05 (d, J=7.8 Hz, 1H), 7.59 (t, J=7.8 Hz, 1H), 7.45 (d, J=7.6 Hz, 1H), 7.33-7.26 (m, 1H), 6.85 (s, 1H), 6.80-6.77 (m, 1H), 6.76 (s, 1H), 6.14-5.90 (m, 2H), 5.74 (s, 1H), 5.40 (dd, J=17.1, 1.7 Hz, 1H), 5.10 (br. s., 1H), 4.34-4.13 (m, 2H), 4.02 (d, J=4.6 Hz, 2H), 2.64 (s, 3H), 2.12-1.89 (m, 2H), 1.74 (br. s., 1H), 1.62-1.58 (m, 1H), 1.37 (br. s., 3H), 1.29-1.20 (m, 12H), 4 protons from piperidine were missing. LCMS (M+1)=631.1.

INTERMEDIATE 49

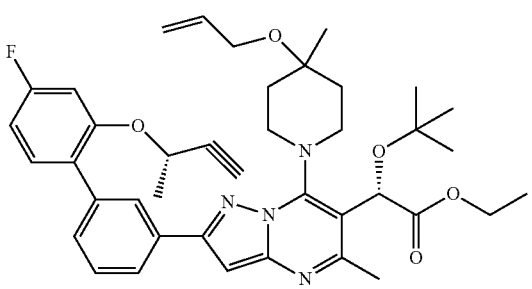 [SMILES: C#C[C@H](C)Oc1cc(F)ccc1-c1cccc(-c2cc3nc(C)c([C@H](OC(C)(C)C)C(=O)OCC)c(N4CCC(C)(OCC=C)CC4)n3n2)c1]

(S)-Ethyl 2-(7-(4-(allyloxy)-4-methylpiperidin-1-yl)-2-(2'-((S)-but-3-yn-2-yloxy)-4'-fluoro-[1,1'-biphenyl]-3-yl)-5-methylpyrazolo[1,5-a]pyrimidin-6-yl)-2-(tert-butoxy)acetate To a mixture of (S)-ethyl 2-(7-(4-(allyloxy)-4-methylpiperidin-1-yl)-2-(4'-fluoro-2'-hydroxy-[1,1'-biphenyl]-3-yl)-5-methylpyrazolo[1,5-a]pyrimidin-6-yl)-2-(tert-butoxy)acetate (240 mg, 0.381 mmol), (R)-but-3-yn-2-ol (53.3 mg, 0.761 mmol) and triphenylphosphine (200 mg, 0.761 mmol) at 0° C. in toluene (5 mL) was added DEAD (0.120 mL, 0.761 mmol). The mixture was stirred at rt for 3 h. It was then concentrated and purified by biotage, eluting with 25% EtOAc/hexane to isolate (S)-ethyl 2-(7-(4-(allyloxy)-4-methylpiperidin-1-yl)-2-(2'-((S)-but-3-yn-2-yloxy)-4'-fluoro-[1,1'-biphenyl]-3-yl)-5-methylpyrazolo[1,5-a]pyrimidin-6-yl)-2-(tert-butoxy)acetate (190 mg, 73%) as an off white solid. $^1$H NMR (400 MHz, $CDCl_3$) δ 8.13 (s, 1H), 8.05 (d, J=6.6 Hz, 1H), 7.58-7.47 (m, 2H), 7.39 (dd, J=8.3, 6.8 Hz, 1H), 7.00 (dd, J=10.8, 2.4 Hz, 1H), 6.89-6.79 (m, 2H), 6.16-5.83 (m, 2H), 5.43 (d, J=17.6 Hz, 1H), 5.14 (d, J=9.3 Hz, 1H), 4.88-4.76 (m, 1H), 4.29-4.15 (m, 2H), 4.02 (d, J=4.6 Hz, 2H), 2.64 (s, 3H), 2.53 (d, J=2.0 Hz, 1H), 2.08-1.91 (m, 3H), 1.75 (br. s., 1H), 1.41-1.35 (m, 3H), 1.28-1.21 (m, 15H), 4 protons from piperidine were missing. LCMS (M+1)=683.3.

INTERMEDIATE 50

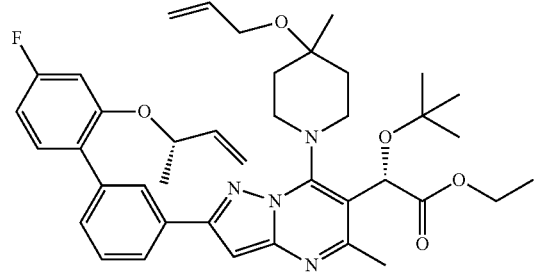 [SMILES: C=CCOC1(C)CCN(c2c([C@H](OC(C)(C)C)C(=O)OCC)c(C)nc3cc(-c4cccc(-c5ccc(F)cc5O[C@@H](C)C=C)c4)nn23)CC1]

(S)-Ethyl 2-(7-(4-(allyloxy)-4-methylpiperidin-1-yl)-2-(2'-((S)-but-3-en-2-yloxy)-4'-fluoro-[1,1'-biphenyl]-3-yl)-5-methylpyrazolo[1,5-a]pyrimidin-6-yl)-2-(tert-butoxy)acetate A mixture of chloro[1,3-bis(2,6-diisopropylphenyl)imidazol-2-ylidene]copper(I) (6.78 mg, 0.014 mmol), sodium tert-butoxide (1.337 mg, 0.014 mmol) in THF (2 mL) was stirred at rt for 0.5 h. It was then added to a mixture of (S)-ethyl 2-(7-(4-(allyloxy)-4-methylpiperidin-1-yl)-2-(2'-((S)-but-3-yn-2-yloxy)-4'-fluoro-[1,1'-biphenyl]-3-yl)-5-methylpyrazolo[1,5-a]pyrimidin-6-yl)-2-(tert-butoxy)acetate (190 mg, 0.278 mmol), polymethylhydrosiloxane (0.01 mL, 0.557 mmol) and 2-methyl-1-propanol (0.031 mL, 0.334 mmol) in toluene (2 mL). The mixture was stirred at rt for 1 h. It was then diluted with EtOAc, washed with water. The organic layer was dried over $MgSO_4$, filtered and concentrated to obtain 250 mg of an oil, which was then purified by biotage, eluting with 20% EtOAc/hexane to isolate (S)-ethyl 2-(7-(4-(allyloxy)-4-methylpiperidin-1-yl)-2-(2'-((S)-but-3-en-2-yloxy)-4'-fluoro-[1,1'-biphenyl]-3-yl)-5-methylpyrazolo[1,5-a]pyrimidin-6-yl)-2-(tert-butoxy)acetate (140 mg, 73.5%) as an off-white solid. $^1$H NMR (400 MHz, $CDCl_3$) δ 8.14 (s, 1H), 8.04 (d, J=7.0 Hz, 1H), 7.58-7.45 (m, 2H), 7.40-7.33 (m, 1H), 6.84 (s, 1H), 6.81-6.73 (m, 2H), 6.14-5.93 (m, 2H), 5.88 (ddd, J=17.1, 10.7, 6.0 Hz, 1H), 5.43 (d, J=18.6 Hz, 1H), 5.26 (d, J=17.3 Hz, 1H), 5.19-5.08 (m, 2H), 4.77 (t, J=6.3 Hz, 1H), 4.29-4.13 (m, 2H), 4.02 (d, J=4.3 Hz, 2H), 2.64 (s, 3H), 2.10-1.93 (m, 2H), 1.74 (br. s., 1H), 1.65-1.52 (m, 1H), 1.40 (d, J=6.5 Hz, 3H), 1.29-1.21 (m, 15H), 4 protons from piperidine were missing. LCMS (M+1)=685.2.

INTERMEDIATE 51

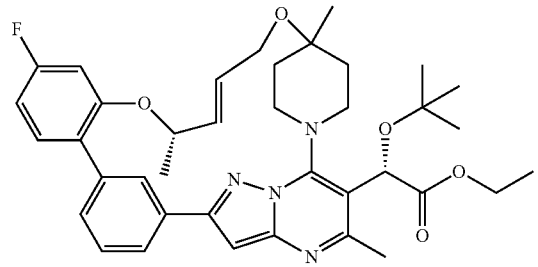 [SMILES: CCOC(=O)[C@@H](OC(C)(C)C)c1c(C)nc2cc3nn2c1N1CCC(C)(CC1)OC/C=C/[C@H](C)Oc1cc(F)ccc1-c1cccc-3c1]

Ethyl (2S)-2-(tert-butoxy)-2-[(23E)-18-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate A mixture of (S)-ethyl 2-(7-(4-(allyloxy)-4-methylpiperidin-1-yl)-2-(2'-((S)-but-3-en-2-yloxy)-4'-fluoro-[1,1'-biphenyl]-3-yl)-5-methylpyrazolo[1,5-a]pyrimidin-6-yl)-2-(tert-butoxy)acetate (130 mg, 0.190 mmol), Grubbs catalyst 2nd generation (16.12 mg, 0.019 mmol) and copper(I) iodide (36.2 mg, 0.190 mmol) in ClCH$_2$CH$_2$Cl (150 mL) was refluxed for 2 h. It was then concentrated and purified by biotage, eluting with 20% EtOAc/hexane to isolate ethyl (2S)-2-(tert-butoxy)-2-[(23E)-18-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate (120 mg, 96%) as a white solid. $^1$H NMR (400 MHz, CDCl$_3$) δ 8.59 (s, 1H), 7.78 (d, J=7.6 Hz, 1H), 7.55-7.47 (m, 1H), 7.36 (d, J=7.6 Hz, 1H), 7.28-7.22 (m, 1H), 6.90 (s, 1H), 6.80-6.67 (m, 2H), 6.27 (dd, J=15.6, 7.1 Hz, 1H), 6.05 (s, 1H), 6.04-5.92 (m, 1H), 5.11-4.89 (m, 1H), 4.76 (t, J=11.5 Hz, 1H), 4.33-4.16 (m, 2H), 4.11-4.02 (m, 1H), 4.02-3.91 (m, 2H), 3.18 (d, J=12.2 Hz, 1H), 2.74 (d, J=9.5 Hz, 1H), 2.65 (s, 3H), 2.05-1.89 (m, 2H), 1.76 (td, J=13.1, 4.6 Hz, 1H), 1.71-1.64 (m, 1H), 1.37-1.31 (m, 6H), 1.28-1.21 (m, 12H). LCMS (M+1)=657.2.

EXAMPLE 9

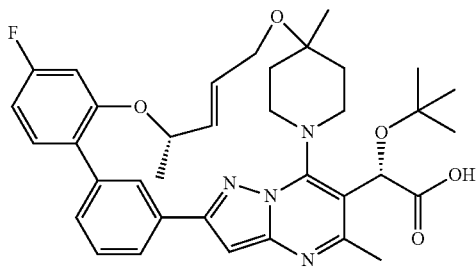 [SMILES: Cc1nc2cc3nn2c(c1[C@H](OC(C)(C)C)C(=O)O)N1CCC(C)(CC1)OC/C=C/[C@H](C)Oc1cc(F)ccc1-c1cccc-3c1]

(2S)-2-(tert-Butoxy)-2-[(23E)-18-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid A mixture of ethyl (2S)-2-(tert-butoxy)-2-[(23E)-18-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate (70 mg, 0.107 mmol) and 1N NaOH (0.533 mL, 0.533 mmol) in MeOH (2 mL) was refluxed for 3 h. It was then concentrated and purified by C18 column, eluting with 85-100% acetonitrile/water to isolate (2S)-2-(tert-butoxy)-2-[(23E)-18-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl] acetic acid (60 mg, 85%) as a white solid. $^1$H NMR (400 MHz, CDCl$_3$) δ 8.63 (br. s., 1H), 7.78 (d, J=7.3 Hz, 1H), 7.52 (t, J=7.7 Hz, 1H), 7.38 (d, J=7.5 Hz, 1H), 7.26 (br. s., 1H), 6.93 (s, 1H), 6.81-6.60 (m, 2H), 6.28 (dd, J=15.3, 7.3 Hz, 1H), 6.14-5.89 (m, 2H), 5.07-4.93 (m, 1H), 4.84 (t, J=11.7 Hz, 1H), 4.13-3.92 (m, 3H), 3.37 (d, J=8.8 Hz, 1H), 2.76 (d, J=12.0 Hz, 1H), 2.63 (s, 3H), 1.99 (t, J=10.9 Hz, 2H), 1.77-1.52 (m, 2H), 1.32 (s, 15H). LCMS (M+1)=629.2.

INTERMEDIATE 52

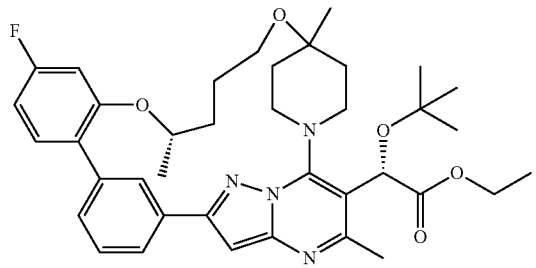 [SMILES: CCOC(=O)[C@@H](OC(C)(C)C)c1c(C)nc2cc3nn2c1N1CCC(C)(CC1)OCCC[C@H](C)Oc1cc(F)ccc1-c1cccc-3c1]

Ethyl (2S)-2-(tert-butoxy)-2-[(22S)-18-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetate To a mixture of ethyl (2S)-2-(tert-butoxy)-2-[(23E)-18-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate (50 mg, 0.076 mmol) and Grubbs II catalyst (6.46 mg, 7.61 µmol) in EtOH (2 mL) was added sodium borohydride (14.40 mg, 0.381 mmol) and stirred at rt for 1 h. It was then diluted with EtOAc, washed with water. The organic layer was dried over MgSO$_4$, filtered and concentrated to obtain 50 mg of an oil, which was then purified by biotage, eluting with 20% EtOAc/hexane to isolate ethyl (2S)-2-(tert-butoxy)-2-[(22S)-18-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetate (30 mg, 59.8%) as an off-white solid. $^1$H NMR (400 MHz, CDCl$_3$) δ 8.49 (s, 1H), 7.77 (d, J=7.8 Hz, 1H), 7.54-7.47 (m, 1H), 7.36-7.32 (m, 2H), 6.88 (s, 1H), 6.81-6.69 (m, 2H), 6.06 (s, 1H), 4.68-4.55 (m, 1H), 4.48 (t, J=9.5 Hz, 1H), 4.29-4.14 (m, 2H), 3.83 (t, J=11.2 Hz, 1H), 3.46 (t, J=5.4 Hz, 2H), 3.15 (d, J=11.0 Hz, 1H), 2.82 (d, J=11.7 Hz, 1H), 2.65 (s, 3H), 2.41-2.22 (m, 1H), 2.04-1.90 (m, 3H), 1.83-1.62 (m, 4H), 1.31-1.22 (m, 18H). LCMS (M+1)=659.2.

EXAMPLE 10

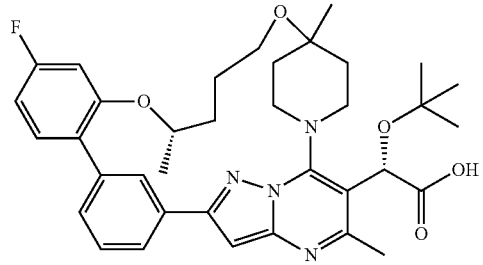 [SMILES: Cc1nc2cc3nn2c(c1[C@H](OC(C)(C)C)C(=O)O)N1CCC(C)(CC1)OCCC[C@H](C)Oc1cc(F)ccc1-c1cccc-3c1]

(2S)-2-(tert-Butoxy)-2-[(22S)-18-fluoro-4,22,27-trimethyl-21,26-dioxa-1,5,7,8-tetraazahexacyclo[25.2.2.1⁶,⁹.1¹⁰,¹⁴.0²,⁷.0¹⁵,²⁰]tritriaconta-2,4,6(33),8,10(32),11,13,15(20),16,18-decaen-3-yl]acetic acid A mixture of ethyl (2S)-2-(tert-butoxy)-2-[(22S)-18-fluoro-4,22,27-trimethyl-21,26-dioxa-1,5,7,8-tetraazahexacyclo[25.2.2.1⁶,⁹.1¹⁰,¹⁴.0²,⁷.0¹⁵,²⁰]tritriaconta-2,4,6(33),8,10(32),11,13,15(20),16,18-decaen-3-yl]acetate (27 mg, 0.041 mmol) and 1N NaOH (0.205 mL, 0.205 mmol) in MeOH (2 mL) was refluxed for 3 h. It was then concentrated and purified by C18 column, eluted with 50-100% CH₃CN/water to obtain (2S)-2-(tert-butoxy)-2-[(22S)-18-fluoro-4,22,27-trimethyl-21,26-dioxa-1,5,7,8-tetraazahexacyclo[25.2.2.1⁶,⁹.1¹⁰,¹⁴.0²,⁷.0¹⁵,²⁰]tritriaconta-2,4,6(33),8,10(32),11,13,15(20),16,18-decaen-3-yl]acetic acid (20 mg, 73.5%) as a white solid. ¹H NMR (400 MHz, CDCl₃) δ 8.52 (s, 1H), 7.77 (d, J=7.6 Hz, 1H), 7.52 (t, J=7.7 Hz, 1H), 7.39-7.31 (m, 2H), 6.91 (s, 1H), 6.81-6.69 (m, 2H), 6.06 (br. s., 1H), 4.68 (t, J=12.0 Hz, 1H), 4.48 (br. s., 1H), 3.84 (t, J=11.5 Hz, 1H), 3.46 (t, J=4.9 Hz, 2H), 3.37 (d, J=10.8 Hz, 1H), 2.84 (d, J=11.2 Hz, 1H), 2.62 (s, 3H), 2.41-2.23 (m, 1H), 2.05-1.92 (m, 3H), 1.78-1.48 (m, 4H), 1.39-1.25 (m, 15H). LCMS (M+1)=631.1.

INTERMEDIATE 53

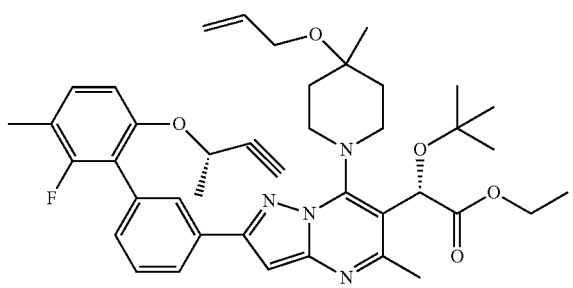 [SMILES: C#C[C@H](C)Oc1ccc(C)c(F)c1-c1cccc(-c2cc3nc(C)c([C@H](OC(C)(C)C)C(=O)OCC)c(N4CCC(C)(OCC=C)CC4)n3n2)c1]

(S)-Ethyl 2-(7-(4-(allyloxy)-4-methylpiperidin-1-yl)-2-(2'-((S)-but-3-yn-2-yloxy)-4'-fluoro-[1,1'-biphenyl]-3-yl)-5-methylpyrazolo[1,5-a]pyrimidin-6-yl)-2-(tert-butoxy)acetate To a mixture of (S)-ethyl 2-(7-(4-(allyloxy)-4-methylpiperidin-1-yl)-2-(2'-fluoro-6'-hydroxy-3'-methyl-[1,1'-biphenyl]-3-yl)-5-methylpyrazolo[1,5-a]pyrimidin-6-yl)-2-(tert-butoxy)acetate (150 mg, 0.233 mmol), (R)-but-3-yn-2-ol (32.6 mg, 0.465 mmol) and triphenylphosphine (122 mg, 0.465 mmol) at 0° C. in toluene (2 mL) was added DEAD (0.074 mL, 0.465 mmol) and the mixture was stirred at rt for 3 h. It was then concentrated and purified by biotage, eluting with 20% EtOAc/hexane to isolate (S)-ethyl 2-(7-(4-(allyloxy)-4-methylpiperidin-1-yl)-2-(2'-((S)-but-3-yn-2-yloxy)-4'-fluoro-[1,1'-biphenyl]-3-yl)-5-methylpyrazolo[1,5-a]pyrimidin-6-yl)-2-(tert-butoxy)acetate (150 mg, 93%) as an off white solid. ¹H NMR (400 MHz, CDCl₃) δ 8.12-8.02 (m, 2H), 7.53-7.43 (m, 2H), 7.16 (t, J=8.6 Hz, 1H), 6.96 (d, J=8.6 Hz, 1H), 6.84 (s, 1H), 6.14-5.84 (m, 2H), 5.42 (d, J=15.7 Hz, 1H), 5.13 (d, J=9.5 Hz, 1H), 4.75 (qd, J=6.6, 2.1 Hz, 1H), 4.27-4.15 (m, 2H), 4.02 (d, J=5.1 Hz, 2H), 2.63 (s, 3H), 2.47 (d, J=2.2 Hz, 1H), 2.30 (d, J=1.7 Hz, 3H), 2.09-1.93 (m, 2H), 1.74 (br. s., 1H), 1.58 (s, 1H), 1.48 (d, J=6.6 Hz, 3H), 1.38 (br. s., 3H), 1.28-1.21 (m, 12H), 4 protons from piperidine were missing. LCMS (M+1)=697.3.

INTERMEDIATE 54

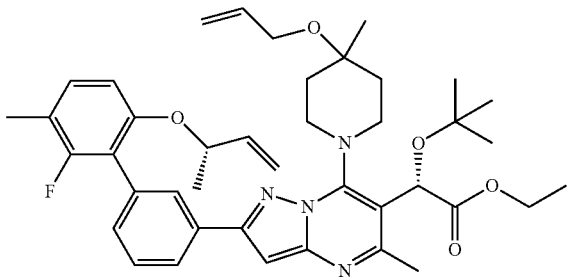 [SMILES: C=CCOC1(C)CCN(c2c([C@H](OC(C)(C)C)C(=O)OCC)c(C)nc3cc(-c4cccc(-c5c(O[C@@H](C)C=C)ccc(C)c5F)c4)nn23)CC1]

(S)-Ethyl 2-(7-(4-(allyloxy)-4-methylpiperidin-1-yl)-2-(6'-((S)-but-3-en-2-yloxy)-2'-fluoro-3'-methyl-[1,1'-biphenyl]-3-yl)-5-methylpyrazolo[1,5-a]pyrimidin-6-yl)-2-(tert-butoxy)acetate A mixture of chloro[1,3-bis(2,6-diisopropylphenyl)imidazol-2-ylidene]copper(I)(5.36 mg, 10.98 μmol) and sodium tert-butoxide (1.056 mg, 10.98 μmol) in THF (4 mL) was stirred at rt for 0.5 h. It was then added to a mixture of (S)-ethyl 2-(7-(4-(allyloxy)-4-methylpiperidin-1-yl)-2-(2'-((S)-but-3-yn-2-yloxy)-5'-fluoro-[1,1'-biphenyl]-3-yl)-5-methylpyrazolo[1,5-a]pyrimidin-6-yl)-2-(tert-butoxy)acetate (150 mg, 0.220 mmol), polymethylhydrosiloxane (26.4 mg, 0.439 mmol) and 2-methyl-1-propanol (0.024 mL, 0.264 mmol) in toluene (40 mL). The mixture was stirred at rt for 1 h. It was then diluted with EtOAc, washed with water. The organic layer was dried over MgSO₄, filtered and concentrated to obtain 200 mg of a brown oil, which was then purified by biotage, eluting with 20% EtOAc/hexane to isolate (S)-ethyl 2-(7-(4-(allyloxy)-4-methylpiperidin-1-yl)-2-(6'-((S)-but-3-en-2-yloxy)-2'-fluoro-3'-methyl-[1,1'-biphenyl]-3-yl)-5-methylpyrazolo[1,5-a]pyrimidin-6-yl)-2-(tert-butoxy)acetate (140 mg, 93%) as an off-white solid. ¹H NMR (400 MHz, CDCl₃) δ 8.19 (s, 1H), 8.06 (d, J=8.3 Hz, 1H), 7.61-7.55 (m, 1H), 7.54-7.48 (m, 1H), 7.18-7.13 (m, 1H), 7.00-6.95 (m, 2H), 6.85 (s, 1H), 6.18-5.92 (m, 2H), 5.83 (ddd, J=17.1, 10.6, 6.2 Hz, 1H), 5.42 (d, J=17.1 Hz, 1H), 5.22-5.05 (m, 3H), 4.62 (quin, J=6.4 Hz, 1H), 4.28-4.17 (m, 2H), 4.03 (d, J=5.1 Hz, 2H), 2.64 (s, 3H), 2.13-1.94 (m, 2H), 1.74 (br. s., 1H), 1.61-1.51 (m, 1H), 1.39 (br. s., 3H), 1.33 (d, J=6.4 Hz, 3H), 1.28-1.22 (m, 12H), 4 protons from piperidine were missing. LCMS (M+1)=685.6.

INTERMEDIATE 55

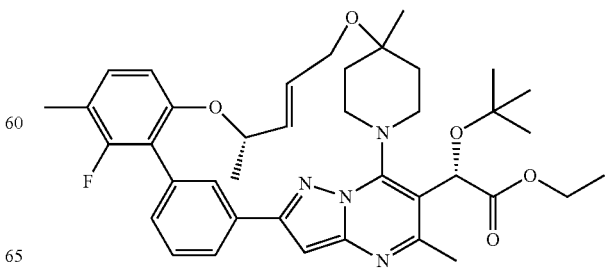

Ethyl (2S)-2-(tert-butoxy)-2-[(22S,23E)-16-fluoro-4, 17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2, 4,6(33),8,10(32),11,13,15(20),16,18,23-undecaen-3-yl]acetate A mixture of Grubbs catalyst 2nd generation (13.48 mg, 0.016 mmol), copper(I) iodide (30.2 mg, 0.159 mmol) and (S)-ethyl 2-(7-(4-(allyloxy)-4-methylpiperidin-1-yl)-2-(6'-((S)-but-3-en-2-yloxy)-2'-fluoro-3'-methyl-[1,1'-biphenyl]-3-yl)-5-methylpyrazolo[1,5-a]pyrimidin-6-yl)-2-(tert-butoxy)acetate (111 mg, 0.159 mmol) in ClCH$_2$CH$_2$Cl (120 mL) was refluxed for 2 h. It was then concentrated and purify by biotage, eluting with 20% EtOAc/hexane to isolate ethyl (2S)-2-(tert-butoxy)-2-[(22S,23E)-16-fluoro-4,17,22, 27-tetramethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8,10(32), 11,13,15(20),16,18,23-undecaen-3-yl]acetate (100 mg, 94%) as an off-white solid. $^1$H NMR (400 MHz, CDCl$_3$) δ 8.42 (s, 1H), 7.80 (d, J=7.8 Hz, 1H), 7.52 (t, J=7.6 Hz, 1H), 7.42 (d, J=7.1 Hz, 1H), 7.08 (t, J=8.6 Hz, 1H), 6.90 (s, 1H), 6.72 (d, J=8.3 Hz, 1H), 6.19 (dd, J=15.6, 7.3 Hz, 1H), 6.07 (s, 1H), 5.97-5.87 (m, 1H), 5.00 (t, J=6.8 Hz, 1H), 4.79 (t, J=11.5 Hz, 1H), 4.27-4.14 (m, 2H), 4.07-3.87 (m, 3H), 3.14 (d, J=12.0 Hz, 1H), 2.72 (d, J=11.7 Hz, 1H), 2.65 (s, 3H), 2.26 (d, J=1.7 Hz, 3H), 1.99 (d, J=11.7 Hz, 1H), 1.91 (d, J=13.4 Hz, 1H), 1.75 (td, J=13.0, 4.8 Hz, 1H), 1.70-1.61 (m, 1H), 1.32-1.22 (m, 18H). LCMS (M+1)=671.2.

EXAMPLE 11

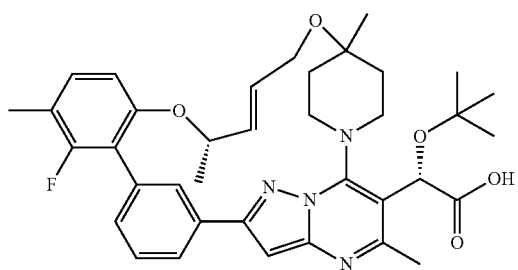 [SMILES: Cc1ccc2c(c1F)-c1cccc(c1)-c1cc3nc(C)c([C@H](OC(C)(C)C)C(=O)O)c(n3n1)N1CCC(C)(CC1)OC/C=C/[C@H](C)O2]

(2S)-2-(tert-Butoxy)-2-[(22S,23E)-16-fluoro-4,17, 22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2, 4,6(33),8,10(32),11,13,15(20),16,18,23-undecaen-3-yl]acetic acid A mixture of ethyl (2S)-2-(tert-butoxy)-2-[(22S,23E)-16-fluoro-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl] acetate (50 mg, 0.075 mmol) and 1N NaOH (0.373 mL, 0.373 mmol) in MeOH (2 mL) was refluxed for 3 h. It was then filtered and purified by prep HPLC to isolate (2S)-2(tert-butoxy)-2-[(22S,23E)-16-fluoro-4,17,22,27-tetramethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8,10(32), 11,13,15(20),16,18,23-undecaen-3-yl]acetic acid (38 mg, 73%) as a white solid. $^1$H NMR (500 MHz, DMSO-d6) δ 8.30 (s, 1H), 7.86 (d, J=7.6 Hz, 1H), 7.48 (t, J=7.6 Hz, 1H), 7.29 (d, J=7.3 Hz, 1H), 7.10 (t, J=8.9 Hz, 1H), 7.02 (s, 1H), 6.80 (d, J=8.5 Hz, 1H), 6.02 (dd, J=15.6, 7.6 Hz, 1H), 5.84 (d, J=15.6 Hz, 1H), 5.73 (br. s., 1H), 5.03 (t, J=6.6 Hz, 1H), 4.60 (t, J=11.7 Hz, 1H), 3.80 (br. s., 2H), 3.65 (t, J=11.3 Hz, 1H), 3.19 (d, J=7.9 Hz, 1H), 2.51 (br. s., 1H), 2.49 (s, 3H), 2.11 (s, 3H), 1.82-1.69 (m, 2H), 1.63-1.45 (m, 2H), 1.10 (s, 3H), 1.08 (s, 9H), 1.02 (d, J=6.1 Hz, 3H). LCMS (M+1)=643.5.

INTERMEDIATE 56

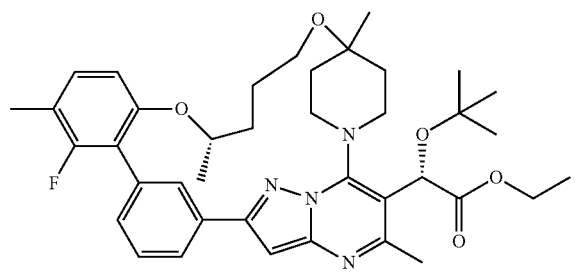 [SMILES: CCOC(=O)[C@@H](OC(C)(C)C)c1c(C)nc2cc3nn2c1N1CCC(C)(CC1)OCCC[C@H](C)Oc1ccc(C)c(F)c1-c1cccc-3c1]

Ethyl (2S)-2-(tert-butoxy)-2-[(22S)-16-fluoro-4,17, 22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2, 4,6(33),8,10(32),11,13,15(20),16,18-decaen-3-yl] acetate A mixture of ethyl (2S)-2-(tert-butoxy)-2-[(22S,23E)-16-fluoro-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6 (33),8,10(32),11,13,15(20),16,18,23-undecaen-3-yl]acetate (50 mg, 0.075 mmol), Grubbs II catalyst (6.33 mg, 7.45 μmol) and sodium borohydride (14.10 mg, 0.373 mmol) in EtOH (2 mL) was stirred at rt for 1 h. It was then diluted with water, extracted with EtOAc. The organic layer was dried over MgSO$_4$, filtered and concentrated to obtain 70 mg of an oil, which was then purified by biotage, eluting with 25% EtOAc/hexane to obtain ethyl (2S)-2-(tert-butoxy)-2-[(22S)-16-fluoro-4,17,22,27-tetramethyl-21,26-dioxa-1,5,7, 8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl] acetate (37 mg, 73.8%) as a white solid. LCMS (M+1)=673.1.

EXAMPLE 12

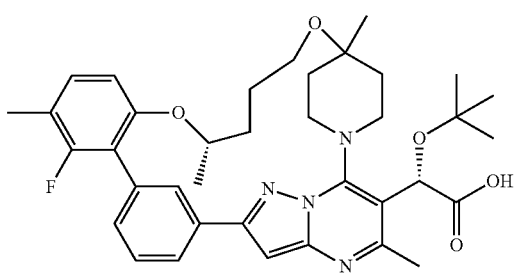 [SMILES: Cc1ccc2c(c1F)-c1cccc(c1)-c1cc3nc(C)c([C@H](OC(C)(C)C)C(=O)O)c(n3n1)N1CCC(C)(CC1)OCCC[C@H](C)O2]

(2S)-2-(tert-Butoxy)-2-[(22S)-16-fluoro-4,17,22,27-tetramethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8, 10(32),11,13,15(20),16,18-decaen-3-yl]acetic acid A mixture of ethyl (2S)-2-(tert-butoxy)-2-[(22S)-16-fluoro-4,17,22,27-tetramethyl-21,26-dioxa-1,5,7,8-tetraazahexacyclo[25.2.2.1^{6,9}.1^{10,14}.0^{2,7}.0^{15,20}]tritriaconta-2,4,6(33),8,10(32),11,13,15(20),16,18-decaen-3-yl]acetate (37 mg, 0.055 mmol) and 1N NaOH (0.275 mL, 0.275 mmol) in MeOH (2 mL) was refluxed for 3 h. It was then filtered and purified by prep HPLC to obtain (2S)-2-(tert-butoxy)-2-[(22S)-16-fluoro-4,17,22,27-tetramethyl-21,26-dioxa-1,5,7,8-tetraazahexacyclo[25.2.2.1^{6,9}.1^{10,14}.0^{2,7}.0^{15,20}]tritriaconta-2,4,6(33),8,10(32),11,13,15(20),16,18-decaen-3-yl]acetic acid (10 mg, 26.8%) as a white solid. $^1$H NMR (600 MHz, DMSO-d6) δ 8.17 (s, 1H), 7.90 (d, J=7.7 Hz, 1H), 7.52 (t, J=7.5 Hz, 1H), 7.32 (d, J=7.3 Hz, 1H), 7.22 (t, J=8.8 Hz, 1H), 7.06 (s, 1H), 6.99 (d, J=8.4 Hz, 1H), 5.78 (s, 1H), 4.59 (br. s., 1H), 4.48 (t, J=12.1 Hz, 1H), 3.60 (t, J=11.6 Hz, 1H), 3.37 (br. s., 1H), 3.31 (br. s., 1H), 3.21 (d, J=7.3 Hz, 1H), 2.70 (d, J=10.6 Hz, 1H), 2.53 (s, 3H), 2.20 (s, 3H), 2.06-1.97 (m, 1H), 1.93-1.88 (m, 1H), 1.86-1.68 (m, 3H), 1.61-1.46 (m, 3H), 1.20-1.15 (m, 12H), 1.14 (d, J=5.9 Hz, 3H). LCMS (M+1)=645.5.

INTERMEDIATE 57

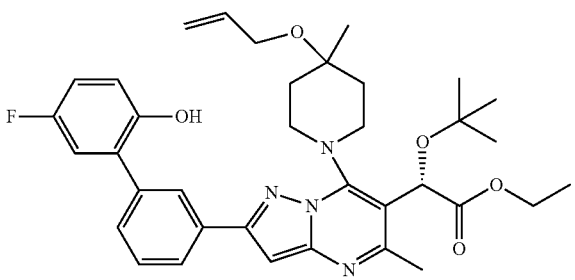 [SMILES: C=CCOC1(C)CCN(c2c([C@H](OC(C)(C)C)C(=O)OCC)c(C)nc3cc(-c4cccc(-c5cc(F)ccc5O)c4)nn23)CC1]

(S)-Ethyl 2-(7-(4-(allyloxy)-4-methylpiperidin-1-yl)-2-(5'-fluoro-2'-hydroxy-[1,1'-biphenyl]-3-yl)-5-methylpyrazolo[1,5-a]pyrimidin-6-yl)-2-(tert-butoxy)acetate A mixture of (S)-ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (200 mg, 0.334 mmol), 4-fluoro-2-(4,4,5,5-tetramethyl-1,3,2-dioxaborolan-2-yl)phenol (119 mg, 0.500 mmol) and Na$_2$CO$_3$ (0.417 mL, 0.834 mmol) in DMF (3 mL) was vacuum, back-filled with N$_2$ for 3 times. To this mixture was added Pd(Ph$_3$P)$_4$ (38.5 mg, 0.033 mmol) and heated at 90° C. for 3 h. The mixture was then diluted with EtOAc, washed with water. The organic was dried over MgSO$_4$, filtered and concentrated to obtain 250 mg of an oil, which was then purified by biotage, eluting with 25% acetone/hexane to isolate (S)-ethyl 2-(7-(4-(allyloxy)-4-methylpiperidin-1-yl)-2-(5'-fluoro-2'-hydroxy-[1,1'-biphenyl]-3-yl)-5-methylpyrazolo[1,5-a]pyrimidin-6-yl)-2-(tert-butoxy)acetate (200 mg, 95%) as a white solid. $^1$H NMR (400 MHz, CDCl$_3$) δ 8.08 (s, 1H), 8.05 (d, J=7.8 Hz, 1H), 7.59 (t, J=7.8 Hz, 1H), 7.45 (d, J=7.6 Hz, 1H), 7.33-7.26 (m, 1H), 6.85 (s, 1H), 6.80-6.77 (m, 1H), 6.76 (s, 1H), 6.14-5.90 (m, 2H), 5.74 (s, 1H), 5.40 (dd, J=17.1, 1.7 Hz, 1H), 5.10 (br. s., 1H), 4.34-4.13 (m, 2H), 4.02 (d, J=4.6 Hz, 2H), 2.64 (s, 3H), 2.12-1.89 (m, 2H), 1.74 (br. s., 1H), 1.62-1.58 (m, 1H), 1.37 (br. s., 3H), 1.29-1.20 (m, 12H), 4 protons from piperidine were missing. LCMS (M+1)=631.1.

INTERMEDIATE 58

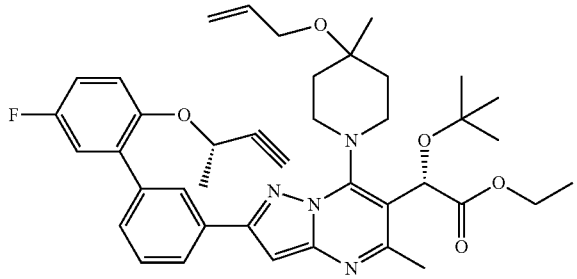 [SMILES: C#C[C@H](C)Oc1ccc(F)cc1-c1cccc(-c2cc3nc(C)c([C@H](OC(C)(C)C)C(=O)OCC)c(N4CCC(C)(OCC=C)CC4)n3n2)c1]

(S)-Ethyl 2-(7-(4-(allyloxy)-4-methylpiperidin-1-yl)-2-(2'-((S)-but-3-yn-2-yloxy)-5'-fluoro-[1,1'-biphenyl]-3-yl)-5-methylpyrazolo[1,5-a]pyrimidin-6-yl)-2-(tert-butoxy)acetate To a mixture of (S)-ethyl 2-(7-(4-(allyloxy)-4-methylpiperidin-1-yl)-2-(5'-fluoro-2'-hydroxy-[1,1'-biphenyl]-3-yl)-5-methylpyrazolo[1,5-a]pyrimidin-6-yl)-2-(tert-butoxy)acetate (200 mg, 0.317 mmol), (R)-but-3-yn-2-ol (44.4 mg, 0.634 mmol) and triphenylphosphine (166 mg, 0.634 mmol) at 0° C. in toluene (2 mL) was added DEAD (0.100 mL, 0.634 mmol) and the mixture was stirred at 0° C. for 3 h. It was then concentrated and purified by biotage, eluting with 20% EtOAc/hexane to isolate (S)-ethyl 2-(7-(4-(allyloxy)-4-methylpiperidin-1-yl)-2-(2'-((S)-but-3-yn-2-yloxy)-5'-fluoro-[1,1'-biphenyl]-3-yl)-5-methylpyrazolo[1,5-a]pyrimidin-6-yl)-2-(tert-butoxy)acetate (150 mg, 69%) as an off white solid. $^1$H NMR (400 MHz, CDCl$_3$) δ 8.19 (s, 1H), 8.06 (d, J=7.3 Hz, 1H), 7.60-7.55 (m, 1H), 7.54-7.48 (m, 1H), 7.23-7.15 (m, 2H), 7.07-7.01 (m, 1H), 6.86 (s, 1H), 6.10-5.92 (m, 2H), 5.42 (d, J=17.1 Hz, 1H), 5.14 (d, J=8.6 Hz, 1H), 4.75-4.65 (m, 1H), 4.28-4.19 (m, 2H), 4.03 (d, J=5.4 Hz, 2H), 2.64 (s, 3H), 2.47 (d, J=2.0 Hz, 1H), 1.97 (br. s., 2H), 1.75 (br. s., 1H), 1.61-1.56 (m, 1H), 1.54 (d, J=6.6 Hz, 3H), 1.39 (br. s., 3H), 1.30-1.21 (m, 12H), 4 protons from piperidine were missing. LCMS (M+1)=683.2.

INTERMEDIATE 59

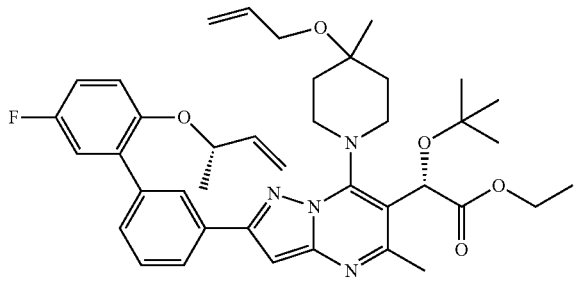 [SMILES: C=CCOC1(C)CCN(c2c([C@H](OC(C)(C)C)C(=O)OCC)c(C)nc3cc(-c4cccc(-c5cc(F)ccc5O[C@@H](C)C=C)c4)nn23)CC1]

(S)-Ethyl 2-(7-(4-(allyloxy)-4-methylpiperidin-1-yl)-2-(2'-((S)-but-3-en-2-yloxy)-5'-fluoro-[1,1'-biphenyl]-3-yl)-5-methylpyrazolo[1,5-a]pyrimidin-6-yl)-2-(tert-butoxy)acetate A mixture of chloro[1,3-bis(2,6-diisopropylphenyl)imidazol-2-ylidene]copper(I) (5.36 mg, 10.98 μmol) and sodium tert-butoxide (1.056 mg, 10.98 μmol) in THF (4 mL) was stirred at rt for 0.5 h. It was then added to a mixture of (S)-ethyl 2-(7-(4-(allyloxy)-4-methylpiperidin-1-yl)-2-(2'-((S)-but-3-yn-2-yloxy)-5'-fluoro-[1,1'-biphenyl]-3-yl)-5-methylpyrazolo[1,5-a]pyrimidin-6-yl)-2-(tert-butoxy)acetate (150 mg, 0.220 mmol), polymethylhydrosiloxane (26.4 mg, 0.439 mmol) and 2-methyl-1-propanol (0.024 mL, 0.264 mmol) in toluene (40 mL). The mixture was stirred at rt for 1 h. It was then diluted with EtOAc, washed with water. The organic layer was dried over MgSO$_4$, filtered and concentrated to obtain 200 mg of a brown oil, which was then purified by biotage, eluting with 20% EtOAc/hexane to isolate (S)-ethyl 2-(7-(4-(allyloxy)-4-methylpiperidin-1-yl)-2-(2'-((S)-but-3-en-2-yloxy)-5'-fluoro-[1,1'-biphenyl]-3-yl)-5-methylpyrazolo[1,5-a]pyrimidin-6-yl)-2-(tert-butoxy)acetate (140 mg, 93%) as an off-white solid. $^1$H NMR (400 MHz, CDCl$_3$) δ 8.19 (s, 1H), 8.06 (d, J=8.3 Hz, 1H), 7.61-7.55 (m, 1H), 7.54-7.48 (m, 1H), 7.18-7.13 (m, 1H), 7.00-6.95 (m, 2H), 6.85 (s, 1H), 6.18-5.92 (m, 2H), 5.83 (ddd, J=17.1, 10.6, 6.2 Hz, 1H), 5.42 (d, J=17.1 Hz, 1H), 5.22-5.05 (m, 3H), 4.62 (quin, J=6.4 Hz, 1H), 4.28-4.17 (m, 2H), 4.03 (d, J=5.1 Hz, 2H), 2.64 (s, 3H), 2.13-1.94 (m, 2H), 1.74 (br. s., 1H), 1.61-1.51 (m, 1H), 1.39 (br. s., 3H), 1.33 (d, J=6.4 Hz, 3H), 1.28-1.22 (m, 12H), 4 protons from piperidine were missing. LCMS (M+1)=685.6.

INTERMEDIATE 60

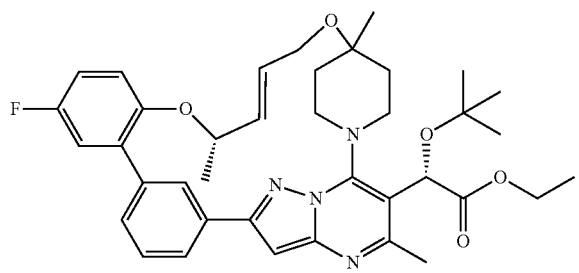 [SMILES: CCOC(=O)[C@@H](OC(C)(C)C)c1c(C)nc2cc3nn2c1N1CCC(C)(CC1)OC/C=C/[C@H](C)Oc1ccc(F)cc1-c1cccc-3c1]

Ethyl (2S)-2-(tert-butoxy)-2-[(22S,23E)-17-fluoro-4, 22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6 (33),8,10(32),11,13,15(20),16,18,23-undecaen-3-yl]acetate A mixture of Grubbs catalyst 2nd generation (17.36 mg, 0.020 mmol), copper(I) iodide (38.9 mg, 0.204 mmol) and (S)-ethyl 2-(7-(4-(allyloxy)-4-methylpiperidin-1-yl)-2-(2'-((S)-but-3-en-2-yloxy)-5'-fluoro-[1,1'-biphenyl]-3-yl)-5-methylpyrazolo[1,5-a]pyrimidin-6-yl)-2-(tert-butoxy)acetate (140 mg, 0.204 mmol) in ClCH$_2$CH$_2$Cl (150 mL) was refluxed for 2 h. It was then concentrated and purified by biotage, eluting with 20% EtOAc/hexane to isolate ethyl (2S)-2-(tert-butoxy)-2-[(22S,23E)-17-fluoro-4, 22,27-trimethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8,10(32), 11,13,15(20),16,18,23-undecaen-3-yl]acetate (90 mg, 67.3%) as a white solid. $^1$H NMR (400 MHz, CDCl$_3$) δ 8.63 (t, J=1.6 Hz, 1H), 7.79 (d, J=7.8 Hz, 1H), 7.53 (t, J=7.7 Hz, 1H), 7.37 (d, J=7.6 Hz, 1H), 7.06 (dd, J=9.0, 2.9 Hz, 1H), 6.99-6.92 (m, 2H), 6.90 (s, 1H), 6.28 (dd, J=15.7, 7.3 Hz, 1H), 6.06 (s, 1H), 5.96 (dt, J=15.4, 3.7 Hz, 1H), 5.00 (t, J=6.6 Hz, 1H), 4.82-4.73 (m, 1H), 4.29-4.15 (m, 2H), 4.09-3.92 (m, 3H), 3.17 (d, J=11.7 Hz, 1H), 2.73 (d, J=12.2 Hz, 1H), 2.65 (s, 3H), 2.03-1.89 (m, 2H), 1.82-1.61 (m, 2H), 1.32 (s, 3H), 1.29 (d, J=6.4 Hz, 3H), 1.27-1.23 (m, 12H). LCMS (M+1)=657.2.

EXAMPLE 13

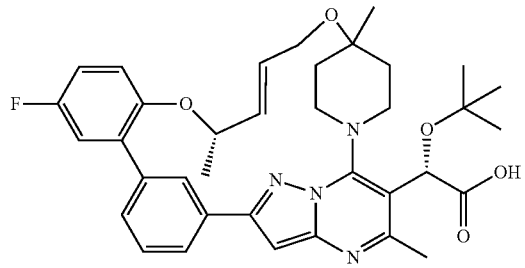 [SMILES: Cc1nc2cc3nn2c(c1[C@H](OC(C)(C)C)C(=O)O)N1CCC(C)(CC1)OC/C=C/[C@H](C)Oc1ccc(F)cc1-c1cccc-3c1]

(2S)-2-(tert-Butoxy)-2-[(22S,23E)-17-fluoro-4,22, 27-trimethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8, 10(32),11,13,15(20),16,18,23-undecaen-3-yl]acetic acid A mixture of ethyl (2S)-2-(tert-butoxy)-2-[(22S,23E)-17-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6 (33),8,10(32),11,13,15(20),16,18,23-undecaen-3-yl]acetate (80 mg, 0.122 mmol) and 1N NaOH (0.609 mL 0.122 mmol) in MeOH (2 mL) was refluxed for 3 h. It was then filtered and purify by prep HPLC to isolate (2S)-2-(tert-butoxy)-2-[(22S,23E)-17-fluoro-4,22,27-trimethyl-21,26-dioxa-1,5,7, 8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid (63.9 mg, 79%) as a white solid. $^1$H NMR (600 MHz, DMSO-d6) δ 8.58 (s, 1H), 7.92 (d, J=7.7 Hz, 1H), 7.55 (t, J=7.7 Hz, 1H), 7.40 (d, J=7.7 Hz, 1H), 7.24-7.17 (m, 1H), 7.17-7.12 (m, 2H), 7.10 (s, 1H), 6.22 (dd, J=15.4, 8.1 Hz, 1H), 6.01 (d, J=15.4 Hz, 1H), 5.75 (br. s., 1H), 5.20 (t, J=6.6 Hz, 1H), 4.67 (t, J=12.1 Hz, 1H), 4.02-3.85 (m, 3H), 3.77-3.67 (m, 1H), 2.62-2.56 (m, 1H), 2.53 (s, 3H), 1.86 (t, J=12.3 Hz, 2H), 1.71-1.55 (m, 2H), 1.23 (s, 3H), 1.17 (s, 9H), 1.15 (d, J=6.2 Hz, 3H). LCMS (M+1)=629.3.

INTERMEDIATE 61

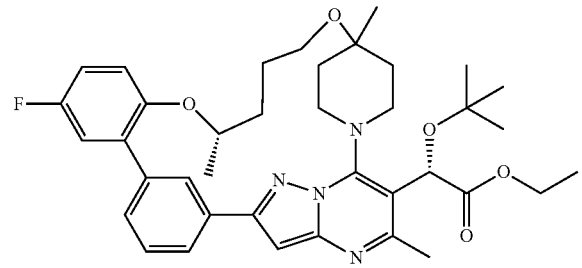 [SMILES: CCOC(=O)[C@@H](OC(C)(C)C)c1c(C)nc2cc3nn2c1N1CCC(C)(CC1)OCCC[C@H](C)Oc1ccc(F)cc1-c1cccc-3c1]

Ethyl (2S)-2-(tert-butoxy)-2-[(22S)-17-fluoro-4,22, 27-trimethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8, 10(32),11,13,15(20),16,18-decaen-3-yl]acetate A mixture of ethyl (2S)-2-(tert-butoxy)-2-[(22S,23E)-17-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6 (33),8,10(32),11,13,15(20),16,18,23-undecaen-3-yl]acetate (50 mg, 0.076 mmol), Grubb's II catalyst (6.46 mg, 7.61 µmol) and sodium borohydride (14.40 mg, 0.381 mmol) in EtOH (2 mL) was stirred at rt for 1 h. It was then diluted with water, extracted with EtOAc. The organic layer was dried over MgSO$_4$, filtered and concentrated to obtain 70 mg of an oil, which was then purified by biotage, eluting with 25% EtOAc/hexane to obtain ethyl (2S)-2-(tert-butoxy)-2-[(22S)-17-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4, 6(33),8,10(32),11,13,15(20),16,18-decaen-3-yl]acetate (37 mg, 74%) as a white solid. $^1$H NMR (400 MHz, CDCl$_3$) δ 8.57 (s, 1H), 7.78 (d, J=7.8 Hz, 1H), 7.57-7.49 (m, 1H), 7.41-7.36 (m, 1H), 7.10 (dd, J=9.3, 2.7 Hz, 1H), 7.03-6.96 (m, 2H), 6.88 (s, 1H), 6.06 (s, 1H), 4.63 (t, J=11.5 Hz, 1H), 4.45 (br. s., 1H), 4.28-4.14 (m, 2H), 3.91-3.80 (m, 1H), 3.47 (t, J=5.1 Hz, 2H), 3.15 (d, J=9.3 Hz, 1H), 2.82 (d, J=11.0 Hz, 1H), 2.65 (s, 3H), 2.38-2.21 (m, 1H), 2.04-1.88 (m, 3H), 1.80-1.64 (m, 4H), 1.30-1.21 (m, 18H). LCMS (M+1)=659.2.

EXAMPLE 14

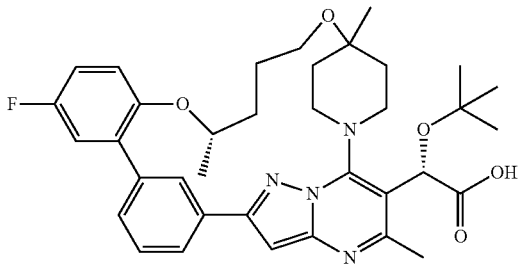 [SMILES: Cc1nc2cc3nn2c(c1[C@H](OC(C)(C)C)C(=O)O)N1CCC(C)(CC1)OCCC[C@H](C)Oc1ccc(F)cc1-c1cccc-3c1]

(2S)-2-(tert-Butoxy)-2-[(22S)-17-fluoro-4,22,27-trimethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8, 10(32),11,13,15(20),16,18-decaen-3-yl]acetic acid A mixture of ethyl (2S)-2-(tert-butoxy)-2-[(22S)-17-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6 (33),8,10(32),11,13,15(20),16,18-decaen-3-yl]acetate (27 mg, 0.041 mmol) and 1 N NaOH (0.205 mL, 0.205 mmol) in MeOH (1 mL) was refluxed for 3 h. It was then filtered and purified by prep HPLC to obtain (2S)-2-(tert-butoxy)-2-[(22S)-17-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid (22 mg, 81%) as a white solid. $^1$H NMR (600 MHz, DMSO-d6) δ 8.52 (s, 1H), 7.89 (d, J=7.7 Hz, 1H), 7.53 (t, J=7.7 Hz, 1H), 7.39 (d, J=7.3 Hz, 1H), 7.27-7.21 (m, 1H), 7.21-7.13 (m, 2H), 6.97 (s, 1H), 5.40 (s, 1H), 4.58 (br. s., 1H), 4.52 (t, J=12.3 Hz, 1H), 4.06-3.35 (m, 4H), 2.71 (br. s., 1H), 2.52 (br. s., 3H), 2.21-2.09 (m, 1H), 1.95 (d, J=12.5 Hz, 2H), 1.80-1.41 (m, 5H), 1.20 (s, 3H), 1.17 (d, J=5.9 Hz, 3H), 1.13 (s, 9H). LCMS (M+1)=631.1.

INTERMEDIATE 62

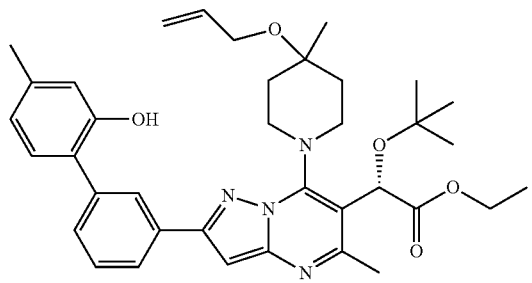 [SMILES: C=CCOC1(C)CCN(c2c([C@H](OC(C)(C)C)C(=O)OCC)c(C)nc3cc(-c4cccc(-c5ccc(C)cc5O)c4)nn23)CC1]

(S)-Ethyl 2-(7-(4-(allyloxy)-4-methylpiperidin-1-yl)-2-(2'-hydroxy-4'-methyl-[1,1'-biphenyl]-3-yl)-5-methylpyrazolo[1,5-a]pyrimidin-6-yl)-2-(tert-butoxy)acetate A mixture of (S)-ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (200 mg, 0.334 mmol), (2-hydroxy-4-methylphenyl)boronic acid (76 mg, 0.500 mmol) and 2M Na$_2$CO$_3$ (0.417 mL, 0.834 mmol) in DMF (3 mL) was vacuum, back-filled with N$_2$ for 3 times. To this mixture was then Pd(Ph$_3$P)$_4$ (38.5 mg, 0.033 mmol) and heated at 90° C. for 3 h. It was then diluted with EtOAc, washed with water. The organic layer was dried over MgSO$_4$, filtered and concentrated to obtain 200 mg of an oil, which was then purified by biotage, eluting with 25% acetone/hexane to isolate (S)-ethyl 2-(7-(4-(allyloxy)-4-methylpiperidin-1-yl)-2-(2'-hydroxy-4'-methyl-[1,1'-biphenyl]-3-yl)-5-methylpyrazolo[1,5-a]pyrimidin-6-yl)-2-(tert-butoxy)acetate (140 mg, 67%) as a white solid. $^1$H NMR (400 MHz, CDCl$_3$) δ 8.09 (s, 1H), 8.05 (d, J=7.6 Hz, 1H), 7.63-7.55 (m, 1H), 7.51-7.46 (m, 1H), 7.25-7.20 (m, 1H), 6.92-6.85 (m, 2H), 6.84 (s, 1H), 6.07-5.90 (m, 2H), 5.41 (dd, J=17.1, 1.7 Hz, 1H), 5.12 (d, J=10.5 Hz, 1H), 4.29-4.16 (m, 2H), 4.02 (d, J=5.1 Hz, 2H), 2.64 (s, 3H), 2.40 (s, 3H), 2.07-1.93 (m, 2H), 1.75 (d, J=7.1 Hz, 1H), 1.66-1.50 (m, 1H), 1.38 (br. s., 3H), 1.31-1.22 (m, 12H), 4 protons from piperidine were missing. LCMS (M+1)=627.3.

INTERMEDIATE 63

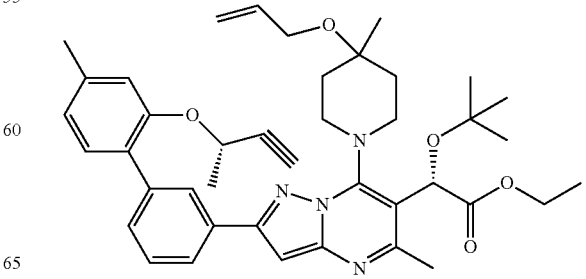

(S)-Ethyl 2-(7-(4-(allyloxy)-4-methylpiperidin-1-yl)-2-(2'-((S)-but-3-yn-2-yloxy)-4'-methyl-[1,1'-biphenyl]-3-yl)-5-methylpyrazolo[1,5-a]pyrimidin-6-yl)-2-(tert-butoxy)acetate To a mixture of (S)-ethyl 2-(7-(4-(allyloxy)-4-methylpiperidin-1-yl)-2-(2'-hydroxy-4'-methyl-[1,1'-biphenyl]-3-yl)-5-methylpyrazolo[1,5-a]pyrimidin-6-yl)-2-(tert-butoxy)acetate (160 mg, 0.255 mmol), (R)-but-3-yn-2-ol (35.8 mg, 0.511 mmol) and triphenylphosphine (134 mg, 0.511 mmol) at 0° C. in toluene (2 mL) was added DEAD (0.081 mL, 0.511 mmol) and the mixture was stirred at 0° C. to rt for 3 h. It was then concentrated and purified by biotage, eluting with 20% EtOAc/hexane to isolate (S)-ethyl 2-(7-(4-(allyloxy)-4-methylpiperidin-1-yl)-2-(2'-((S)-but-3-yn-2-yloxy)-4'-methyl-[1,1'-biphenyl]-3-yl)-5-methylpyrazolo[1,5-a]pyrimidin-6-yl)-2-(tert-butoxy)acetate (90 mg, 51.9%) as an off white solid. $^1$H NMR (400 MHz, CDCl$_3$) δ 8.16 (s, 1H), 8.04 (d, J=8.1 Hz, 1H), 7.60-7.56 (m, 1H), 7.51-7.45 (m, 1H), 7.34 (d, J=7.6 Hz, 1H), 7.07 (s, 1H), 6.96 (d, J=7.6 Hz, 1H), 6.85 (s, 1H), 6.09-5.91 (m, 2H), 5.43 (d, J=16.6 Hz, 1H), 5.15 (d, J=9.8 Hz, 1H), 4.83 (dd, J=6.4, 2.0 Hz, 1H), 4.29-4.16 (m, 2H), 4.03 (d, J=5.1 Hz, 2H), 2.64 (s, 3H), 2.48 (d, J=2.2 Hz, 1H), 2.44 (s, 3H), 2.14-1.90 (m, 3H), 1.74 (br. s., 1H), 1.39 (br. s., 3H), 1.29-1.22 (m, 15H), 4 protons from piperidine were missing. LCMS (M+1)=679.3.

INTERMEDIATE 64

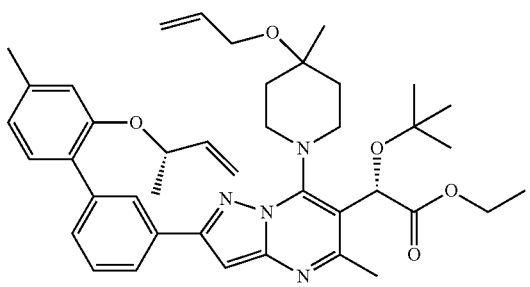 [SMILES: C=CCOC1(C)CCN(c2c([C@H](OC(C)(C)C)C(=O)OCC)c(C)nc3cc(-c4cccc(-c5ccc(C)cc5O[C@@H](C)C=C)c4)nn23)CC1]

(S)-Ethyl 2-(7-(4-(allyloxy)-4-methylpiperidin-1-yl)-2-(2'-((S)-but-3-en-2-yloxy)-4'-methyl-[1,1'-biphenyl]-3-yl)-5-methylpyrazolo[1,5-a]pyrimidin-6-yl)-2-(tert-butoxy)acetate A mixture of chloro[1,3-bis(2,6-diisopropylphenyl)imidazol-2-ylidene]copper (I) (3.59 mg, 7.37 µmol) and sodium tert-butoxide (0.708 mg, 7.37 µmol) in THF (1 mL) was stirred at rt for 0.5 h. It was then added to a mixture of (S)-ethyl 2-(7-(4-(allyloxy)-4-methylpiperidin-1-yl)-2-(2'-((S)-but-3-yn-2-yloxy)-4'-methyl-[1,1'-biphenyl]-3-yl)-5-methylpyrazolo[1,5-a]pyrimidin-6-yl)-2-(tert-butoxy)acetate (100 mg, 0.147 mmol), polymethylhydrosiloxane (17.68 mg, 0.295 mmol) and 2-methyl-1-propanol (0.016 mL, 0.177 mmol) in toluene (2 mL). The mixture was stirred at rt for 1 h. It was then diluted with EtOAc, washed with water. The organic layer was dried over MgSO$_4$, filtered and concentrated to obtain 0.11 g of a brown oil, which was then purified by biotage, eluting with 20% EtOAc/hexane to isolate (S)-ethyl 2-(7-(4-(allyloxy)-4-methylpiperidin-1-yl)-2-(2'-((S)-but-3-en-2-yloxy)-4'-methyl-[1,1'-biphenyl]-3-yl)-5-methylpyrazolo[1,5-a]pyrimidin-6-yl)-2-(tert-butoxy)acetate (90 mg, 90%) as an off white solid. $^1$H NMR (400 MHz, CDCl$_3$) δ 8.17 (s, 1H), 8.03 (d, J=7.8 Hz, 1H), 7.61-7.55 (m, 1H), 7.51-7.45 (m, 1H), 7.32 (d, J=7.8 Hz, 1H), 6.89 (d, J=7.6 Hz, 1H), 6.85 (s, 1H), 6.83 (s, 1H), 6.13-5.95 (m, 2H), 5.95-5.83 (m, 1H), 5.42 (d, J=16.9 Hz, 1H), 5.26-5.08 (m, 3H), 4.77 (t, J=6.0 Hz, 1H), 4.30-4.15 (m, 2H), 4.03 (d, J=4.6 Hz, 2H), 2.64 (s, 3H), 2.40 (s, 3H), 2.11-1.67 (m, 4H), 1.41-1.35 (m, 6H), 1.27-1.22 (m, 12H), 4 protons from piperidine were missing. LCMS (M+1)=681.2.

INTERMEDIATE 65

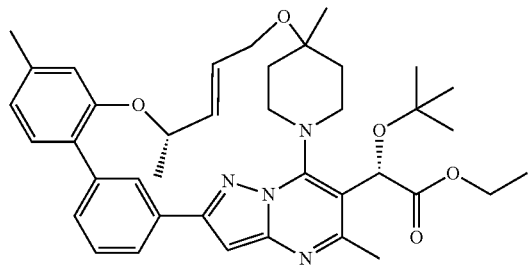 [SMILES: CCOC(=O)[C@@H](OC(C)(C)C)c1c(C)nc2cc3nn2c1N1CCC(C)(CC1)OC/C=C/[C@H](C)Oc1cc(C)ccc1-c1cccc-3c1]

Ethyl (2S)-2-(tert-butoxy)-2-[(22S,23E)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate A mixture of Grubbs catalyst 2nd generation (11.22 mg, 0.013 mmol), copper(I) iodide (25.2 mg, 0.132 mmol) and (S)-ethyl 2-(7-(4-(allyloxy)-4-methylpiperidin-1-yl)-2-(2'-((S)-but-3-en-2-yloxy)-4'-methyl-[1,1'-biphenyl]-3-yl)-5-methylpyrazolo[1,5-a]pyrimidin-6-yl)-2-(tert-butoxy)acetate (90 mg, 0.132 mmol) in ClCH$_2$CH$_2$Cl (100 mL) was refluxed for 2 h. It was then concentrated and purified by biotage, eluting with 20% EtOAc/hexane to isolate ethyl (2S)-2-(tert-butoxy)-2-[(22S,23E)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate (60 mg, 69.5%) as a white solid. $^1$H NMR (400 MHz, CDCl$_3$) δ 8.63 (s, 1H), 7.76 (d, J=8.1 Hz, 1H), 7.50 (t, J=7.6 Hz, 1H), 7.39 (d, J=8.1 Hz, 1H), 7.22 (d, J=7.6 Hz, 1H), 6.89 (s, 1H), 6.86-6.78 (m, 2H), 6.28 (dd, J=15.4, 7.1 Hz, 1H), 6.05 (s, 1H), 6.04-5.94 (m, 1H), 5.08 (t, J=6.8 Hz, 1H), 4.82-4.68 (m, 1H), 4.29-4.15 (m, 2H), 4.10-3.89 (m, 3H), 3.17 (d, J=11.2 Hz, 1H), 2.73 (d, J=12.0 Hz, 1H), 2.65 (s, 3H), 2.40 (s, 3H), 2.05-1.88 (m, 2H), 1.82-1.71 (m, 1H), 1.68-1.61 (m, 1H), 1.33-1.29 (m, 6H), 1.28-1.22 (m, 12H). LCMS (M+1)=653.2.

EXAMPLE 15

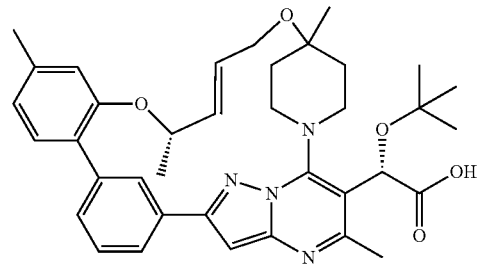 [SMILES: Cc1ccc2c(c1)O[C@@H](C)/C=C/COC1(C)CCN(CC1)c1c([C@H](OC(C)(C)C)C(=O)O)c(C)nc3cc(nn13)-c1cccc-2c1]

(2S)-2-(tert-Butoxy)-2-[(22S,23E)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid A mixture of ethyl (2S)-2-(tert-butoxy)-2-[(22S,23E)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate (50 mg, 0.077 mmol) and 1N NaOH (3.06 mg, 0.077 mmol) in MeOH (2 mL) was heated at refluxed for 3 h. It was then cooled to rt, purify with prep HPLC to obtain (2S)-2-(tert-butoxy)-2-[(22S,23E)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid (37.5 mg, 78%) as a white solid. $^1$H NMR (500 MHz, DMSO-d6) δ 8.55 (s, 1H), 7.87 (d, J=7.3 Hz, 1H), 7.51 (t, J=7.5 Hz, 1H), 7.34 (d, J=7.3 Hz, 1H), 7.15 (d, J=7.7 Hz, 1H), 7.10 (s, 1H), 7.02 (s, 1H), 6.81 (d, J=7.3 Hz, 1H), 6.21 (dd, J=15.6, 7.9 Hz, 1H), 6.01 (d, J=15.0 Hz, 1H), 5.80 (br. s., 1H), 5.23 (t, J=6.2 Hz, 1H), 4.66 (t, J=11.9 Hz, 1H), 3.96 (br. s., 2H), 3.74 (t, J=11.0 Hz, 1H), 3.26 (br. s., 1H), 2.60 (d, J=8.8 Hz, 1H), 2.53 (s, 3H), 2.34 (s, 3H), 1.94-1.81 (m, 2H), 1.68 (br. s., 1H), 1.63-1.54 (m, 1H), 1.23 (s, 3H), 1.20-1.13 (m, 12H). LCMS (M+1)=625.4.

INTERMEDIATE 66

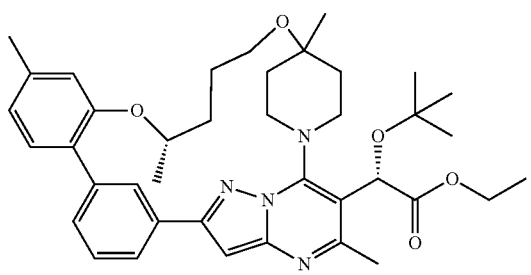 [SMILES: CCOC(=O)[C@@H](OC(C)(C)C)c1c(C)nc2cc3nn2c1N1CCC(C)(CC1)OCCC[C@H](C)Oc1cc(C)ccc1-c1cccc-3c1]

Ethyl (2S)-2-(tert-butoxy)-2-[(22S)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetate A mixture of ethyl (2S)-2-(tert-butoxy)-2-[(22S,23E)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate (30 mg, 0.046 mmol), Grubb's II catalyst (3.90 mg, 4.60 μmol) and sodium borohydride (8.69 mg, 0.230 mmol) in EtOH (2 mL) was stirred at rt for 1 h. It was then diluted with water, extracted with EtOAc. The organic layer was dried over MgSO$_4$, filtered and concentrated to obtain 50 mg of an oil, which was then purified by biotage, eluting with 25% EtOAc/hexane to obtain ethyl (2S)-2-(tert-butoxy)-2-[(22S)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetate (17 mg, 56%) as a white solid. LCMS (M+1)=655.1.

EXAMPLE 16

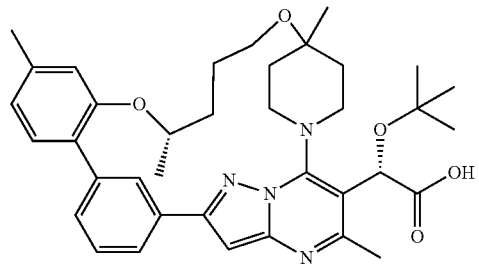 [SMILES: Cc1ccc2c(c1)O[C@@H](C)CCCOC1(C)CCN(CC1)c1c([C@H](OC(C)(C)C)C(=O)O)c(C)nc3cc(nn13)-c1cccc-2c1]

(2S)-2-(tert-Butoxy)-2-[(22S)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid A mixture of (2S)-2-(tert-butoxy)-2-[(22S)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetate (17 mg, 0.026 mmol) and 1N NaOH (0.13 mL, 0.13 mmol) in MeOH (2 mL) was refluxed for 3 h. It was then filtered and purified by prep HPLC to obtain (2S)-2-(tert-butoxy)-2-[(22S)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid (8.3 mg, 51%) as a white solid. $^1$H NMR (500 MHz, DMSO-d6) δ 8.47 (s, 1H), 7.85 (d, J=8.1 Hz, 1H), 7.50 (t, J=7.7 Hz, 1H), 7.33 (d, J=7.7 Hz, 1H), 7.19 (d, J=7.3 Hz, 1H), 7.07-6.99 (m, 2H), 6.82 (d, J=7.7 Hz, 1H), 5.63 (s, 1H), 4.62 (br. s., 1H), 4.50 (t, J=12.1 Hz, 1H), 3.61-3.52 (m, 1H), 3.50-3.34 (m, 3H), 2.71 (br. s., 1H), 2.52 (br. s., 3H), 2.35 (s, 3H), 2.21-2.12 (m, 1H), 1.96-1.47 (m, 7H), 1.19 (s, 3H), 1.17 (d, J=5.9 Hz, 3H), 1.15 (s, 9H). LCMS (M+1)=627.3.

INTERMEDIATE 67

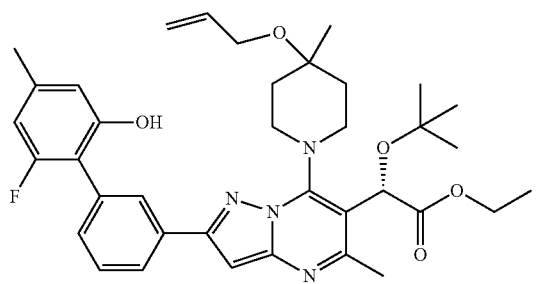 [SMILES: C=CCOC1(C)CCN(c2c([C@H](OC(C)(C)C)C(=O)OCC)c(C)nc3cc(-c4cccc(-c5c(O)cc(C)cc5F)c4)nn23)CC1]

(S)-Ethyl 2-(7-(4-(allyloxy)-4-methylpiperidin-1-yl)-2-(2'-fluoro-6'-hydroxy-4'-methylbiphenyl-3-yl)-5-methylpyrazolo[1,5-a]pyrimidin-6-yl)-2-tert-butoxyacetate A mixture of (S)-ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (200 mg, 0.334 mmol), (2-fluoro-6-hydroxy-4-methylphenyl)boronic acid (85 mg, 0.500 mmol) and 2M Na$_2$CO$_3$ (0.417 mL, 0.834 mmol) in DMF (3 mL) was vacuum, back-filled with N₂ for 3 times. To this mixture was added Pd(Ph₃P)₄ (38.5 mg, 0.033 mmol) and heated at 90° C. for 3 h. The mixture was then diluted with EtOAc, washed with water. The organic was dried over MgSO₄, filtered and concentrated to obtain 200 mg of an oil, which was then purified by biotage, eluting with 25% acetone/hexane to isolate (S)-ethyl 2-(7-(4-(allyloxy)-4-methylpiperidin-1-yl)-2-(2'-fluoro-6'-hydroxy-4'-methylbiphenyl-3-yl)-5-methylpyrazolo[1,5-a]pyrimidin-6-yl)-2-tert-butoxyacetate (140 mg, 65%) as a white solid. ¹H NMR (400 MHz, CDCl₃) δ 8.08 (d, J=8.3 Hz, 1H), 8.03 (s, 1H), 7.60 (t, J=7.7 Hz, 1H), 7.43 (d, J=7.1 Hz, 1H), 6.83 (s, 1H), 6.69 (s, 1H), 6.63 (d, J=10.3 Hz, 1H), 6.11-5.89 (m, 2H), 5.40 (dd, J=17.1, 1.7 Hz, 1H), 5.32 (br. s., 1H), 5.11 (d, J=9.8 Hz, 1H), 4.28-4.14 (m, 2H), 4.01 (d, J=4.9 Hz, 2H), 2.64 (s, 3H), 2.38 (s, 3H), 2.18-1.88 (m, 3H), 1.73 (br. s., 1H), 1.37 (br. s., 3H), 1.29-1.22 (m, 12H), 4 protons from piperidine were missing. LCMS (M+1)=645.1.

INTERMEDIATE 68

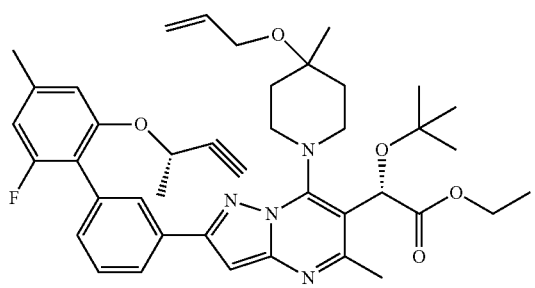 [SMILES: C#C[C@H](C)Oc1cc(C)cc(F)c1-c1cccc(-c2cc3nc(C)c([C@H](OC(C)(C)C)C(=O)OCC)c(N4CCC(C)(OCC=C)CC4)n3n2)c1]

(S)-Ethyl 2-(7-(4-(allyloxy)-4-methylpiperidin-1-yl)-2-(2'-((S)-but-3-yn-2-yloxy)-6'-fluoro-4'-methylbiphenyl-3-yl)-5-methylpyrazolo[1,5-a]pyrimidin-6-yl)-2-tert-butoxyacetate To a mixture of (S)-ethyl 2-(7-(4-(allyloxy)-4-methylpiperidin-1-yl)-2-(2'-fluoro-6'-hydroxy-4'-methyl-[1,1'-biphenyl]-3-yl)-5-methylpyrazolo[1,5-a]pyrimidin-6-yl)-2-(tert-butoxy)acetate (200 mg, 0.310 mmol), (R)-but-3-yn-2-ol (43.5 mg, 0.620 mmol) and triphenylphosphine (163 mg, 0.620 mmol) at 0° C. in toluene (2 mL) was added DEAD (0.098 mL, 0.620 mmol) and the mixture was stirred at rt for 3 h. It was then concentrated and purified by biotage, eluting with 20% EtOAc/hexane to isolate (S)-ethyl 2-(7-(4-(allyloxy)-4-methylpiperidin-1-yl)-2-(2'-((S)-but-3-yn-2-yloxy)-6'-fluoro-4'-methylbiphenyl-3-yl)-5-methylpyrazolo[1,5-a]pyrimidin-6-yl)-2-tert-butoxyacetate (135 mg, 62.5%) as an off white solid. ¹H NMR (400 MHz, CDCl₃) δ 8.13-8.00 (m, 2H), 7.53-7.44 (m, 2H), 6.88-6.82 (m, 2H), 6.72 (d, J=10.3 Hz, 1H), 6.11-5.85 (m, 2H), 5.42 (d, J=17.1 Hz, 1H), 5.14 (d, J=10.5 Hz, 1H), 4.85-4.76 (m, 1H), 4.27-4.16 (m, 2H), 4.02 (d, J=5.1 Hz, 2H), 2.63 (s, 3H), 2.50 (d, J=2.0 Hz, 1H), 2.43 (s, 3H), 2.13-1.91 (m, 2H), 1.86-1.62 (m, 1H), 1.61-1.53 (m, 1H), 1.51 (d, J=6.6 Hz, 3H), 1.38 (br. s., 3H), 1.31-1.20 (m, 12H), 4 protons prom piperidine were missing. LCMS (M+1)=679.2.

INTERMEDIATE 69

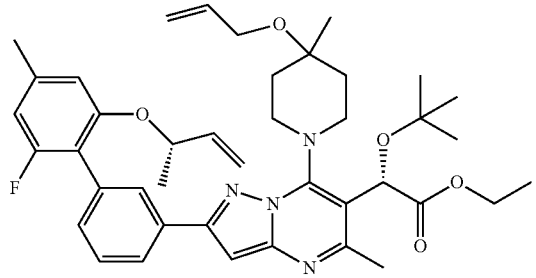 [SMILES: C=CCOC1(C)CCN(c2c([C@H](OC(C)(C)C)C(=O)OCC)c(C)nc3cc(-c4cccc(-c5c(F)cc(C)cc5O[C@@H](C)C=C)c4)nn23)CC1]

(S)-Ethyl 2-(7-(4-(allyloxy)-4-methylpiperidin-1-yl)-2-(2'-((S)-but-3-en-2-yloxy)-6'-fluoro-4'-methylbiphenyl-3-yl)-5-methylpyrazolo[1,5-a]pyrimidin-6-yl)-2-tert-butoxyacetate A mixture of chloro[1,3-bis(2,6-diisopropylphenyl)imidazol-2-ylidene]copper(I) (4.72 mg, 9.69 µmol) and sodium tert-butoxide (0.931 mg, 9.69 µmol) in THF (1 mL) was stirred at rt for 0.5 h. It was then added to a mixture of (S)-ethyl 2-(7-(4-(allyloxy)-4-methylpiperidin-1-yl)-2-(2'-((S)-but-3-yn-2-yloxy)-6'-fluoro-4'-methyl-[1,1'-biphenyl]-3-yl)-5-methylpyrazolo[1,5-a]pyrimidin-6-yl)-2-(tert-butoxy)acetate (135 mg, 0.194 mmol), polymethylhydrosiloxane (23.25 mg, 0.387 mmol) and 2-methyl-1-propanol (0.022 mL, 0.232 mmol) in toluene (2 mL). The mixture was stirred at rt for 1 h. It was then diluted with EtOAc, washed with water. The organic layer was dried over MgSO₄, filtered and concentrated to obtain 150 mg of a brown oil, which was then purified by biotage, eluting with 20% EtOAc/hexane to isolate (S)-ethyl 2-(7-(4-(allyloxy)-4-methylpiperidin-1-yl)-2-(2'-((S)-but-3-en-2-yloxy)-6'-fluoro-4'-methylbiphenyl-3-yl)-5-methylpyrazolo[1,5-a]pyrimidin-6-yl)-2-tert-butoxyacetate (130 mg, 96%) of an off-white solid. ¹H NMR (400 MHz, CDCl₃) δ 8.10-8.01 (m, 2H), 7.52-7.42 (m, 2H), 6.82 (s, 1H), 6.70-6.60 (m, 2H), 6.12-5.89 (m, 2H), 5.83 (ddd, J=17.3, 10.6, 5.9 Hz, 1H), 5.42 (dd, J=17.1, 1.5 Hz, 1H), 5.21-5.06 (m, 3H), 4.74 (quin, J=6.2 Hz, 1H), 4.26-4.15 (m, 2H), 4.07-3.95 (m, 2H), 2.63 (s, 3H), 2.39 (s, 3H), 2.11-1.62 (m, 4H), 1.38 (br. s., 3H), 1.33-1.29 (m, 3H), 1.28-1.21 (m, 12H), 4 protons from piperidine were missing. LCMS (M+1)=699.2.

INTERMEDIATE 70

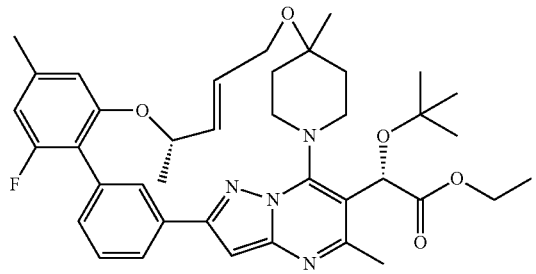 [SMILES: CCOC(=O)[C@@H](OC(C)(C)C)c1c(C)nc2cc3nn2c1N1CCC(C)(CC1)OC/C=C/[C@H](C)Oc1cc(C)cc(F)c1-c1cccc-3c1]

Ethyl (2S)-2-(tert-butoxy)-2-[(22S,23E)-16-fluoro-4, 18,22,27-tetramethyl-21,26-dioxa-1,5,7,8-tetraaza-hexacyclo[25.2.2.1$^{6,9}$.1$^{10,14}$.0$^{2,7}$.0$^{15,20}$]tritriaconta-2, 4,6(33),8,10(32),11,13,15(20),16,18,23-undecaen-3-yl]acetate A mixture of Grubbs catalyst 2$^{nd}$ generation (15.79 mg, 0.019 mmol), copper(I) iodide (35.4 mg, 0.186 mmol) and (S)-ethyl 2-(7-(4-(allyloxy)-4-methylpiperidin-1-yl)-2-(2'-((S)-but-3-en-2-yloxy)-6'-fluoro-4'-methyl-[1,1'-biphenyl]-3-yl)-5-methylpyrazolo[1,5-a]pyrimidin-6-yl)-2-(tert-butoxy)acetate (130 mg, 0.186 mmol) in ClCH$_2$CH$_2$Cl (170 mL) was refluxed for 2 h. It was then concentrated and purify by biotage, eluting with 25% EtOAc/hexane to isolate ethyl (2S)-2-(tert-butoxy)-2-[(22S,23E)-16-fluoro-4,18,22, 27-tetramethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8,10(32), 11,13,15(20),16,18,23-undecaen-3-yl]acetate (90 mg, 72%) as a white solid. $^1$H NMR (400 MHz, CDCl$_3$) δ 8.42 (t, J=1.5 Hz, 1H), 7.79 (d, J=7.6 Hz, 1H), 7.57-7.46 (m, 1H), 7.40 (d, J=7.3 Hz, 1H), 6.89 (s, 1H), 6.70-6.52 (m, 2H), 6.20 (dd, J=15.6, 7.1 Hz, 1H), 6.07 (s, 1H), 5.96 (dt, J=15.5, 3.9 Hz, 1H), 5.09-4.94 (m, 1H), 4.78 (t, J=11.2 Hz, 1H), 4.30-4.13 (m, 2H), 4.08-3.88 (m, 3H), 3.15 (d, J=11.7 Hz, 1H), 2.73 (d, J=11.7 Hz, 1H), 2.65 (s, 3H), 2.38 (s, 3H), 2.05-1.89 (m, 2H), 1.81-1.60 (m, 2H), 1.33-1.21 (m, 18H). LCMS (M+1)=671.3.

EXAMPLE 17

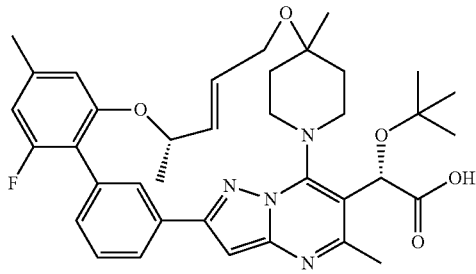

(2S)-2-(tert-Butoxy)-2-[(22S,23E)-16-fluoro-4,18, 22,27-tetramethyl-21,26-dioxa-1,5,7,8-tetraaza-hexacyclo[25.2.2.1$^{6,9}$.1$^{10,14}$.0$^{2,7}$.0$^{15,20}$]tritriaconta-2, 4,6(33),8,10(32),11,13,15(20),16,18,23-undecaen-3-yl]acetic acid A mixture of ethyl (2S)-2-(tert-butoxy)-2-[(22S,23E)-16-fluoro-4,18,22,27-tetramethyl-21,26-dioxa-1,5,7,8-tetraaza-hexacyclo[25.2.2.1$^{6,9}$.1$^{10,14}$.0$^{2,7}$.0$^{15,20}$]tritriaconta-2,4,6 (33),8,10(32),11,13,15(20),16,18,23-undecaen-3-yl]acetate (50 mg, 0.075 mmol) and 1N NaOH (0.373 mL, 0.373 mmol) in MeOH (2 mL) was refluxed for 3 h. It was then concentrated and purified by prep HPLC to isolate (2S)-2-(tert-butoxy)-2-[(22S,23E)-16-fluoro-4,18,22,27-tetramethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8,10(32), 11,13,15(20),16,18,23-undecaen-3-yl]acetic acid (32.3 mg, 64%) as a white solid. $^1$H NMR (500 MHz, DMSO-d6) δ 8.34 (s, 1H), 7.93 (d, J=7.7 Hz, 1H), 7.52 (t, J=7.7 Hz, 1H), 7.33 (d, J=7.7 Hz, 1H), 7.12 (s, 1H), 6.90 (s, 1H), 6.71 (d, J=10.3 Hz, 1H), 6.16-6.08 (m, 1H), 6.04-5.97 (m, 1H), 5.83 (s, 1H), 5.25-5.18 (m, 1H), 4.67 (t, J=11.7 Hz, 1H), 3.95 (br. s., 2H), 3.72 (t, J=11.4 Hz, 1H), 3.21 (d, J=7.3 Hz, 1H), 2.62 (d, J=11.7 Hz, 1H), 2.54 (s, 3H), 2.34 (s, 3H), 1.88 (d, J=13.2 Hz, 2H), 1.72-1.55 (m, 2H), 1.23 (s, 3H), 1.18 (s, 9H), 1.13 (d, J=6.2 Hz, 3H). LCMS (M+1)=643.3.

INTERMEDIATE 71

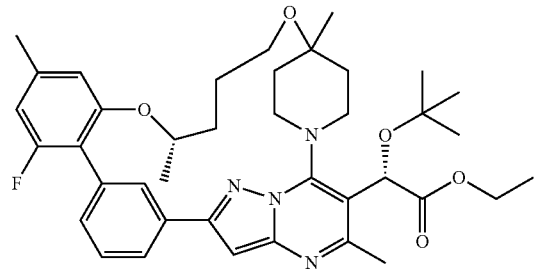 [SMILES: CCOC(=O)[C@@H](OC(C)(C)C)c1c(C)nc2cc3nn2c1N1CCC(C)(CC1)OCCC[C@H](C)Oc1cc(C)cc(F)c1-c1cccc-3c1]

Ethyl (2S)-2-(tert-butoxy)-2-[(22S)-16-fluoro-4,18, 22,27-tetramethyl-21,26-dioxa-1,5,7,8-tetraaza-hexacyclo[25.2.2.1$^{6,9}$.1$^{10,14}$.0$^{2,7}$.0$^{15,20}$]tritriaconta-2, 4,6(33),8,10(32),11,13,15(20),16,18-decaen-3-yl]acetate A mixture of ethyl (2S)-2-(tert-butoxy)-2-[(22S,23E)-16-fluoro-4,18,22,27-tetramethyl-21,26-dioxa-1,5,7,8-tetraaza-hexacyclo[25.2.2.1$^{6,9}$.1$^{10,14}$.0$^{2,7}$.0$^{15,20}$]tritriaconta-2,4,6 (33),8,10(32),11,13,15(20),16,18,23-undecaen-3-yl]acetate (40 mg, 0.060 mmol) and NaBH$_4$ (2.256 mg, 0.060 mmol) in EtOH (2 mL) was stirred at rt for 1 h. It was then diluted with EtOAc and washed with water. The organic layer was dried over MgSO$_4$, filtered and concentrated to obtain a brown oil, which was then purified by biotage, eluting with 25% EtOAc/hexane to isolate ethyl (2S)-2-(tert-butoxy)-2-[(22S)-16-fluoro-4,18,22,27-tetramethyl-21,26-dioxa-1,5,7, 8-tetraazahexacyclo[25.2.2.1$^{6,9}$.1$^{10,14}$.0$^{2,7}$.0$^{15,20}$]tritria-conta-2,4,6(33),8,10(32),11,13,15(20),16,18-decaen-3-yl] acetate (40 mg, 100%) as a white solid. $^1$H NMR (400 MHz, CDCl$_3$) δ 8.28 (s, 1H), 7.76 (d, J=7.8 Hz, 1H), 7.50 (t, J=7.7 Hz, 1H), 7.41-7.36 (m, 1H), 6.86 (s, 1H), 6.66 (s, 1H), 6.61 (d, J=9.8 Hz, 1H), 6.08 (s, 1H), 4.64 (t, J=11.1 Hz, 1H), 4.51 (d, J=8.8 Hz, 1H), 4.26-4.16 (m, 2H), 3.88-3.78 (m, 1H), 3.44 (t, J=5.4 Hz, 2H), 3.11 (d, J=10.0 Hz, 1H), 2.80 (d, J=13.0 Hz, 1H), 2.64 (s, 3H), 2.40 (s, 3H), 2.21 (d, J=14.4 Hz, 1H), 2.01-1.62 (m, 7H), 1.29-1.21 (m, 18H). LCMS (M+1)=673.3.

EXAMPLE 18

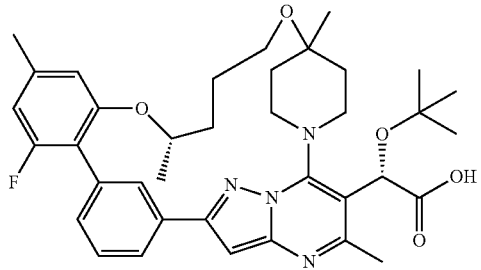 [SMILES: Cc1cc(F)c2c(c1)O[C@@H](C)CCCOC1(C)CCN(CC1)c1c([C@H](OC(C)(C)C)C(=O)O)c(C)nc3cc(nn13)-c1cccc-2c1]

(2S)-2-(tert-Butoxy)-2-[(22S)-16-fluoro-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid A mixture of ethyl (2S)-2-(tert-butoxy)-2-[(22S)-16-fluoro-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetate (40 mg, 0.059 mmol) and 1 N NaOH (0.297 mL, 0.297 mmol) in MeOH (2 mL) was refluxed for 3 h. It was then filtered and purified by prep HPLC to obtain (2S)-2-(tert-butoxy)-2-[(22S)-16-fluoro-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid (18 mg, 44.6%) as an white solid. $^1$H NMR (500 MHz, DMSO-d6) δ 8.17 (s, 1H), 7.89 (d, J=7.7 Hz, 1H), 7.51 (t, J=7.7 Hz, 1H), 7.30 (d, J=7.3 Hz, 1H), 7.05 (s, 1H), 6.94 (s, 1H), 6.71 (d, J=10.3 Hz, 1H), 5.75 (s, 1H), 4.64 (br. s., 1H), 4.50 (t, J=11.4 Hz, 1H), 3.58 (t, J=12.1 Hz, 1H), 3.48-3.22 (m, 3H), 2.71 (br. s., 1H), 2.53 (s, 3H), 2.36 (s, 3H), 2.11-2.01 (m, 1H), 1.95-1.90 (m, 1H), 1.86-1.68 (m, 3H), 1.65-1.47 (m, 3H), 1.19 (s, 3H), 1.18-1.14 (m, 12H). LCMS (M+1)=645.5.

INTERMEDIATE 72

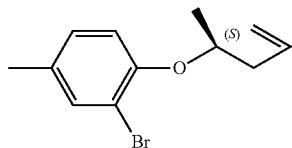

(S)-2-Bromo-4-methyl-1-(pent-4-en-2-yloxy)benzene

To a solution of 2-bromo-4-methylphenol (9.68 mL, 80 mmol) and (R)-pent-4-en-2-ol (7.60 g, 88 mmol) in THF (400 mL) was added Ph$_3$P (31.6 g, 120 mmol) followed by (Z)-diethyl diazene-1,2-dicarboxylate (19.05 mL, 120 mmol) and the resulting mixture was stirred at room temp for 16 h. Water (100 mL) was then added and the mixture was extracted with EtOAc (300 mL), washed with 1N NaOH (50 mL), brine (100 mL), dried (Na$_2$SO$_4$), filtered and concentrated. the residue was then purified via Biotage (0-10% EtOAc/hexane) to afford (S)-2-bromo-4-methyl-1-(pent-4-en-2-yloxy)benzene as light yellow oil. $^1$H NMR (500 MHz, CDCl$_3$) δ 7.40-7.37 (m, 1H), 7.05 (ddd, J=8.3, 2.1, 0.6 Hz, 1H), 6.86-6.81 (m, 1H), 5.93 (ddt, J=17.2, 10.1, 7.1 Hz, 1H), 5.19-5.08 (m, 2H), 4.40 (sxt, J=6.1 Hz, 1H), 2.60-2.51 (m, 1H), 2.46-2.38 (m, 1H), 2.29 (s, 3H), 1.36 (d, J=6.1 Hz, 3H).

INTERMEDIATE 73

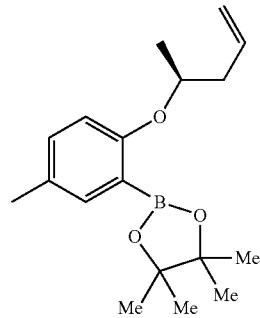 [SMILES: C=CC[C@H](C)Oc1ccc(C)cc1B1OC(C)(C)C(C)(C)O1]

(S)-4,4,5,5-Tetramethyl-2-(5-methyl-2-(pent-4-en-2-yloxy)phenyl)-1,3,2-dioxaborolane To a solution of (S)-2-bromo-4-methyl-1-(pent-4-en-2-yloxy)benzene (8.75 g, 34.3 mmol) in THF (200 mL) at −78° C. was added nBuLi, 1.6M in THF (25.7 mL, 41.2 mmol) and the mixture was stirred for 30 min. 2-isopropoxy-4,4,5,5-tetramethyl-1,3,2-dioxaborolane (8.40 mL, 41.2 mmol). After 30 min, bath removed and reaction allowed to warm to rt. After 3 h, water (50 mL) was added and the mixture was extracted with EtOAc (300 mL). EtOAc layer was dried (Na$_2$SO$_4$), filtered and concentrated to afford (S)-4,4,5,5-tetramethyl-2-(5-methyl-2-(pent-4-en-2-yloxy)phenyl)-1,3,2-dioxaborolane (10 g, 33.1 mmol, 96% yield) as yellow oil. Crude was used as is in the next step without further purification. Please note that product may be volatile and not to put on a high vac for longer period of time. $^1$H NMR (500 MHz, CDCl$_3$) δ 7.46 (d, J=2.0 Hz, 1H), 7.17 (dd, J=8.4, 2.4 Hz, 1H), 6.82 (d, J=8.4 Hz, 1H), 6.03-5.93 (m, 1H), 5.14-5.04 (m, 2H), 4.35-4.29 (m, 1H), 2.56-2.48 (m, 1H), 2.40 (dt, J=13.9, 6.8 Hz, 1H), 2.30 (s, 3H), 1.37 (s, 12H), 1.30 (d, J=6.1 Hz, 3H). LCMS (M+H)=303.3.

INTERMEDIATE 74

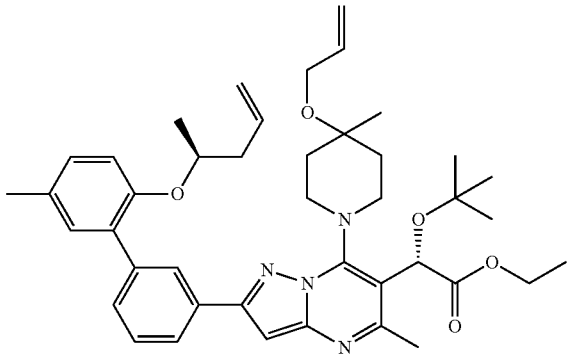 [SMILES: C=CCOC1(C)CCN(c2c([C@H](OC(C)(C)C)C(=O)OCC)c(C)nc3cc(-c4cccc(-c5cc(C)ccc5O[C@@H](C)CC=C)c4)nn23)CC1]

(S)-Ethyl 2-(7-(4-(allyloxy)-4-methylpiperidin-1-yl)-5-methyl-2-(5'-methyl-2'-((S)-pent-4-en-2-yloxy)-[1,1'-biphenyl]-3-yl)pyrazolo[1,5-a]pyrimidin-6-yl)-2-(tert-butoxy)acetate A solution of ((S)-ethyl 2-(7-(4-(allyloxy)-4-methylpiperidin-1-yl)-2-(3-bromophenyl)-5-methylpyrazolo[1,5-a]

pyrimidin-6-yl)-2-(tert-butoxy)acetate (5.1 g, 8.51 mmol), (S)-4,4,5,5-tetramethyl-2-(5-methyl-2-(pent-4-en-2-yloxy) phenyl)-1,3,2-dioxaborolane (3.86 g, 12.76 mmol) and 2.0 M aq. Na$_2$CO$_3$ (10.63 mL, 21.27 mmol) in DMF (100 mL) was degassed for 10 min. Pd(Ph$_3$P)$_4$ (0.688 g, 0.595 mmol), was added and the degassing was continued for another 5 min. The reaction was then heated at 90° C. for 3 hrs. At this point LCMS indicates completion of reaction. The mixture was then cooled to room temp and diluted with water (50 mL) and extracted with Et$_2$O (2×100 mL). The combined extracts were dried (Na$_2$SO$_4$), filtered, and concentrated under reduced pressure, and the residue was purified by biotage (0-25% EtOAc/hexane) to afford (S)-ethyl 2-(7-(4-(allyloxy)-4-methylpiperidin-1-yl)-5-methyl-2-(5'-methyl-2'-((S)-pent-4-en-2-yloxy)-[1,1'-biphenyl]-3-yl)pyrazolo[1,5-a]pyrimidin-6-yl)-2-(tert-butoxy)acetate (4.5 g, 6.48 mmol, 76% yield) as white foam. $^1$H NMR (500 MHz, CDCl$_3$) δ 7.58 (d, J=7.4 Hz, 1H), 7.48 (t, J=7.7 Hz, 1H), 7.25 (d, J=1.9 Hz, 1H), 7.13 (dd, J=8.4, 1.7 Hz, 1H), 6.94 (d, J=8.4 Hz, 1H), 6.85 (s, 1H), 6.01 (dt, J=10.4, 5.3 Hz, 1H), 6.05 (dt, J=10.4, 5.2 Hz, 1H), 5.77 (ddt, J=17.2, 10.2, 7.1 Hz, 1H), 5.43 (d, J=17.7 Hz, 1H), 5.15 (d, J=9.5 Hz, 1H), 5.06-4.97 (m, 2H), 4.37-4.14 (m, 4H), 4.03 (d, J=4.9 Hz, 2H), 2.64 (s, 3H), 2.46-2.39 (m, 1H), 2.38 (s, 3H), 2.27 (dt, J=14.0, 6.9 Hz, 1H), 2.09-1.93 (m, 3H), 1.76 (br. s., 1H), 1.40 (br. s., 3H), 1.28-1.26 (m, 10H), 1.24 (t, J=6.5 Hz, 6H). 4 missing piperidine hydrogens. LCMS (M+H)=695.4.

EXAMPLE 19

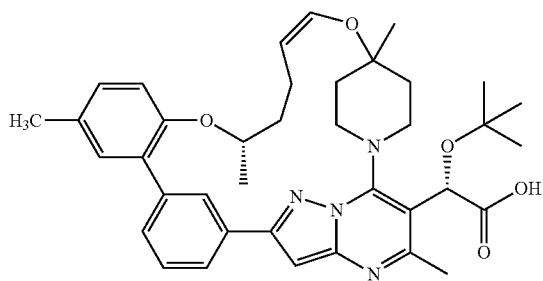 [SMILES: Cc1ccc2c(c1)-c1cccc(c1)-c1cc3nc(C)c([C@H](OC(C)(C)C)C(=O)O)c(n3n1)N1CCC(C)(CC1)O/C=C\CC[C@H](C)O2]

(2S)-2-(tert-Butoxy)-2-[(22S,25Z)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,25-undecaen-3-yl]acetic acid To a solution of (S)-ethyl 2-(7-(4-(allyloxy)-4-methylpiperidin-1-yl)-5-methyl-2-(5'-methyl-2'-((S)-pent-4-en-2-yloxy)-[1,1'-biphenyl]-3-yl)pyrazolo[1,5-a]pyrimidin-6-yl)-2-(tert-butoxy)acetate (100 mg, 0.14 mmol) in DCE (100 mL) at room temp was added CuI (27 mg, 0.14 mmol) followed by (1,3-dimesitylimidazolidin-2-ylidene)(2-isopropoxybenzylidene)ruthenium(VI) chloride (9 mg, 0.014 mmol) and the resulting mixture was heated at 80° C. for 2 h. At this point LCMS indicated completion of reaction. Mixture was then cooled and concentrated to afford brown solid which was treated with 1N NaOH (0.750 mL, 0.750 mmol) in MeOH (3 mL) at 75° C. for 5 h. Mixture was then cooled and purified by prep HPLC to afford (2S)-2-(tert-butoxy)-2-[(22S,25Z)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,25-undecaen-3-yl]acetic acid (60 mg, 0.089 mmol, 59.5% yield) as white solid. $^1$H NMR (500 MHz, DMSO-d$_6$) δ 8.48 (s, 1H), 7.89 (d, J=7.9 Hz, 1H), 7.52 (t, J=7.7 Hz, 1H), 7.36 (d, J=7.6 Hz, 1H), 7.17-7.13 (m, 2H), 7.09-7.01 (m, 2H), 6.33 (d, J=6.3 Hz, 1H), 5.58 (br. s., 1H), 4.57-4.49 (m, 2H), 4.38 (t, J=11.9 Hz, 1H), 3.56 (br. s., 2H), 2.90 (d, J=11.5 Hz, 1H), 2.40-2.25 (m, 6H), 1.98-1.88 (m, 4H), 1.85 (br. s., 1H), 1.78-1.70 (m, 2H), 1.67-1.53 (m, 1H), 1.33 (s, 3H), 1.17 (s, 9H), 1.08 (d, J=6.1 Hz, 3H). LCMS (M+H)=639.6.

INTERMEDIATE 75

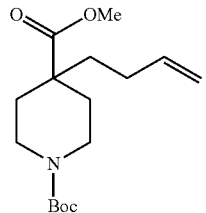 [SMILES: C=CCCC1(C(=O)OC)CCN(C(=O)OC(C)(C)C)CC1]

1-tert-Butyl 4-methyl 4-(but-3-en-1-yl)piperidine-1,4-dicarboxylate

A mixture of diisopropylamine (17.57 mL, 123 mmol) and THF (300 mL) was cooled to −78° C. and 1.6 M solution of n-BuLi (77 mL, 123 mmol) in hexane was added slowly. The mixture was stirred for 15 min, warmed to 0° C. for 20 min and cooled back to −78° C. 1-tert-Butyl 4-methyl piperidine-1,4-dicarboxylate (25 g, 103 mmol) in THF (25 mL) was added dropwise and the mixture was stirred for 40 min. Then, a mixture of HMPA (17.88 mL, 103 mmol) and 4-bromobut-1-ene (27.7 g, 206 mmol) was added and the mixture was stirred for 1 h before it was warmed to room temp and stir for 16 h. Sat. NH$_4$Cl was then added and the mixture was extracted with ether (2×500 mL), dried (Na$_2$SO$_4$), filtered and concentrated. The residue was purified by Biotage (0-20% EtOAc/hexane; 300 g column) to afford 1-tert-butyl 4-methyl 4-(but-3-en-1-yl)piperidine-1,4-dicarboxylate (22 g, 74.0 mmol, 72.0% yield) as light yellow oil. $^1$H NMR (500 MHz, CDCl$_3$) δ 5.76 (ddt, J=17.0, 10.3, 6.5 Hz, 1H), 5.06-4.92 (m, 2H), 3.94-3.85 (m, 2H), 3.73 (s, 3H), 2.95-2.80 (m, 2H), 2.13 (d, J=13.1 Hz, 2H), 2.02-1.93 (m, 2H), 1.64-1.58 (m, 2H), 1.47 (s, 9H), 1.42-1.32 (m, 2H). LCMS (M+H)=298.2.

INTERMEDIATE 76

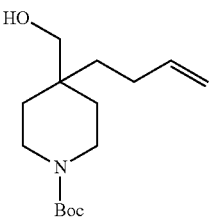 [SMILES: C=CCCC1(CO)CCN(C(=O)OC(C)(C)C)CC1]

tert-Butyl 4-(but-3-en-1-yl)-4-(hydroxymethyl)piperidine-1-carboxylate

To a solution of 1-tert-butyl 4-methyl 4-(but-3-en-1-yl) piperidine-1,4-dicarboxylate (21.2 g, 71.3 mmol) in THF (300 mL) at 0° C. was added 2M LAH/THF (35.6 mL, 71.3 mmol) and the resulting mixture was stirred at 0° C. for 1 h and then stirred at room temp for 2 h. The mixture was then recooled to 0° C. and water (2.7 mL), 1N NaOH (2.7 mL) and water (8.2 mL) were added successively and the mixture was stirred for 5 min. The solids were filtered off and the cake was washed with ethyl acetate. The filtrate was washed with water (2×50 mL), brine (100 mL), dried (Na$_2$SO$_4$), filtered and concentrated under reduced pressure to give tert-butyl 4-(but-3-en-1-yl)-4-(hydroxymethyl)piperidine-1-carboxylate (16.5 g, 61.3 mmol, 86% yield) as yellow oil. $^1$H NMR (500 MHz, CDCl$_3$) δ 5.90-5.78 (m, 1H), 5.13-5.01 (m, 1H), 5.01-4.86 (m, 1H), 3.57-3.42 (m, 4H), 3.39-3.28 (m, 2H), 2.46-2.33 (m, 1H), 2.06-1.99 (m, 2H), 1.54-1.38 (m, 14H).

INTERMEDIATE 77

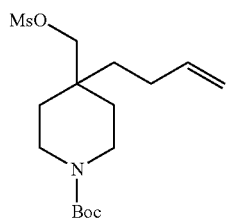

tert-Butyl 4-(but-3-en-1-yl)-4-(((methylsulfonyl)oxy)methyl)piperidine-1-carboxylate Ms-Cl (5.59 mL, 71.7 mmol) was added dropwise at 0° C. to a stirred solution of tert-butyl 4-(but-3-en-1-yl)-4-(hydroxymethyl)piperidine-1-carboxylate (16.1 g, 59.8 mmol) TEA (16.66 mL, 120 mmol) and DMAP (0.365 g, 2.99 mmol) in CH$_2$Cl$_2$ (300 mL) and the mixture was stirred at room temp for 2 h. Water was then added and the mixture was extracted with methylene chloride (100 mL), dried (Na$_2$SO$_4$), filtered and concentrated. The residue was purified by Biotage (0-40% Hex/EtOAc) to afford tert-butyl 4-(but-3-en-1-yl)-4-(((methylsulfonyl)oxy)methyl)piperidine-1-carboxylate (18 g, 51.8 mmol, 87% yield) as colorless oil. $^1$H NMR (500 MHz, CDCl$_3$) δ 5.88-5.75 (m, 1H), 5.11-4.90 (m, 2H), 4.09 (s, 2H), 3.58-3.44 (m, 2H), 3.40-3.32 (m, 2H), 3.05 (s, 3H), 2.07-2.02 (m, 2H), 1.59-1.54 (m, 2H), 1.53-1.49 (m, 4H), 1.48 (s, 9H).

INTERMEDIATE 78

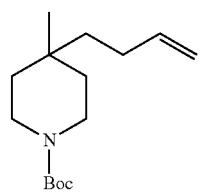 [SMILES: C=CCCC1(C)CCN(C(=O)OC(C)(C)C)CC1]

tert-Butyl 4-(but-3-en-1-yl)-4-methylpiperidine-1-carboxylate

To a solution of tert-butyl 4-(but-3-en-1-yl)-4-(((methylsulfonyl)oxy)methyl)piperidine-1-carboxylate (17 g, 48.9 mmol) in THF (250 mL) was added 1M solution of Superhydride (98 mL, 98 mmol) in THF and the resulting mixture was refluxed for 3 h. After cooling to room temp water was added and the mixture was extracted with ether (2×200 mL), washed with brine (100 mL), dried (Na$_2$SO$_4$), filtered and concentrated. The residue was purified by Biotage (0-20% EtOAc/hexane) to afford tert-butyl 4-(but-3-en-1-yl)-4-methylpiperidine-1-carboxylate (3.5 g, 13.81 mmol, 28.2% yield). $^1$H NMR (500 MHz, CDCl$_3$) δ 5.88-5.80 (m, 1H), 5.03 (dq, J=17.1, 1.7 Hz, 1H), 4.96 (ddt, J=10.2, 2.1, 1.1 Hz, 1H), 3.62-3.49 (m, 2H), 3.23 (ddd, J=13.4, 9.3, 3.8 Hz, 2H), 2.09-1.97 (m, 2H), 1.48 (s, 9H), 1.43-1.22 (m, 6H), 0.96 (s, 3H). LCMS (M+H)=254.2. 8 g of starting material was also recovered.

INTERMEDIATE 79

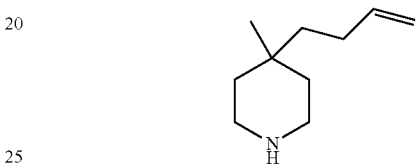

4-(But-3-en-1-yl)-4-methylpiperidine.HCl

A mixture of tert-butyl 4-(but-3-en-1-yl)-4-methylpiperidine-1-carboxylate (3.5 g, 13.81 mmol) and 4M HCl/dioxane (17.27 ml, 69.1 mmol) was stirred at room temp for 3 h. Mixture was then concentrated and dried under high vac to afford 4-(but-3-en-1-yl)-4-methylpiperidine.HCl (2.6 g, 13.70 mmol, 99% yield) as off-white solid. $^1$H NMR (500 MHz, DMSO-d$_6$) δ 5.83 (ddt, J=17.0, 10.3, 6.6 Hz, 1H), 5.05 (dq, J=17.1, 1.7 Hz, 1H), 5.00-4.80 (m, 1H), 3.11-2.90 (m, 5H), 2.05-1.90 (m, 2H), 1.56-1.42 (m, 5H), 1.38-1.26 (m, 2H), 0.95 (s, 3H). LCMS (M+H)=154.1.

INTERMEDIATE 80

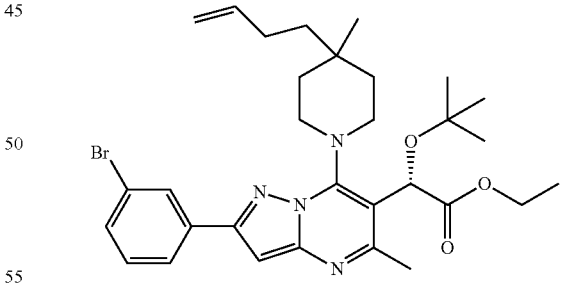

(S)-Ethyl 2-(2-(3-bromophenyl)-7-(4-(but-3-en-1-yl)-4-methylpiperidin-1-yl)-5-methylpyrazolo[1,5-a]pyrimidin-6-yl)-2-(tert-butoxy)acetate A mixture of (S)-ethyl 2-(2-(3-bromophenyl)-7-chloro-5-methylpyrazolo[1,5-a]pyrimidin-6-yl)-2-(tert-butoxy)acetate (1.7 g, 3.54 mmol),4-(but-3-en-1-yl)-4-methylpiperidine, HCl (0.872 g, 4.60 mmol), Hunig's Base (1.853 mL, 10.61 mmol) in NMP (20 mL) was heated at 60° C. for 16 h. At this point LCMS indicated completion of reaction.

Mixture was then cooled, diluted with Et₂O and washed with water (2×25 mL) and brine (25 mL), then dried (Na₂SO₄), filtered, and concentrated under reduced pressure. The residue was then purified by Biotage (5-30% EtOAc/hexane) to afford (S)-ethyl 2-(2-(3-bromophenyl)-7-(4-(but-3-en-1-yl)-4-methylpiperidin-1-yl)-5-methylpyrazolo[1,5-a]pyrimidin-6-yl)-2-(tert-butoxy)acetate (1.9 g, 3.18 mmol, 90% yield) as light yellow solid. ¹H NMR (500 MHz, CDCl₃) δ 8.17 (t, J=1.7 Hz, 1H), 7.96-7.92 (m, 1H), 7.53 (ddd, J=7.9, 2.0, 0.9 Hz, 1H), 7.37-7.32 (m, 1H), 6.81 (s, 1H), 6.06 (s, 1H), 5.95 (br. s., 1H), 5.12 (d, J=16.7 Hz, 1H), 5.03 (d, J=10.2 Hz, 1H), 4.29-4.14 (m, 3H), 2.65 (s, 3H), 2.20-2.11 (m, 2H), 1.84-1.70 (m, 1H), 1.64 (t, J=5.6 Hz, 2H), 1.55 (dd, J=12.9, 3.3 Hz, 2H), 1.28 (s, 9H), 1.26-1.22 (m, 3H), 1.18 (br. s., 3H). 4 missing piperidine hydrogens. LCMS (M+2H)=599.4.

INTERMEDIATE 81

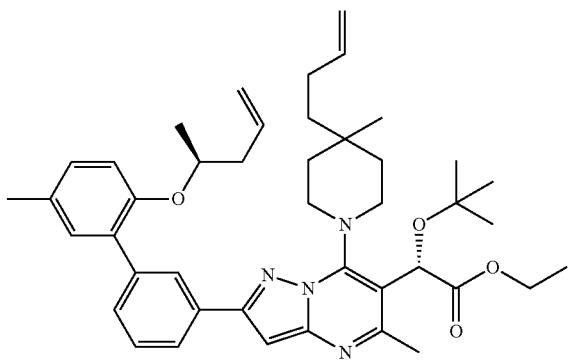

(S)-Ethyl 2-(7-(4-(but-3-en-1-yl)-4-methylpiperidin-1-yl)-5-methyl-2-(5'-methyl-2'-((S)-pent-4-en-2-yloxy)-[1,1'-biphenyl]-3-yl)pyrazolo[1,5-a]pyrimidin-6-yl)-2-(tert-butoxy)acetate A solution of ((S)-ethyl 2-(2-(3-bromophenyl)-7-(4-(but-3-en-1-yl)-4-methylpiperidin-1-yl)-5-methylpyrazolo[1,5-a]pyrimidin-6-yl)-2-(tert-butoxy)acetate (200 mg, 0.335 mmol), (S)-4,4,5,5-tetramethyl-2-(5-methyl-2-(pent-4-en-2-yloxy)phenyl)-1,3,2-dioxaborolane (152 mg, 0.502 mmol) and 2.0 M Na₂CO₃ (0.418 mL, 0.837 mmol) in DMF (5 mL) was degassed for 10 min. Pd(Ph₃P)₄ (27.1 mg, 0.023 mmol) was then added and the degassing was continued for another 5 min. The reaction was then heated at 90° C. for 3 hrs. At this point LCMS indicated completion of reaction. The mixture was then cooled to room temp and diluted with water (10 mL) and extracted with Et₂O (2×25 mL). The combined extracts were dried (Na₂SO₄), filtered, and concentrated under reduced pressure, and the residue was purified by biotage (0-25% EtOAc/hexane) to afford (S)-ethyl 2-(7-(4-(but-3-en-1-yl)-4-methylpiperidin-1-yl)-5-methyl-2-(5'-methyl-2'-((S)-pent-4-en-2-yloxy)-[1,1'-biphenyl]-3-yl)pyrazolo[1,5-a]pyrimidin-6-yl)-2-(tert-butoxy)acetate (190 mg, 0.274 mmol, 82% yield) as white foam. ¹H NMR (500 MHz, CDCl₃) δ 8.19 (s, 1H), 8.02 (d, J=7.4 Hz, 1H), 7.60 (d, J=7.6 Hz, 1H), 7.49 (t, J=7.7 Hz, 1H), 7.26 (d, J=1.9 Hz, 1H), 7.14 (dd, J=8.3, 1.7 Hz, 1H), 6.95 (d, J=8.4 Hz, 1H), 6.86 (s, 1H), 6.09 (s, 1H), 5.95-5.75 (m, 2H), 5.73 (s, 1H), 5.24-5.15 (m, 1H), 5.13-4.95 (m, 4H), 4.38-4.30 (m, 1H), 4.28-4.12 (m, 2H), 2.65 (s, 3H), 2.58-2.40 (m, 3H), 2.38 (s, 3H), 2.28 (dt, J=14.0, 6.9 Hz, 1H), 2.13 (br. s., 2H), 1.67-1.61 (m, 2H), 1.28 (s, 9H), 1.24-1.22 (m, 6H), 1.17 (d, J=19.2 Hz, 3H). 4 missing piperidine hydrogens. LCMS (M+H)=694.6.

EXAMPLE 20

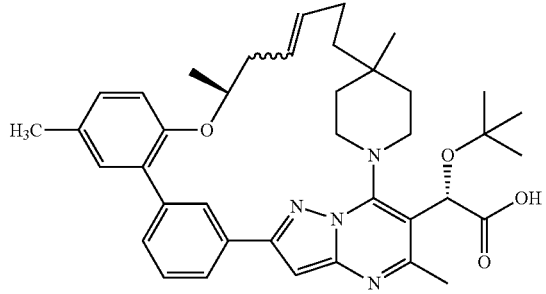 [SMILES: Cc1ccc2c(c1)-c1cccc(c1)-c1cc3nc(C)c([C@H](OC(C)(C)C)C(=O)O)c(n3n1)N1CCC(C)(CCC=CC[C@@H](C)O2)CC1]

(2S)-2-(tert-Butoxy)-2-[(22S)-4,17,22,28-tetramethyl-21-oxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33),11,13,15(20),16,18,24-undecaen-3-yl]acetic acid To a solution of (S)-ethyl 2-(7-(4-(but-3-en-1-yl)-4-methylpiperidin-1-yl)-5-methyl-2-(5'-methyl-2'-((S)-pent-4-en-2-yloxy)-[1,1'-biphenyl]-3-yl)pyrazolo[1,5-a]pyrimidin-6-yl)-2-(tert-butoxy)acetate (200 mg, 0.289 mmol) in DCE (200 mL) at room temp was added CuI (55.0 mg, 0.289 mmol) followed by (1,3-dimesitylimidazolidin-2-ylidene)(2-isopropoxybenzylidene)ruthenium(VI) chloride (18.09 mg, 0.029 mmol) and the resulting mixture was heated at 80° C. for 2 h. At this point LCMS indicated completion of reaction and mixture of isomers (cis and trans). Mixture was then cooled and concentrated to afford brown solid which was treated with 1N NaOH (0.301 mL, 0.301 mmol) in MeOH (1 mL) at 75° C. for 3 h. Mixture was then cooled and purified by prep HPLC to afford isomer 1 (9.4 mg, 0.015 mmol, 24.54% yield) first eluting: ¹H NMR (600 MHz, DMSO-d₆) δ 8.44 (s, 1H), 7.86 (d, J=7.3 Hz, 1H), 7.53 (t, J=7.5 Hz, 1H), 7.38 (d, J=7.7 Hz, 1H), 7.16 (s, 1H), 7.14 (d, J=8.4 Hz, 1H), 7.08 (d, J=8.4 Hz, 1H), 7.00 (s, 1H), 5.75-5.65 (m, 1H), 5.52 (br. s., 1H), 5.49-5.39 (m, 1H), 4.56 (br. s., 1H), 4.15 (t, J=12.3 Hz, 1H), 3.13 (d, J=11.7 Hz, 1H), 2.76 (d, J=13.6 Hz, 1H), 2.50 (s, 3H), 2.29 (s, 3H), 2.25-2.17 (m, 1H), 2.12 (d, J=8.4 Hz, 1H), 1.91 (s, 1H), 1.86 (d, J=10.6 Hz, 2H), 1.81-1.72 (m, 1H), 1.71-1.60 (m, 1H), 1.50 (d, J=12.8 Hz, 1H), 1.41 (t, J=11.0 Hz, 1H), 1.25 (t, J=11.2 Hz, 2H), 1.16 (s, 12H), 1.00 (s, 3H). LCMS (M+H)=637.6 and isomer 2 (2.2 mg, 3.45 μmol, 5.74% yield) second eluting: ¹H NMR (600 MHz, DMSO-d₆) δ 8.00 (s, 1H), 7.86 (d, J=7.7 Hz, 1H), 7.50 (t, J=7.7 Hz, 1H), 7.23 (d, J=7.3 Hz, 1H), 7.12 (d, J=8.1 Hz, 1H), 7.04-7.01 (m, 2H), 6.92 (s, 1H), 5.87 (br. s., 1H), 5.60-5.49 (m, 2H), 4.64 (t, J=12.1 Hz, 1H), 4.42 (br. s., 1H), 3.14 (br. s., 1H), 2.65 (d, J=11.0 Hz, 1H), 2.53 (s, 3H), 2.48-2.40 (m, 1H), 2.25 (s, 3H), 2.12-2.04 (m, 1H), 2.04-1.94 (m, 1H), 1.93-1.79 (m, 2H), 1.58 (d, J=12.1 Hz, 2H), 1.49 (t, J=12.7 Hz, 2H), 1.31-1.22 (m, 2H), 1.19 (s, 9H), 1.09 (d, J=5.9 Hz, 3H), 0.92 (s, 3H). LCMS (M+H)=637.5.

EXAMPLE 21

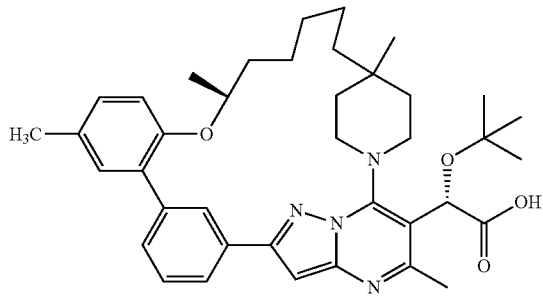 [SMILES: Cc1ccc2c(c1)-c1cccc(c1)-c1cc3nc(C)c([C@H](OC(C)(C)C)C(=O)O)c(n3n1)N1CCC(C)(CCCCC[C@@H](C)O2)CC1]

(2S)-2-(tert-Butoxy)-2-[(22S)-4,17,22,28-tetramethyl-21-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid To a solution of (2S)-2-(tert-butoxy)-2-[(22S)-4,17,22,28-tetramethyl-21-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid (100 mg, 0.157 mmol) in MeOH (3 mL) was added 10% Pd/C (16.71 mg, 0.016 mmol) and the mixture was stirred under balloon hydrogen atmosphere for 5 h. Mixture was then filtered and purified by prep HPLC to afford (2S)-2-(tert-butoxy)-2-[(22S)-4,17,22,28-tetramethyl-21-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid (16.2 mg, 0.025 mmol, 16.15% yield). $^1$H NMR (500 MHz, CDCl$_3$) δ 8.46 (s, 1H), 7.78 (d, J=7.7 Hz, 1H), 7.54-7.46 (m, 1H), 7.38 (d, J=7.7 Hz, 1H), 7.18-7.11 (m, 2H), 6.94 (d, J=8.2 Hz, 1H), 6.90 (s, 1H), 5.95 (br. s., 1H), 4.62-4.54 (m, 1H), 4.45-4.35 (m, 1H), 3.78-3.65 (m, 2H), 3.50 (d, J=12.5 Hz, 1H), 2.88 (q, J=7.3 Hz, 2H), 2.62 (s, 3H), 2.37 (s, 3H), 2.26-2.13 (m, 3H), 1.81-1.59 (m, 4H), 1.48-1.38 (m, 2H), 1.30 (s, 9H), 1.29-1.23 (m, 3H), 1.15 (d, J=6.0 Hz, 3H), 0.99 (s, 3H). LCMS (M+H)=639.6.

INTERMEDIATE 82

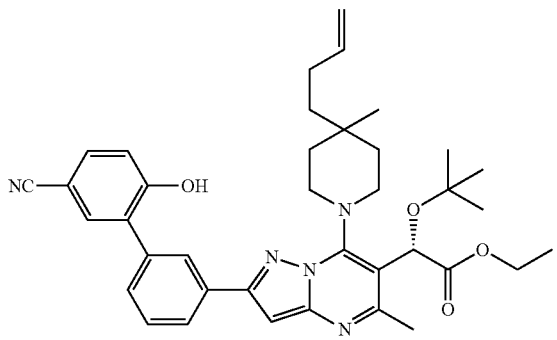 [SMILES: C=CCCC1(C)CCN(c2c([C@H](OC(C)(C)C)C(=O)OCC)c(C)nc3cc(-c4cccc(-c5cc(C#N)ccc5O)c4)nn23)CC1]

(S)-Ethyl 2-(7-(4-(but-3-en-1-yl)-4-methylpiperidin-1-yl)-2-(5'-cyano-2'-hydroxy-[1,1'-biphenyl]-3-yl)-5-methylpyrazolo[1,5-a]pyrimidin-6-yl)-2-(tert-butoxy)acetate A solution of ((S)-ethyl 2-(2-(3-bromophenyl)-7-(4-(but-3-en-1-yl)-4-methylpiperidin-1-yl)-5-methylpyrazolo[1,5-a]pyrimidin-6-yl)-2-(tert-butoxy)acetate (200 mg, 0.335 mmol), (5-cyano-2-hydroxyphenyl)boronic acid (82 mg, 0.502 mmol) and 2.0 M Na$_2$CO$_3$ (0.418 mL, 0.837 mmol) in DMF (5 mL) was degassed for 10 min. Pd(Ph$_3$P)$_4$ (27.1 mg, 0.023 mmol), was added and the degassing was continued for another 5 min. The reaction was then heated at 90° C. for 3 hrs. At this point LCMS indicated completion of reaction. The mixture was then cooled to room temp and diluted with water (10 mL) and extracted with ethyl acetate (50 mL), dried (Na$_2$SO$_4$), filtered, and concentrated under reduced pressure, and the residue was purified by biotage (0-45% EtOAc/hexane) to afford (S)-ethyl 2-(7-(4-(but-3-en-1-yl)-4-methylpiperidin-1-yl)-2-(5'-cyano-2'-hydroxy-[1,1'-biphenyl]-3-yl)-5-methylpyrazolo[1,5-a]pyrimidin-6-yl)-2-(tert-butoxy)acetate (150 mg, 0.236 mmol, 70.5% yield) as white foam. $^1$H NMR (500 MHz, CDCl$_3$) δ 8.13 (t, J=1.6 Hz, 1H), 8.08 (dt, J=7.8, 1.4 Hz, 1H), 7.66 (d, J=2.0 Hz, 1H), 7.62-7.55 (m, 2H), 7.46 (d, J=7.7 Hz, 1H), 7.17 (br. s., 1H), 7.14-7.10 (m, 1H), 6.85 (s, 1H), 6.07-6.01 (m, 1H), 5.89 (ddt, J=16.8, 10.3, 6.5 Hz, 1H), 5.08 (d, J=17.0 Hz, 1H), 4.97 (d, J=10.1 Hz, 1H), 4.31-4.11 (m, 3H), 2.63 (s, 3H), 2.12 (br. s., 2H), 1.76 (br. s., 1H), 1.67-1.62 (m, 2H), 1.58-1.51 (m, 2H), 1.28 (s, 9H), 1.25 (t, J=7.1 Hz, 3H), 1.16 (br. s., 3H). 4 missing piperidine hydrogens. LCMS (M+H)=636.6.

INTERMEDIATE 83

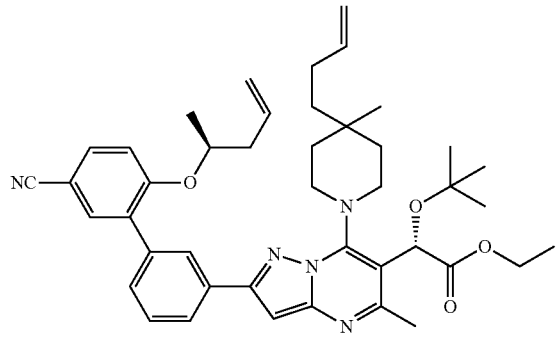 [SMILES: C=CCCC1(C)CCN(c2c([C@H](OC(C)(C)C)C(=O)OCC)c(C)nc3cc(-c4cccc(-c5cc(C#N)ccc5O[C@@H](C)CC=C)c4)nn23)CC1]

(S)-Ethyl 2-(7-(4-(but-3-en-1-yl)-4-methylpiperidin-1-yl)-2-(5'-cyano-2'-((S)-pent-4-en-2-yloxy)-[1,1'-biphenyl]-3-yl)-5-methylpyrazolo[1,5-a]pyrimidin-6-yl)-2-(tert-butoxy)acetate To a solution of (S)-ethyl 2-(7-(4-(but-3-en-1-yl)-4-methylpiperidin-1-yl)-2-(5'-cyano-2'-hydroxy-[1,1'-biphenyl]-3-yl)-5-methylpyrazolo[1,5-a]pyrimidin-6-yl)-2-(tert-butoxy)acetate (150 mg, 0.236 mmol) and (R)-pent-4-en-2-ol (61.0 mg, 0.708 mmol) in THF (3 mL) was added Ph$_3$P (186 mg, 0.708 mmol) follows by DEAD (0.112 mL, 0.708 mmol) and the resulting mixture was stirred at room temp for 16 h. Water (10 mL) was then added and the mixture was extracted with EtOAc (50 mL), washed with brine (10 mL), dried (Na$_2$SO$_4$), filtered and concentrated. The residue was then purified via Biotage (0-10% EtOAc/hexane) to afford (S)-ethyl 2-(7-(4-(but-3-en-1-yl)-4-methylpiperidin-1-yl)-2-(5'-cyano-2'-((S)-pent-4-en-2-yloxy)-[1,1'-biphenyl]-3-yl)-5-methylpyrazolo[1,5-a]pyrimidin-6-yl)-2-(tert-butoxy)acetate (150 mg, 0.213 mmol, 90% yield) as light yellow oil. $^1$H NMR (500 MHz, CDCl$_3$) δ 8.13 (s, 1H), 8.07 (d, J=2.0 Hz, 1H), 7.72 (d, J=2.0 Hz, 1H), 7.65 (dd, J=8.6, 2.1 Hz, 1H), 7.53 (d, J=5.2 Hz, 2H), 7.10-7.01 (m, 1H), 6.86-

6.84 (m, 1H), 6.18 (br. s., 1H), 6.09 (s, 1H), 5.88 (d, J=5.5 Hz, 1H), 5.77 (ddt, J=17.4, 9.9, 7.1 Hz, 2H), 5.17-5.02 (m, 5H), 4.30-4.08 (m, 5H), 2.66 (s, 3H), 2.47 (dt, J=13.2, 6.6 Hz, 1H), 2.36 (dt, J=13.8, 6.7 Hz, 1H), 2.21 (br. s., 1H), 2.13 (br. s., 2H), 1.75 (br. s., 1H), 1.64 (t, J=5.4 Hz, 2H), 1.29 (s, 9H), 1.25 (t, J=7.1 Hz, 3H), 1.19 (d, J=6.1 Hz, 3H) 4 missing piperidine hydrogens. LCMS (M+H)=704.6.

INTERMEDIATE 84

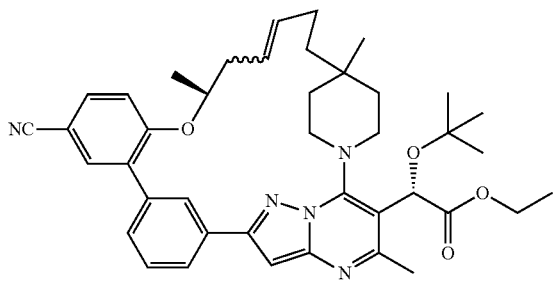 [SMILES: CCOC(=O)[C@@H](OC(C)(C)C)c1c(C)nc2cc3nn2c1N1CCC(C)(CCC=CC[C@@H](C)Oc2ccc(C#N)cc2-c2cccc-3c2)CC1]

Ethyl (2S)-2-(tert-butoxy)-2-[(22S)-17-cyano-4,22, 28-trimethyl-21-oxa-1,5,7,8-tetraazahexacyclo [26.2.2.1$^{6,9}$.1$^{10,14}$.0$^{2,7}$.0$^{15,20}$]tetratriaconta-2,4,6(34), 8,10(33),11,13,15(20),16,18,24-undecaen-3-yl] acetate To a solution of (S)-ethyl 2-(7-(4-(but-3-en-1-yl)-4-methylpiperidin-1-yl)-2-(5'-cyano-2'-((S)-pent-4-en-2-yloxy)-[1, 1'-biphenyl]-3-yl)-5-methylpyrazolo[1,5-a]pyrimidin-6-yl)-2-(tert-butoxy)acetate (150 mg, 0.213 mmol) in DCE (150 mL) at room temp was added CuI (40.6 mg, 0.213 mmol) followed by (1,3-dimesitylimidazolidin-2-ylidene)(2-isopropoxybenzylidene)ruthenium(VI) chloride (13.35 mg, 0.021 mmol) and the resulting mixture was heated at 85° C. for 3 h. At this point LCMS indicated completion of reaction. Mixture was then cooled to room temp, filtered and concentrated to afford brown solid (mixture of cis and trans isomers) which was used as is in the next step without further purification. LCMS (M+H)=676.6.

EXAMPLE 22

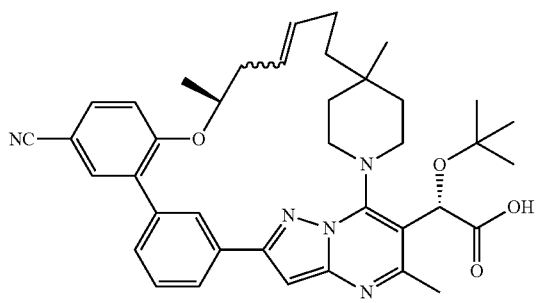 [SMILES: Cc1nc2cc3nn2c(c1[C@H](OC(C)(C)C)C(=O)O)N1CCC(C)(CCC=CC[C@@H](C)Oc2ccc(C#N)cc2-c2cccc-3c2)CC1]

(2S)-2-(tert-Butoxy)-2-[(22S)-17-cyano-4,22,28-trimethyl-21-oxa-1,5,7,8-tetraazahexacyclo [26.2.2.1$^{6,9}$.1$^{10,14}$.0$^{2,7}$.0$^{15,20}$]tetratriaconta-2,4,6(34), 8,10(33),11,13,15(20),16,18,24-undecaen-3-yl]acetic acid To a solution of ethyl (2S)-2-(tert-butoxy)-2-[(22S)-17-cyano-4,22,28-trimethyl-21-oxa-1,5,7,8-tetraazahexacyclo [26.2.2.1$^{6,9}$.1$^{10,14}$.0$^{2,7}$.0$^{15,20}$]tetratriaconta-2,4,6(34),8,10 (33),11,13,15(20),16,18,24-undecaen-3-yl]acetate (40 mg, 0.059 mmol) in MeOH (3 mL) was added 25 wt % MeONa in methanol (0.054 mL, 0.237 mmol) and the resulting mixture was heated at 50° C. for 2 h. At this point LCMS indicated complete conversion to methyl ester. 1M LiOH (0.355 mL, 0.355 mmol) was then added and the mixture was heated at 70° C. for 1 h. Mixture was then cooled and purified by prep HPLC to afford first eluting isomer 1 (8 mg, 0.012 mmol, 20.87% yield). $^1$H NMR (600 MHz, DMSO-d$_6$) δ 8.43 (s, 1H), 7.93 (d, J=7.7 Hz, 1H), 7.85-7.74 (m, 2H), 7.56 (t, J=7.7 Hz, 1H), 7.45 (d, J=7.3 Hz, 1H), 7.41 (d, J=8.8 Hz, 1H), 7.00 (s, 1H), 5.71 (d, J=7.0 Hz, 1H), 5.48-5.32 (m, 2H), 4.85-4.75 (m, 1H), 4.10 (t, J=12.5 Hz, 1H), 3.16 (d, J=12.8 Hz, 1H), 2.90-2.82 (m, 1H), 2.77 (d, J=13.6 Hz, 1H), 2.55 (s, 2H), 2.49 (s, 3H), 2.34-2.24 (m, 1H), 2.14 (d, J=12.1 Hz, 1H), 1.88-1.69 (m, 2H), 1.44 (d, J=12.5 Hz, 1H), 1.41-1.32 (m, 1H), 1.26 (d, J=5.5 Hz, 3H), 1.16 (d, J=7.7 Hz, 2H), 1.13 (s, 9H), 0.96 (s, 3H). LCMS (M+H)=648.5. Second eluting isomer 2 (12.4 mg, 0.019 mmol, 32.3% yield). $^1$H NMR (600 MHz, DMSO-d$_6$) δ 7.99 (s, 1H), 7.92 (d, J=7.7 Hz, 1H), 7.82 (d, J=8.8 Hz, 1H), 7.59-7.49 (m, 2H), 7.37 (d, J=8.8 Hz, 1H), 7.24 (d, J=7.7 Hz, 1H), 7.03 (s, 1H), 5.79 (s, 1H), 5.60-5.41 (m, 2H), 4.73-4.55 (m, 2H), 3.23-3.17 (m, 4H), 2.85 (q, J=6.8 Hz, 1H), 2.63 (d, J=10.6 Hz, 1H), 2.55 (s, 1H), 2.53 (s, 3H), 2.17-2.08 (m, 1H), 2.08-1.98 (m, 1H), 1.91-1.80 (m, 3H), 1.60-1.52 (m, 2H), 1.47 (q, J=13.1 Hz, 2H), 1.13 (s, 9H), 0.91 (s, 3H). LCMS (M+H)=648.5.

EXAMPLES 23 and 24

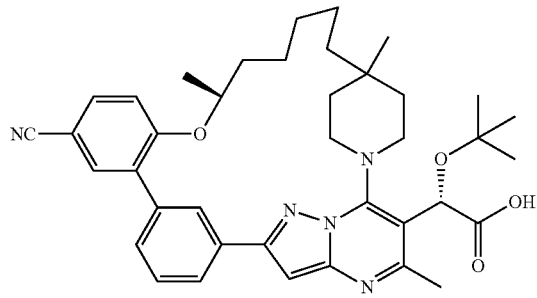

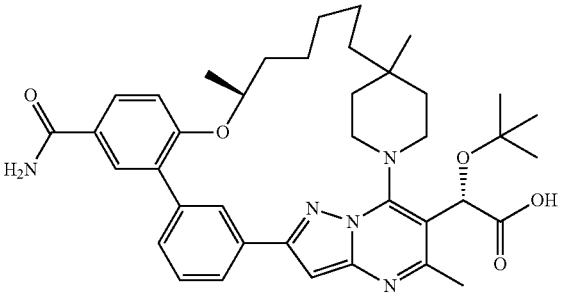

(2S)-2-(tert-Butoxy)-2-[(22S)-17-cyano-4,22,28-trimethyl-21-oxa-1,5,7,8-tetraazahexacyclo [26.2.2.1$^{6,9}$.1$^{10,14}$.0$^{2,7}$.0$^{15,20}$]tetratriaconta-2,4,6(34), 8,10(33),11,13,15(20),16,18-decaen-3-yl]acetic acid and (2S)-2-(tert-butoxy)-2-[(22S)-17-carbamoyl-4, 22,28-trimethyl-21-oxa-1,5,7,8-tetraazahexacyclo [26.2.2.1$^{6,9}$.1$^{10,14}$.0$^{2,7}$.0$^{15,20}$]tetratriaconta-2,4,6(34), 8,10(33),11,13,15(20),16,18-decaen-3-yl]acetic acid To a solution of (2S)-2-(tert-butoxy)-2-[(22S)-17-cyano-4,22,28-trimethyl-21-oxa-1,5,7,8-tetraazahexacyclo

[26.2.2.1$^{6,9}$.1$^{10,14}$.0$^{2,7}$.0$^{15,20}$]tetratriaconta-2,4,6(34),8,10 (33),11,13,15(20),16,18,24-undecaen-3-yl]acetic acid (80 mg, 0.123 mmol) in MeOH (2 mL) and CH$_2$Cl$_2$ (2 mL) was added 10% Pd/C (13.14 mg, 0.012 mmol) and the resulting mixture was stirred under balloon hydrogen atmosphere for 3 h. Mixture was then filtered through celite and purified by HPLC to afford second eluting (2S)-2-(tert-butoxy)-2-[(22S)-17-cyano-4,22,28-trimethyl-21-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid (27.5 mg, 0.042 mmol, 34.3% yield). $^1$H NMR (600 MHz, DMSO-d$_6$) δ 8.30 (s, 1H), 7.98 (d, J=7.3 Hz, 1H), 7.82 (d, J=8.4 Hz, 1H), 7.69 (br. s., 1H), 7.56 (t, J=7.7 Hz, 1H), 7.38-7.31 (m, 2H), 7.12 (s, 1H), 5.75 (br. s., 1H), 4.74 (d, J=5.5 Hz, 1H), 4.38 (t, J=12.3 Hz, 1H), 2.80 (d, J=11.4 Hz, 1H), 2.49 (s, 3H), 1.75-1.62 (m, 4H), 1.62-1.51 (m, 4H), 1.48-1.41 (m, 2H), 1.38 (br. s., 3H), 1.34-1.25 (m, 3H), 1.17 (s, 9H), 1.14 (d, J=5.5 Hz, 3H), 0.92 (br. s., 3H). LCMS (M+H)=650.5 and first eluting (2S)-2-(tert-butoxy)-2-[(22S)-17-carbamoyl-4,22,28-trimethyl-21-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid (6.4 mg, 9.58 μmol, 7.76% yield). $^1$H NMR (600 MHz, DMSO-d$_6$) δ 8.34 (s, 1H), 7.96 (d, J=7.3 Hz, 1H), 7.88 (s, 1H), 7.90 (s, 1H), 7.83-7.78 (m, 1H), 7.56 (t, J=7.5 Hz, 1H), 7.37 (d, J=7.3 Hz, 1H), 7.23 (d, J=8.8 Hz, 1H), 7.18 (br. s., 1H), 7.12 (s, 1H), 5.76 (br. s., 1H), 4.74-4.64 (m, 1H), 4.40 (t, J=11.7 Hz, 1H), 3.58-3.38 (m, 1H), 2.81 (d, J=11.0 Hz, 1H), 2.49 (s, 3H), 1.71-1.55 (m, 8H), 1.49-1.32 (m, 7H), 1.18 (s, 9H), 1.14 (d, J=5.5 Hz, 3H), 0.93 (br. s., 3H). LCMS (M+H)=668.6.

INTERMEDIATE 85

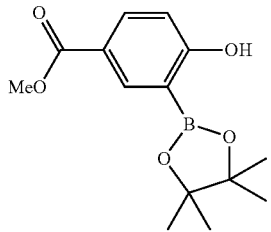 [SMILES: COC(=O)c1ccc(O)c(B2OC(C)(C)C(C)(C)O2)c1]

Methyl 4-hydroxy-3-(4,4,5,5-tetramethyl-1,3,2-dioxaborolan-2-yl)benzoate

A mixture of methyl 3-bromo-4-hydroxybenzoate (3 g, 12.98 mmol), bis(pinacolateo)diboron (6.59 g, 26.0 mmol), 1,1'-bis(diphenylphosphine)ferrocene (0.360 g, 0.649 mmol) and KOAc (3.82 g, 39.0 mmol) in 1,4-dioxane (70 mL) was sparged with N$_2$ for 15 min. Then, 1,1-bis(diphenylphosphino)ferrocene]dichloropalladium(II) CH$_2$Cl$_2$ complex (0.530 g, 0.649 mmol) was added, sparged for additional 5 min and heated at 85° C. for 16 h. Then, cooled, diluted with Et$_2$O (250 mL), washed with water (4×50 mL), brine (25 mL), dried (Na$_2$SO$_4$), filtered and concentrated to give brow paste which was purified by flash chromatography (5-25% EtOAc/hexane) to afford methyl 4-hydroxy-3-(4,4,5,5-tetramethyl-1,3,2-dioxaborolan-2-yl)benzoate (1.2 g, 4.31 mmol, 33.2% yield) as white solid. $^1$H NMR (500 MHz, CDCl$_3$) δ 8.36 (d, J=2.4 Hz, 1H), 8.30-8.21 (m, 1H), 8.13-8.02 (m, 1H), 6.93 (d, J=8.7 Hz, 1H), 3.90 (s, 3H), 1.41 (s, 12H).

INTERMEDIATE 86

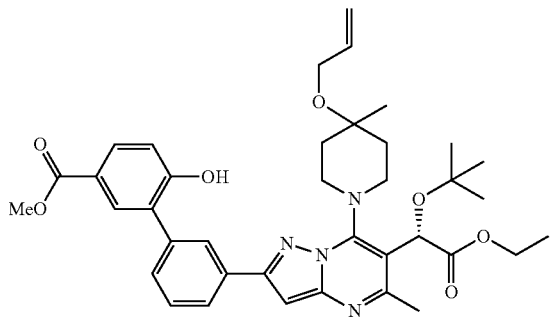 [SMILES: C=CCOC1(C)CCN(c2c([C@H](OC(C)(C)C)C(=O)OCC)c(C)nc3cc(-c4cccc(-c5cc(C(=O)OC)ccc5O)c4)nn23)CC1]

(S)-Methyl 3'-(7-(4-(allyloxy)-4-methylpiperidin-1-yl)-6-(1-(tert-butoxy)-2-ethoxy-2-oxoethyl)-5-methylpyrazolo[1,5-a]pyrimidin-2-yl)-6-hydroxy-[1,1'-biphenyl]-3-carboxylate A solution of ((S)-ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (500 mg, 0.834 mmol), methyl 4-hydroxy-3-(4,4,5,5-tetramethyl-1,3,2-dioxaborolan-2-yl)benzoate (348 mg, 1.251 mmol) and 2.0 M Na$_2$CO$_3$ (1.042 mL, 2.085 mmol) in DMF (10 mL) was degassed for 10 min. Pd(Ph$_3$P)$_4$ (67.5 mg, 0.058 mmol), was added and the degassing was continued for another 5 min. The reaction was then heated at 90° C. for 3 hrs. At this point LCMS indicated completion of reaction. The mixture was then cooled to room temp and diluted with water (25 mL) and extracted with Et$_2$O (2×50 mL). The combined extracts were dried (Na$_2$SO$_4$), filtered, and concentrated under reduced pressure, and the residue was purified by biotage (0-25% EtOAc/hexane) to afford (S)-methyl 3'-(7-(4-(allyloxy)-4-methylpiperidin-1-yl)-6-(1-(tert-butoxy)-2-ethoxy-2-oxoethyl)-5-methylpyrazolo[1,5-a]pyrimidin-2-yl)-6-hydroxy-[1,1'-biphenyl]-3-carboxylate (480 mg, 0.716 mmol, 86% yield) as white foam. $^1$H NMR (500 MHz, CDCl$_3$) δ 8.16-8.12 (m, 1H), 8.09-8.04 (m, 2H), 8.03-7.98 (m, 1H), 7.61-7.56 (m, 1H), 7.52-7.45 (m, 1H), 7.09 (d, J=8.5 Hz, 1H), 6.88 (br. s., 1H), 6.07-5.85 (m, 2H), 5.45-5.34 (m, 1H), 5.11 (br. s., 1H), 4.32-4.18 (m, 2H), 4.01 (d, J=4.9 Hz, 2H), 3.92 (s, 3H), 2.64 (s, 3H), 2.05-1.95 (m, 2H), 1.74 (br. s., 1H), 1.63 (br. s., 3H), 1.39-1.32 (m, 3H), 1.28-1.25 (m, 15H). LCMS (M+H)=671.6.

INTERMEDIATE 87

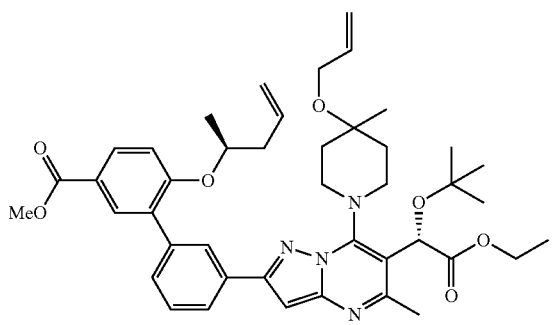 [SMILES: C=CCOC1(C)CCN(c2c([C@H](OC(C)(C)C)C(=O)OCC)c(C)nc3cc(-c4cccc(-c5cc(C(=O)OC)ccc5O[C@@H](C)CC=C)c4)nn23)CC1]

Methyl 3'-(7-(4-(but-3-en-1-yl)-4-methylpiperidin-1-yl)-6-((S)-1-(tert-butoxy)-2-ethoxy-2-oxoethyl)-5-methylpyrazolo[1,5-a]pyrimidin-2-yl)-6-((S)-pent-4-en-2-yloxy)-[1,1'-biphenyl]-3-carboxylate To a solution of (S)-methyl 3'-(7-(4-(but-3-en-1-yl)-4-methylpiperidin-1-yl)-6-(1-(tert-butoxy)-2-ethoxy-2-oxoethyl)-5-methylpyrazolo[1,5-a]pyrimidin-2-yl)-6-hydroxy-[1,1'-biphenyl]-3-carboxylate (480 mg, 0.718 mmol) and (R)-pent-4-en-2-ol (185 mg, 2.153 mmol) in THF (8 mL) was added Ph$_3$P (565 mg, 2.153 mmol) follows by DEAD (0.341 mL, 2.153 mmol) and the resulting mixture was stirred at room temp for 3 h. Water (10 mL) was then added and the mixture was extracted with ether (50 mL), washed with brine (10 mL), dried (Na$_2$SO$_4$), filtered and concentrated. The residue was then purified via Biotage (0-20% EtOAc/hexane) to afford methyl 3'-(7-(4-(but-3-en-1-yl)-4-methylpiperidin-1-yl)-6-((S)-1-(tert-butoxy)-2-ethoxy-2-oxoethyl)-5-methylpyrazolo[1,5-a]pyrimidin-2-yl)-6-((S)-pent-4-en-2-yloxy)-[1,1'-biphenyl]-3-carboxylate (450 mg, 0.611 mmol, 85% yield) as white solid. $^1$H NMR (500 MHz, CDCl$_3$) δ 8.16-8.10 (m, 2H), 8.09-8.00 (m, 2H), 7.56 (br. s., 1H), 7.51 (t, J=7.6 Hz, 1H), 7.04 (d, J=8.7 Hz, 1H), 6.87 (br. s., 1H), 6.05-5.95 (m, 1H), 5.85-5.73 (m, 2H), 5.41 (dd, J=17.1, 1.5 Hz, 1H), 5.17-5.02 (m, 4H), 4.59 (sxt, J=6.1 Hz, 1H), 4.29-4.17 (m, 4H), 4.02 (d, J=4.6 Hz, 2H), 3.93 (s, 3H), 2.67 (br. s., 2H), 2.53-2.43 (m, 1H), 2.40-2.30 (m, 2H), 2.20 (br. s., 1H), 2.04 (d, J=15.4 Hz, 2H), 1.75 (br. s., 1H), 1.35-1.32 (m, 3H), 1.32-1.24 (m, 15H), 1.21-1.15 (m, 3H). LCMS (M+H)=737.6.

INTERMEDIATE 88

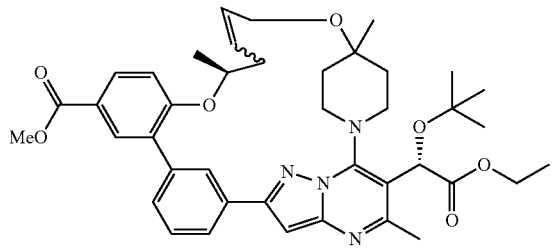 [SMILES: CCOC(=O)[C@@H](OC(C)(C)C)c1c(C)nc2cc3nn2c1N1CCC(C)(CC1)OCC=CC[C@H](C)Oc1ccc(C(=O)OC)cc1-c1cccc-3c1]

Methyl (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaene-17-carboxylate To a solution of methyl 3'-(7-(4-(allyloxy)-4-methylpiperidin-1-yl)-6-((S)-1-(tert-butoxy)-2-ethoxy-2-oxoethyl)-5-methylpyrazolo[1,5-a]pyrimidin-2-yl)-6-((S)-pent-4-en-2-yloxy)-[1,1'-biphenyl]-3-carboxylate (450 mg, 0.609 mmol) in DCE (400 mL) at room temp was added CuI (116 mg, 0.609 mmol) followed by (1,3-dimesitylimidazolidin-2-ylidene)(2-isopropoxybenzylidene)ruthenium(VI) chloride (38.2 mg, 0.061 mmol) and the resulting mixture was heated at 80° C. for 3 h. At this point LCMS indicated completion of reaction. Mixture was then cooled to room temp, filtered and concentrated to afford brown solid which was purified by biotage (5-30% etOAc/hexane) to afford methyl (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaene-17-carboxylate (360 mg, 0.506 mmol, 83% yield) as approx 1:4 mixture of cis and trans isomer. Major isomer was transcribed $^1$H NMR (400 MHz, CDCl$_3$) δ 8.52-8.48 (m, 1H), 8.07-8.00 (m, 2H), 7.85 (d, J=8.0 Hz, 1H), 7.56-7.49 (m, 1H), 7.38-7.29 (m, 1H), 7.04-6.99 (m, 1H), 6.95 (br. s., 1H), 6.44-6.30 (m, 1H), 5.94 (br. s., 1H), 5.68 (d, J=15.6 Hz, 1H), 4.89 (t, J=11.5 Hz, 1H), 4.63 (t, J=6.5 Hz, 1H), 4.29-4.17 (m, 3H), 3.99 (br. s., 2H), 3.92-3.90 (m, 3H), 3.75 (t, J=11.4 Hz, 1H), 3.23 (d, J=10.3 Hz, 1H), 2.89 (d, J=13.3 Hz, 1H), 2.64 (s, 3H), 2.42 (br. s., 1H), 2.37-2.24 (m, 1H), 2.06-1.97 (m, 2H), 1.79-1.64 (m, 1H), 1.32 (s, 3H), 1.27-1.22 (m, 12H), 1.21-1.16 (m, 3H). LCMS (M+H)=711.6.

INTERMEDIATE 89

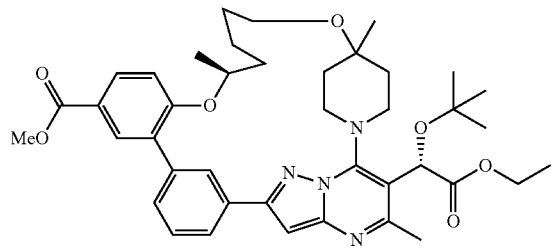 [SMILES: CCOC(=O)[C@@H](OC(C)(C)C)c1c(C)nc2cc3nn2c1N1CCC(C)(CC1)OCCCC[C@H](C)Oc1ccc(C(=O)OC)cc1-c1cccc-3c1]

Methyl (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaene-17-carboxylate To a solution of (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-undecaene-17-carboxylate (360 mg, 0.506 mmol) in Ethyl acetate (5 mL) was added 10% Pd/C (37.7 mg, 0.035 mmol) and the mixture was stirred under balloon hydrogen atmosphere for 3 h. At this point LCMS indicated completion of reaction. Mixture was then filtered through a pad of celite and the pad was washed with ethyl acetate. Filterate was then concentrated to afford methyl (22S)-3-[(1S)-1-(tert-butoxy)-2-ethoxy-2-oxo ethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaene-17-carboxylate (350 mg, 0.466 mmol, 92% yield) as off-white solid. $^1$H NMR (500 MHz, CDCl$_3$) δ 8.57 (s, 1H), 8.09-8.01 (m, 2H), 7.84 (d, J=7.9 Hz, 1H), 7.53 (t, J=7.6 Hz, 1H), 7.38 (d, J=7.6 Hz, 1H), 7.04 (d, J=8.5 Hz, 1H), 6.94 (br. s., 1H), 5.88 (br. s., 1H), 4.74-4.66 (m, 1H), 4.64-4.56 (m, 1H), 4.32-4.19 (m, 3H), 3.93 (s, 3H), 3.79 (t, J=12.0 Hz, 1H), 3.54-3.48 (m, 1H), 3.44-3.37 (m, 1H), 3.31 (d, J=12.6 Hz, 1H), 2.94 (d, J=9.8 Hz, 1H), 2.64 (s, 3H), 2.00 (d, J=12.0 Hz, 3H), 1.93-1.84 (m, 1H), 1.82-1.71 (m, 3H), 1.69-1.62 (m, 2H), 1.30-1.27 (m, 3H), 1.26-1.21 (m, 15H). LCMS (M+H)=713.6.

INTERMEDIATE 90

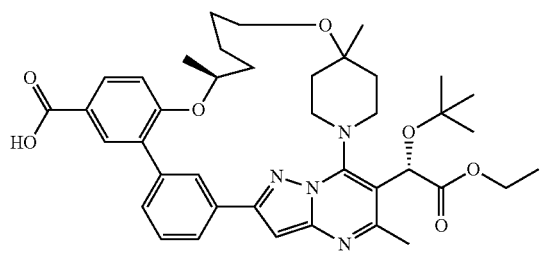 [SMILES: CCOC(=O)[C@@H](OC(C)(C)C)c1c(C)nc2cc3nn2c1N1CCC(C)(CC1)OCCCC[C@H](C)Oc1ccc(C(=O)O)cc1-c1cccc-3c1]

(22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaene-17-carboxylic acid To a solution of methyl (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaene-17-carboxylate (340 mg, 0.477 mmol) in EtOH (4 mL) and THF (4 mL) was added 1N NaOH (0.525 mL, 0.525 mmol) and the resulting mixture was stirred at room temp for 16 h. Mixture was then concentrated and purified by prep HPLC to afford (22S)-3-[(1S)-1-(tert-butoxy)-2-ethoxy-2-oxoethyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaene-17-carboxylic acid (35 mg, 0.048 mmol, 9.98% yield) third eluting on HPLC: $^1$H NMR (500 MHz, CDCl$_3$) δ 8.58 (s, 1H), 8.14-8.06 (m, 2H), 7.85 (d, J=7.9 Hz, 1H), 7.53 (t, J=7.7 Hz, 1H), 7.37 (d, J=7.7 Hz, 1H), 7.07 (d, J=9.6 Hz, 1H), 6.93 (s, 1H), 5.90 (br. s., 1H), 4.76-4.69 (m, 1H), 4.63 (t, J=12.0 Hz, 1H), 4.33-4.17 (m, 2H), 3.79 (t, J=11.7 Hz, 1H), 3.58-3.49 (m, 1H), 3.46-3.37 (m, 1H), 3.30 (d, J=11.8 Hz, 1H), 2.92 (d, J=11.0 Hz, 1H), 2.63 (s, 3H), 2.00 (d, J=13.2 Hz, 3H), 1.93-1.85 (m, 2H), 1.83-1.72 (m, 2H), 1.70-1.55 (m, 3H), 1.28 (d, J=4.6 Hz, 6H), 1.26-1.23 (m, 12H). LCMS (M+H)=699.5.

EXAMPLE 25

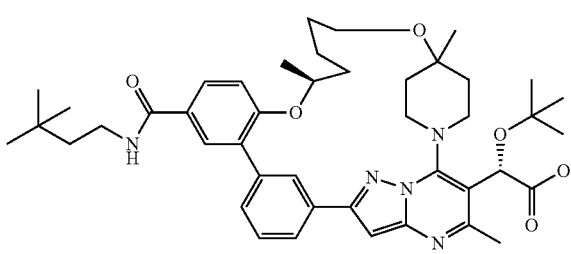 [SMILES: Cc1nc2cc3nn2c(c1[C@H](OC(C)(C)C)C(=O)O)N1CCC(C)(CC1)OCCCC[C@H](C)Oc1ccc(C(=O)NCCC(C)(C)C)cc1-c1cccc-3c1]

(2S)-2-(tert-Butoxy)-2-[(22S)-17-[(3,3-dimethylbutyl)carbamoyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid To a solution of (22S)-3-[(1S)-1-(tert-butoxy)-2-ethoxy-2-oxoethyl]-4,22,28-trimethyl-21,27-dioxa-1,5,7,8-tetraaza- hexacyclo[26.2.2.1$^{6,9}$.1$^{10,14}$.0$^{2,7}$.0$^{15,20}$]tetratriaconta-2,4,6(34),8,10(33),11,13,15(20),16,18-decaene-17-carboxylic acid (12 mg, 0.017 mmol) and 3,3-dimethylbutan-1-amine (3.48 mg, 0.034 mmol) in DMF (0.5 mL) was added DIEA (0.015 mL, 0.086 mmol) followed by HATU (13.06 mg, 0.034 mmol) and DMAP (0.210 mg, 1.717 µmol) and the resulting mixture was stirred at room temp for 3 h. Water (2 mL) was then added and the mixture was extracted with ether (10 mL), washed with brine (2 mL), dried (Na$_2$SO$_4$), filtered and concentrated. The residue was then treated with 1N NaOH (0.086 mL, 0.086 mmol) in MeOH (0.5 mL) at 70° C. for 3 h. Mixture was then cooled and purified by prep HPLC to afford (2S)-2-(tert-butoxy)-2-[(22S)-17-[(3,3-dimethylbutyl)carbamoyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid (4.8 mg, 6.37 µmol, 37.1% yield). $^1$H NMR (500 MHz, DMSO-d$_6$) δ 8.50 (s, 1H), 8.32 (t, J=5.1 Hz, 1H), 7.97 (d, J=7.7 Hz, 1H), 7.89-7.80 (m, 2H), 7.56 (t, J=7.7 Hz, 1H), 7.40 (d, J=7.3 Hz, 1H), 7.25 (d, J=8.8 Hz, 1H), 7.12 (s, 1H), 5.64 (br. s., 1H), 4.76 (d, J=5.1 Hz, 1H), 4.48 (t, J=11.9 Hz, 1H), 3.63-3.54 (m, 1H), 3.42-3.19 (m, 4H), 2.80 (d, J=10.3 Hz, 1H), 2.00-1.86 (m, 3H), 1.73 (d, J=5.1 Hz, 2H), 1.68 (br. s., 2H), 1.61-1.50 (m, 1H), 1.45 (t, J=7.9 Hz, 4H), 1.18 (s, 3H), 1.16 (s, 9H), 1.11 (d, J=5.9 Hz, 3H), 0.93 (s, 9H). 4 missing piperidine hydrogens. LCMS (M+H)=754.6.

INTERMEDIATE 91

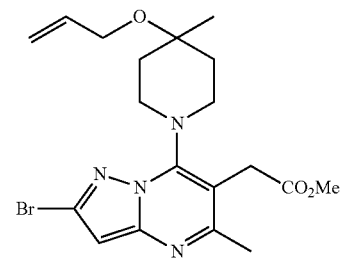 [SMILES: C=CCOC1(C)CCN(c2c(CC(=O)OC)c(C)nc3cc(Br)nn23)CC1]

Methyl 2-(7-(4-(allyloxy)-4-methylpiperidin-1-yl)-2-bromo-5-methylpyrazolo[1,5-a]pyrimidin-6-yl)acetate A solution of methyl 2-(2-bromo-7-chloro-5-methylpyrazolo[1,5-a]pyrimidin-6-yl)acetate (prepared according to the procedure for intermediate 4 starting from 3-bromo-1H-pyrazol-5-amine, 13.4 g, 41.9 mmol, 1 equiv), 4-(allyloxy)-4-methylpiperidine (7.16 g, 46.1 mmol, 1.1 equiv) and DIEA (17.6 mL, 101 mmol, 2.4 equiv) in DMF (84 mL) was heated at 60° C. for 2 h. The reaction was then added to water and extracted with ether (×2). Combined ether extracts dried (MgSO$_4$) and concentrated in vacuo. The crude product was purified by silica gel flash chromatography (0-50% EtOAc/hex) to provide methyl 2-(7-(4-(allyloxy)-4-methylpiperidin-1-yl)-2-bromo-5-methylpyrazolo[1,5-a]pyrimidin-6-yl)acetate (17.7 g, 97%). $^1$H NMR (500 MHz, CDCl3) δ 6.52 (s, 1H), 6.02 (ddt, J=17.2, 10.4, 5.2 Hz, 1H), 5.43 (dd, J=17.2, 1.6 Hz, 1H), 5.22 (dq, J=10.4, 1.5 Hz, 1H), 3.99 (dt, J=5.2, 1.6 Hz, 2H), 3.77 (s, 3H), 3.79-3.76 (m, 2H), 3.70-3.56 (m, J=7.4 Hz, 2H), 3.33 (br. s., 2H), 2.50 (s, 3H), 1.97-1.89 (m, 2H), 1.87-1.78 (m, J=9.3 Hz, 2H), 1.32 (s, 3H). LCMS (M+1)=437.20.

INTERMEDIATE 92

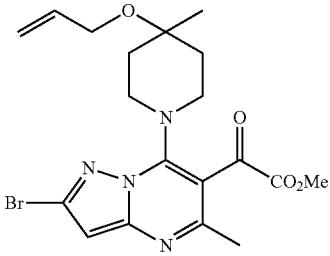 [SMILES: C=CCOC1(C)CCN(c2c(C(=O)C(=O)OC)c(C)nc3cc(Br)nn23)CC1]

Methyl 2-(7-(4-(allyloxy)-4-methylpiperidin-1-yl)-2-bromo-5-methylpyrazolo[1,5-a]pyrimidin-6-yl)-2-oxoacetate A solution of methyl 2-(7-(4-(allyloxy)-4-methylpiperidin-1-yl)-2-bromo-5-methylpyrazolo[1,5-a]pyrimidin-6-yl)acetate (17.7 g, 40.5 mmol, 1 equiv) in THF (200 mL) was cooled to −78° C. (IPA/CO$_2$). KHMDS (72 mL of a 0.91 M solution in THF, 64.9 mmol, 1.6 equiv) was added dropwise over ~2 min. Reaction turned a deep orange color. After 30 min, 3-phenyl-2-(phenylsulfonyl)-1,2-oxaziridine (15.9 g, 60.8 mmol, 1.2 equiv) was added in a single portion. The reaction significantly darkened. After 30 min, the reaction was added to saturated aqueous sodium bicarbonate and extracted with ether (×2). The combined ether extracts were dried (MgSO$_4$) and concentrated in vacuo to provide the crude product as a brown oil. This was taken up in DCM (200 mL) and Dess-Martin periodinane (20.6 g, 48.6 mmol, 1.2 equiv). After 30 min, the reaction was added to saturated aqueous sodium bicarbonate and extracted with DCM (×3). Combined DCM extracts were dried (Na$_2$SO$_4$) and concentrated in vacuo to provide the crude product. The crude product was purified via silica gel flash chromatography (0-50% EtOAc/hex) to provide methyl 2-(7-(4-(allyloxy)-4-methylpiperidin-1-yl)-2-bromo-5-methylpyrazolo[1,5-a]pyrimidin-6-yl)-2-oxoacetate (9.2 g, 50%). $^1$H NMR (500 MHz, CDCl3) δ 6.55 (s, 1H), 6.07-5.87 (m, 1H), 5.38 (dq, J=17.2, 1.7 Hz, 1H), 5.20 (dq, J=10.4, 1.6 Hz, 1H), 3.95-3.92 (m, 5H), 3.69 (d, J=12.6 Hz, 2H), 3.59-3.50 (m, 2H), 2.56 (s, 3H), 1.96-1.82 (m, 4H), 1.28 (s, 3H). LCMS (M+1)=450.95.

INTERMEDIATE 93

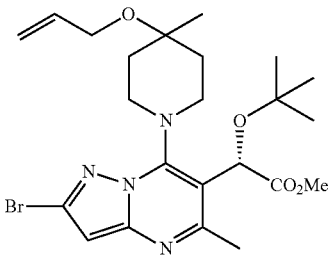 [SMILES: C=CCOC1(C)CCN(c2c([C@H](OC(C)(C)C)C(=O)OC)c(C)nc3cc(Br)nn23)CC1]

(S)-Methyl 2-(7-(4-(allyloxy)-4-methylpiperidin-1-yl)-2-bromo-5-methylpyrazolo[1,5-a]pyrimidin-6-yl)-2-(tert-butoxy)acetate A solution of methyl 2-(7-(4-(allyloxy)-4-methylpiperidin-1-yl)-2-bromo-5-methylpyrazolo[1,5-a]pyrimidin-6-yl)-2-oxoacetate (9.20 g, 20.3 mmol, 1 equiv) and (R)-1-methyl-3,3-diphenylhexahydropyrrolo[1,2-c][1,3,2]oxazaborole (12.2 mL of a 1 M solution in toluene, 12.2 mmol, 0.6 equiv) in toluene (200 mL) was cooled to −25° C. (MeCN/CO$_2$). Catecholborane (6.8 mL of a 50% solution in toluene, 28.4 mmol, 1.4 equiv) was then added and temperature was held between −15° C. and −25° C. for 18 h. At this point, more and (R)-1-methyl-3,3-diphenylhexahydropyrrolo[1,2-c][1,3,2]oxazaborole (4 mL of a 1 M solution in toluene, 4 mmol, 0.2 equiv) and catecholborane (3 mL of a 50% solution in toluene, 12.5 mmol, 0.6 equiv) were added. The reaction was then stirred a further 4 h. The reaction was then quenched with 10% aqueous K$_2$CO$_3$ (100 mL) and EtOAc (100 mL) and removed from cooling bath. After stirring 45 min, the mixture was added to water and extracted with ether (×4). The combined ether extracts were dried (MgSO$_4$) and concentrated in vacuo to provide the crude product as a yellow foam. This was taken up in DCM (50 mL) and tBuOAc (150 mL). To this solution was added 70% perchloric acid (3.7 mL, 60.9 mmol, 3 equiv) to give a cloudy orange solution. After stirring 3 h, the reaction was added cautiously to saturated aqueous sodium bicarbonate and extracted with DCM (×3). The combined DCM extracts were dried (Na$_2$SO$_4$) and concentrated in vacuo to provide the crude product. The crude product was purified via silica gel flash chromatography (0-100% EtOAc/hex) to provide (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (3.56 g, 34%) $^1$H NMR (500 MHz, CDCl$_3$) δ 6.54 (s, 1H), 6.09-5.97 (m, 1H), 5.83 (br. s., 1H), 5.48 (d, J=17.8 Hz, 1H), 5.24 (d, J=9.8 Hz, 1H), 4.50-3.00 (very broad m, 4H), 4.05-3.98 (m, 2H), 3.76 (s, 3H), 2.59 (s, 3H), 2.04-1.90 (m, 2H), 1.36 (s, 3H), 1.24 (s, 9H). LCMS (M+1)=509.09.

And recovered (S)-Methyl 2-(7-(4-(allyloxy)-4-methylpiperidin-1-yl)-2-bromo-5-methylpyrazolo[1,5-a]pyrimidin-6-yl)-2-hydroxyacetate (4.53 g, 49%). $^1$H NMR (500 MHz, CDCl$_3$) δ 6.57 (s, 1H), 6.12-5.97 (m, 1H), 5.56-5.47 (m, 2H), 5.28-5.22 (m, 1H), 4.50-3.00 (very broad m, 4H), 4.00 (dt, J=5.0, 1.6 Hz, 2H), 3.82 (s, 3H), 2.59 (s, 3H), 2.01-1.91 (m, 2H), 1.80 (d, J=11.7 Hz, 2H), 1.33 (s, 3H). LCMS (M+1)=453.00.

INTERMEDIATE 94

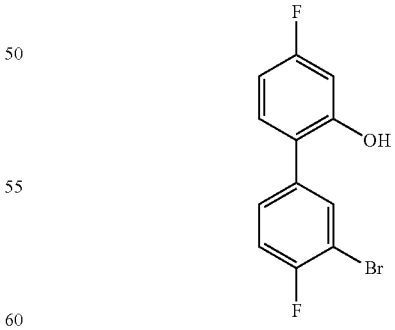

3'-Bromo-4,4'-difluoro-[1,1'-biphenyl]-2-ol

To a solution of (4-fluoro-2-hydroxyphenyl)boronic acid (500 mg, 3.21 mmol, 1 equiv), Pd(Ph$_3$P)$_4$ (371 mg, 0.321 mmol, 1 equiv) and 2-bromo-1-fluoro-4-iodobenzene (965 mg, 3.21 mmol, 1 equiv) in DMF (16 mL) was added 2 M Na₂CO₃ (4.8 ml, 9.62 mmol, 3 equiv). The reaction was heated at 85° C. for 18 h. Upon cooling to ambient temperature, the reaction was diluted with EtOAc and washed with water. The EtOAc layer was dried (Na₂SO₄) and concentrated in vacuo. The crude product was purified by flash column chromatography (0-30% EtOAc in hexane) to provide the product (0.90 g, 98%). ¹H NMR (400 MHz, CDCl₃) δ 7.66 (dd, J=6.7, 2.1 Hz, 1H), 7.37 (ddd, J=8.4, 4.6, 2.3 Hz, 1H), 7.26-7.14 (m, 2H), 6.77-6.68 (m, 2H).

INTERMEDIATE 95

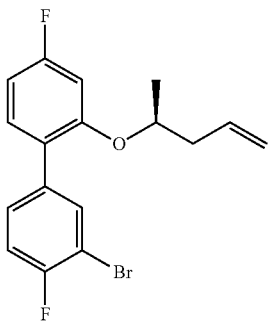 [SMILES: C=CC[C@H](C)Oc1cc(F)ccc1-c1ccc(F)c(Br)c1]

(S)-3'-Bromo-4,4'-difluoro-2-(pent-4-en-2-yloxy)-1,1'-biphenyl

To a solution of 3'-bromo-4,4'-difluoro-[1,1'-biphenyl]-2-ol (0.58 g, 2.02 mmol, 1 equiv), (R)-pent-4-en-2-ol (0.35 mg, 4.03 mmol, 2 equiv), and PPh₃ (1.06 g, 4.03 mmol, 2 equiv) in THF (7 mL) was added DEAD (1.84 ml of a 40% solution in toluene, 4.03 mmol, 2 equiv). After 18 h, the solution was concentrated on silica gel and purified by flash column chromatography (0-10% EtOAc in hexane) to provide the product (0.62 g, 87%). ¹H NMR (400 MHz, CDCl₃) δ 7.70 (dd, J=6.8, 2.3 Hz, 1H), 7.39 (ddd, J=8.5, 4.8, 2.3 Hz, 1H), 7.26-7.19 (m, 1H), 7.13 (t, J=8.4 Hz, 1H), 6.75-6.66 (m, 2H), 5.86-5.70 (m, 1H), 5.10 (d, J=12.0 Hz, 2H), 4.47-4.33 (m, 1H), 2.49-2.27 (m, 2H), 1.28 (d, J=6.3 Hz, 3H).

INTERMEDIATE 96

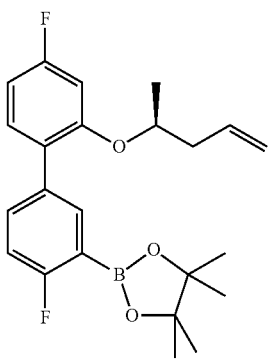 [SMILES: C=CC[C@H](C)Oc1cc(F)ccc1-c1ccc(F)c(B2OC(C)(C)C(C)(C)O2)c1]

(S)-2-(4,4'-Difluoro-2'-(pent-4-en-2-yloxy)-[1,1'-biphenyl]-3-yl)-4,4,5,5-tetramethyl-1,3,2-dioxaborolane A solution of (S)-3'-bromo-4,4'-difluoro-2-(pent-4-en-2-yloxy)-1,1'-biphenyl (0.62 g, 1.76 mmol, 1 equiv), KOAc (345 mg, 3.51 mmol, 2 equiv), 4,4,4',4',5,5,5',5'-octamethyl-2,2'-bi(1,3,2-dioxaborolane) (669 mg, 2.63 mmol, 1.5 equiv), and PdCl₂(dppf) (143 mg, 0.176 mmol, 0.1 equiv) in dioxane (7 mL) was heated to reflux for 2 h. Upon cooling to ambient temperature, the reaction was diluted with EtOAc. EtOAc washed with water, dried (Na₂SO₄), and concentrated in vacuo. The crude product was purified by flash column chromatography (0-30% EtOAc in hexane) to provide the product as a colorless film (0.42 g, 60%). ¹H NMR (400 MHz, CDCl₃) δ 7.85 (dd, J=5.8, 2.3 Hz, 1H), 7.61-7.41 (m, 1H), 7.12-7.00 (m, 1H), 6.76-6.65 (m, 2H), 5.84-5.70 (m, 1H), 5.13-5.02 (m, 2H), 4.42-4.31 (m, 1H), 2.52-2.24 (m, 2H), 1.37 (s, 8H), 1.25 (d, J=6.0 Hz, 4H).

INTERMEDIATE 97

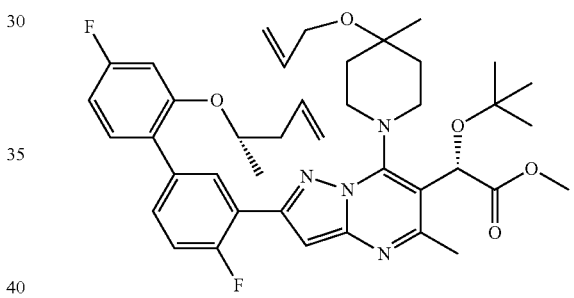

(S)-Methyl 2-(7-(4-(allyloxy)-4-methylpiperidin-1-yl)-2-(4,4'-difluoro-2'-((S)-pent-4-en-2-yloxy)-[1,1'-biphenyl]-3-yl)-5-methylpyrazolo[1,5-a]pyrimidin-6-yl)-2-(tert-butoxy)acetate A solution of (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (250 mg, 0.491 mmol, 1 equiv), PdCl₂(dppf) (40 mg, 0.049 mmol, 0.1 equiv), (S)-2-(4,4'-difluoro-2'-(pent-4-en-2-yloxy)-[1,1'-biphenyl]-3-yl)-4,4,5,5-tetramethyl-1,3,2-dioxaborolane (0.287 g, 0.716 mmol, 1.5 equiv), and 2 M K₃PO₄ (0.74 ml, 1.472 mmol, 3 equiv) in DMF (5 mL) was heated at 90° C. for 2 h. Upon cooling to ambient temperature, the reaction was diluted with EtOAc. EtOAc washed with saturated aqueous NaHCO₃, dried (MgSO₄), and concentrated in vacuo. The crude product was purified by flash column chromatography (0-100% EtOAc in hexane) to afford the product (140 mg, 41% yield) as pale yellow oil. LCMS (ESI, M+1): 703.3.

EXAMPLE 26

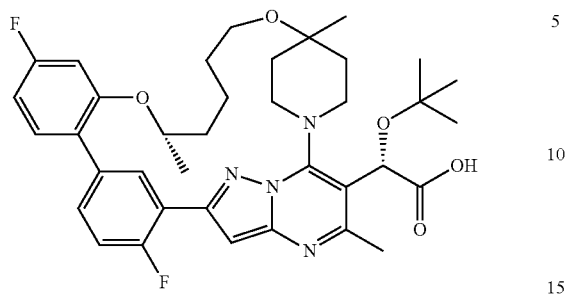

(2S)-2-(tert-Butoxy)-2-[(22S)-11,18-difluoro-4,22,28-trimethyl-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid A solution of (S)-methyl 2-(7-(4-(allyloxy)-4-methylpiperidin-1-yl)-2-(4,4'-difluoro-2'-((S)-pent-4-en-2-yloxy)-[1,1'-biphenyl]-3-yl)-5-methylpyrazolo[1,5-a]pyrimidin-6-yl)-2-(tert-butoxy)acetate (140 mg, 0.199 mmol, 1 equiv) in DCE (100 mL) was heated to 90° C. The Hoyveda Grubbs 2$^{nd}$ generation catalyst (19 mg, 0.030 mmol, 0.15 equiv) was added. After 5 h, the reaction was allowed to cool to ambient temperature and concentrated in vacuo to provide crude product (130 mg). The residue was dissolved in MeOH (5 mL) and NaBH$_4$ (36 mg, 0.963 mmol, 5 equiv) was added. After 1 h, more NaBH$_4$ (36 mg, 0.963 mmol, 5 equiv) was added. After 30 min, the reaction was diluted with EtOAc and washed with water. The EtOAc layer was dried (Na$_2$SO$_4$) and concentrated in vacuo. The crude residue was dissolved in 10:1 MeOH:water (2 mL) and LiOH (46 mg, 1.927 mmol, 10 equiv) was added. The reaction was heated at 60° C. for 2 h. Upon cooling to ambient temperature, the reaction was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min. The product was isolated (27 mg, 21%). $^1$H NMR (500 MHz, DMSO-d$_6$) δ 8.18 (d, J=7.0 Hz, 1H), 7.10-7.01 (m, 2H), 6.98 (t, J=7.6 Hz, 1H), 6.74 (d, J=11.0 Hz, 1H), 6.68 (d, J=4.3 Hz, 1H), 6.50 (t, J=7.8 Hz, 1H), 5.30 (br. s., 1H), 4.32 (d, J=5.5 Hz, 1H), 4.08 (t, J=12.4 Hz, 1H), 3.24 (t, J=11.7 Hz, 1H), 3.12 (d, J=9.5 Hz, 1H), 3.05 (br. s., 1H), 2.94 (br. s., 1H), 2.55-2.46 (m, 1H), 2.23 (s, 3H), 1.66-1.04 (m, 10H), 0.82 (s, 12H), 0.76 (d, J=5.5 Hz, 3H); LCMS (ESI, M): 662.3.

INTERMEDIATE 98

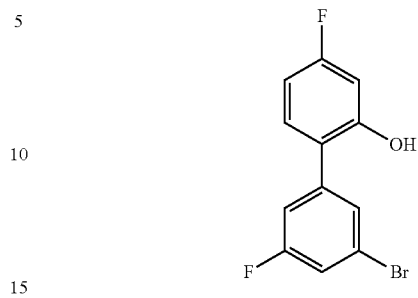

3'-Bromo-4,5'-difluoro-[1,1'-biphenyl]-2-ol

To a solution of (4-fluoro-2-hydroxyphenyl)boronic acid (500 mg, 3.21 mmol, 1 equiv), Pd(PPh$_3$)$_4$ (371 mg, 0.321 mmol, 0.1 equiv) and 1-bromo-3-fluoro-5-iodobenzene (965 mg, 3.21 mmol, 1 equiv) in DMF (16 mL) was added 2 M Na$_2$CO$_3$ (4.0 ml, 8.02 mmol, 2.5 equiv). The reaction was heated at 110° C. for 18 h. Upon cooling to ambient temperature, the reaction was diluted with EtOAc and washed with water. The EtOAc layer was dried (Na$_2$SO$_4$) and concentrated in vacuo. The crude product was purified by flash column chromatography (0-30% EtOAc in hexane) to provide the product (0.38 g, 42%). $^1$H NMR (400 MHz, CDCl$_3$) δ 7.43 (s, 1H), 7.25-7.09 (m, 3H), 6.79-6.67 (m, 2H), 5.24 (s, 1H).

INTERMEDIATE 99

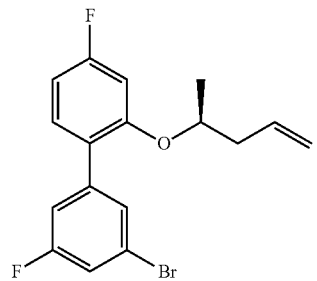 [SMILES: C=CC[C@H](C)Oc1cc(F)ccc1-c1cc(F)cc(Br)c1]

(S)-3'-Bromo-4,5'-difluoro-2-(pent-4-en-2-yloxy)-1,1'-biphenyl

To a solution of 3'-bromo-4,5'-difluoro-[1,1'-biphenyl]-2-ol (0.42 g, 1.473 mmol, 1 equiv), (R)-pent-4-en-2-ol (254 mg, 2.95 mmol, 2 equiv), and PPh$_3$ (0.77 g, 2.95 mmol, 2 equiv) in THF (5 mL) was added DEAD (1.34 ml of a 40% solution in toluene, 2.95 mmol, 2 equiv). After 18 h, the solution was concentrated on silica gel and purified by flash column chromatography (0-10% EtOAc in hexane) to provide the product (0.42 g, 81%). $^1$H NMR (400 MHz, CDCl$_3$) δ 7.44 (s, 1H), 7.26-7.16 (m, 3H), 6.75-6.67 (m, 2H), 5.85-5.70 (m, 1H), 5.18-5.04 (m, 2H), 4.41 (quin, J=5.9 Hz, 1H), 2.50-2.27 (m, 2H), 1.29 (d, J=6.0 Hz, 3H).

INTERMEDIATE 100

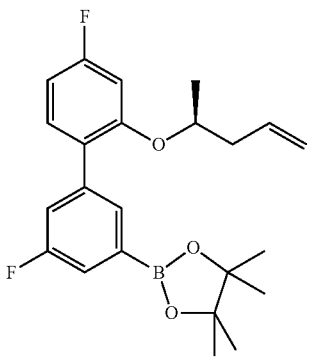 [SMILES: C=CC[C@H](C)Oc1cc(F)ccc1-c1cc(F)cc(B2OC(C)(C)C(C)(C)O2)c1]

(S)-2-(4',5-Difluoro-2'-(pent-4-en-2-yloxy)-[1,1'-biphenyl]-3-yl)-4,4,5,5-tetramethyl-1,3,2-dioxaborolane A solution of (S)-3'-bromo-4,5'-difluoro-2-(pent-4-en-2-yloxy)-1,1'-biphenyl (0.42 g, 1.189 mmol, 1 equiv), KOAc (233 mg, 2.378 mmol, 2 equiv), 4,4,4',4',5,5,5',5'-octamethyl-2,2'-bi(1,3,2-dioxaborolane) (453 mg, 2.378 mmol, 1.5 equiv), and PdCl$_2$(dppf) (97 mg, 0.119 mmol, 0.1 equiv) in dioxane (7 mL) was heated to 85° C. for 18 h. Upon cooling to ambient temperature, the reaction was diluted with EtOAc. EtOAc washed with water, dried (Na$_2$SO$_4$), and concentrated in vacuo. The crude product was purified by flash column chromatography (0-30% EtOAc in hexane) to provide the product as a colorless film (0.25 g, 62%).

INTERMEDIATE 101

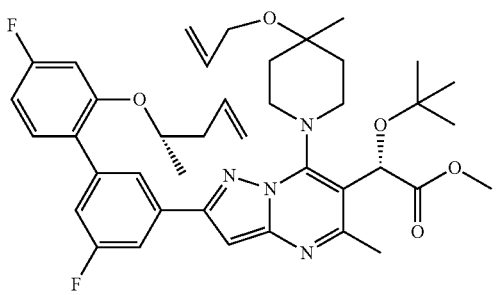 [SMILES: C=CCOC1(C)CCN(c2c([C@H](OC(C)(C)C)C(=O)OC)c(C)nc3cc(-c4cc(F)cc(-c5ccc(F)cc5O[C@@H](C)CC=C)c4)nn23)CC1]

(S)-Methyl 2-(7-(4-(allyloxy)-4-methylpiperidin-1-yl)-2-(4',5-difluoro-2'-((S)-pent-4-en-2-yloxy)-[1,1'-biphenyl]-3-yl)-5-methylpyrazolo[1,5-a]pyrimidin-6-yl)-2-(tert-butoxy)acetate A solution of (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (250 mg, 0.491 mmol, 1 equiv), PdCl$_2$(dppf) (40 mg, 0.049 mmol, 0.1 equiv), (S)-2-(4',5-difluoro-2'-(pent-4-en-2-yloxy)-[1,1'-biphenyl]-3-yl)-4,4,5,5-tetramethyl-1,3,2-dioxaborolane (0.295 g, 0.736 mmol, 1.5 equiv) and 2 M K$_3$PO$_4$ (0.74 ml, 1.472 mmol, 3 equiv) in DMF (5 mL) was heated at 90° C. for 2 h. Upon cooling to ambient temperature, the reaction was diluted with EtOAc. EtOAc washed with saturated aqueous NaHCO$_3$, dried (MgSO$_4$), and concentrated in vacuo. The crude product was purified by flash column chromatography (0-100% EtOAc in hexane) to afford the product (200 mg, 58% yield) as pale yellow oil. LCMS (ESI, M+1): 703.3.

EXAMPLE 27

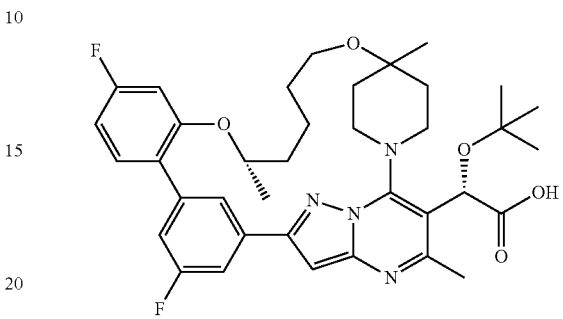

(2S)-2-(tert-Butoxy)-2-[(22S)-12,18-difluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid A solution of (S)-methyl 2-(7-(4-(allyloxy)-4-methylpiperidin-1-yl)-2-(4',5-difluoro-2'-((S)-pent-4-en-2-yloxy)-[1,1'-biphenyl]-3-yl)-5-methylpyrazolo[1,5-a]pyrimidin-6-yl)-2-(tert-butoxy)acetate (200 mg, 0.285 mmol, 1 equiv) in DCE (140 mL) was heated to 90° C. The Hoyveda Grubbs 2$^{nd}$ generation catalyst (4 mg, 0.006 mmol, 0.05 equiv) was added. The pale green brown solution was stirred for 2 h and more Hoyveda Grubbs 2$^{nd}$ generation catalyst (27 mg, 0.043 mmol, 0.15 equiv) was added. After 5 h, the reaction was allowed to cool to ambient temperature and concentrated in vacuo. The residue was dissolved in MeOH (5 mL) was added 10% Pd/C (24 mg, 0.022 mmol, 0.1 equiv). The reaction was put under a balloon of H$_2$ and stirred 2 h. Upon completion, the reaction was filtered through Celite. To the filtrate was added LiOH (53 mg, 2.223 mmol, 10 equiv). The reaction was heated at 60° C. for 2 h. Upon cooling to ambient temperature, the reaction was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-90% B over 15 minutes, then a 5-minute hold at 100% B; Flow: 20 mL/min. The product was isolated (50 mg, 34%). $^1$H NMR (500 MHz, DMSO-d$_6$) δ 8.28 (s, 1H), 7.81 (d, J=9.8 Hz, 1H), 7.36 (t, J=7.6 Hz, 1H), 7.21-7.09 (m, 3H), 6.83 (t, J=8.2 Hz, 1H), 5.59 (br. s., 1H), 4.69 (d, J=5.5 Hz, 1H), 4.43 (t, J=12.1 Hz, 1H), 3.41 (br. s., 5H), 1.97-1.82 (m, 3H), 1.67 (d, J=10.1 Hz, 4H), 1.56-1.40 (m, 2H); LCMS (ESI, M+1): 663.30.

INTERMEDIATE 102

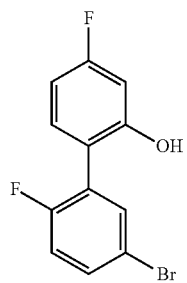

5'-Bromo-2',4-difluoro-[1,1'-biphenyl]-2-ol

To a solution of (4-fluoro-2-hydroxyphenyl)boronic acid (500 mg, 3.21 mmol, 1 equiv), Pd(PPh$_3$)$_4$ (371 mg, 0.321 mmol, 0.1 equiv) and 1-bromo-4-fluoro-3-iodobenzene (965 mg, 3.21 mmol, 1 equiv) in DMF (16 mL) was added 2 M Na$_2$CO$_3$ (4.8 ml, 9.62 mmol, 3 equiv). The reaction was heated at 85° C. for 18 h. Upon cooling to ambient temperature, the reaction was diluted with EtOAc and washed with water. The EtOAc layer was dried (Na$_2$SO$_4$) and concentrated in vacuo. The crude product was purified by flash column chromatography (0-30% EtOAc in hexane) to provide the product (0.90 g, 98%). $^1$H NMR (400 MHz, CDCl$_3$) δ 7.54-7.48 (m, 2H), 7.19 (dd, J=8.2, 6.7 Hz, 1H), 7.10 (t, J=9.3 Hz, 1H), 6.79-6.70 (m, 2H), 5.13 (s, 1H).

INTERMEDIATE 103

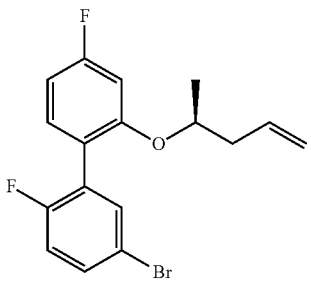 [SMILES: C=CC[C@H](C)Oc1cc(F)ccc1-c1cc(Br)ccc1F]

(S)-5'-Bromo-2',4-difluoro-2-(pent-4-en-2-yloxy)-1,1'-biphenyl

To a solution of 5'-bromo-2',4-difluoro-[1,1'-biphenyl]-2-ol (0.60 g, 2.105 mmol, 1 equiv), (R)-pent-4-en-2-ol (363 mg, 4.21 mmol, 2 equiv), and PPh$_3$ (1.1 g, 4.21 mmol, 2 equiv) in THF (7 mL) was added DEAD (1.9 ml of a 40% solution in toluene, 4.21 mmol, 2 equiv). After 18 h, the solution was concentrated on silica gel and purified by flash column chromatography (0-10% EtOAc in hexane) to provide the product (0.68 g, 91%). $^1$H NMR (400 MHz, CDCl$_3$) δ 7.46 (dd, J=6.3, 2.5 Hz, 1H), 7.42 (ddd, J=8.7, 4.3, 2.5 Hz, 1H), 7.34 (br. s., 1H), 7.20 (t, J=7.5 Hz, 1H), 7.00 (t, J=9.0 Hz, 1H), 6.76-6.65 (m, 2H), 5.81-5.66 (m, 1H), 5.11-5.01 (m, 2H), 4.45-4.32 (m, 1H), 2.48-2.23 (m, 2H), 1.26 (d, J=6.0 Hz, 3H).

INTERMEDIATE 104

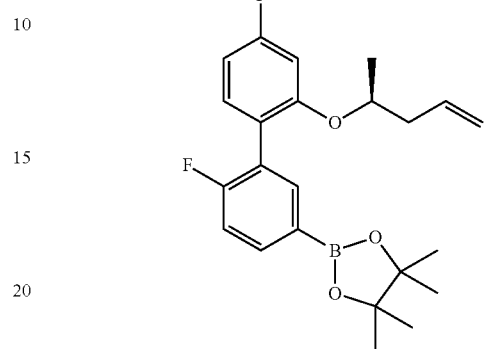

(S)-2-(4',6-Difluoro-2'-(pent-4-en-2-yloxy)-[1,1'-biphenyl]-3-yl)-4,4,5,5-tetramethyl-1,3,2-dioxaborolane A solution of (S)-5'-bromo-2',4-difluoro-2-(pent-4-en-2-yloxy)-1,1'-biphenyl (0.68 g, 1.93 mmol, 1 equiv), KOAc (378 mg, 3.85 mmol, 2 equiv), 4,4,4',4',5,5,5',5'-octamethyl-2,2'-bi(1,3,2-dioxaborolane) (733 mg, 2.89 mmol, 1.5 equiv), and PdCl$_2$(dppf) (157 mg, 0.193 mmol, 0.1 equiv) in dioxane (8 mL) was heated to 85° C. for 18 h. Upon cooling to ambient temperature, the reaction was diluted with EtOAc. EtOAc washed with water, dried (Na$_2$SO$_4$), and concentrated in vacuo. The crude product was purified by flash column chromatography (0-30% EtOAc in hexane) to provide the product as a colorless film (0.50 g, 65%). LCMS (ESI, M+1): 401.25.

INTERMEDIATE 105

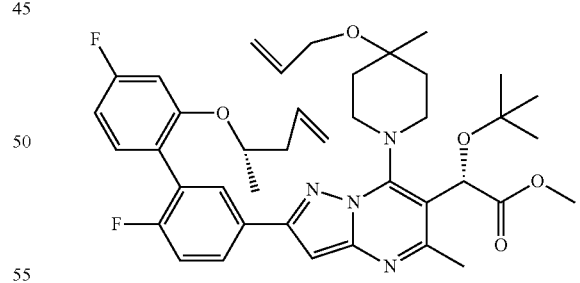

(S)-Methyl 2-(7-(4-(allyloxy)-4-methylpiperidin-1-yl)-2-(4',6-difluoro-2'-((S)-pent-4-en-2-yloxy)-[1,1'-biphenyl]-3-yl)-5-methylpyrazolo[1,5-a]pyrimidin-6-yl)-2-(tert-butoxy)acetate A solution of (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (250 mg, 0.491 mmol, 1 equiv), PdCl$_2$(dppf) (40 mg, 0.049 mmol, 0.1 equiv), (S)-2-(4',6-difluoro-2'-(pent-4-en-2-yloxy)-[1,1'-biphenyl]-3-yl)-4,4,5, 5-tetramethyl-1,3,2-dioxaborolane (0.50 g, 1.23 mmol, 2.5 equiv), and 2 M K₃PO₄ (0.74 ml, 1.472 mmol, 3 equiv) in DMF (5 mL) was heated at 90° C. for 2 h. Upon cooling to ambient temperature, the reaction was diluted with EtOAc. EtOAc washed with saturated aqueous NaHCO₃, dried (MgSO₄), and concentrated in vacuo. The crude product was purified by flash column chromatography (0-100% EtOAc in hexane) to afford (S)-methyl 2-(7-(4-(allyloxy)-4-methylpiperidin-1-yl)-2-(4',6-difluoro-2'-((S)-pent-4-en-2-yloxy)-[1,1'-biphenyl]-3-yl)-5-methylpyrazolo[1,5-a]pyrimidin-6-yl)-2-(tert-butoxy)acetate (210 mg, 61% yield) as pale yellow oil. LCMS (ESI, M+1): 703.3.

EXAMPLE 28

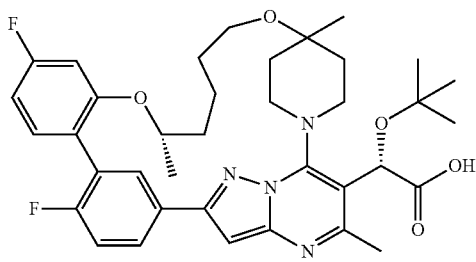 [SMILES: Cc1nc2cc3nn2c(c1[C@H](OC(C)(C)C)C(=O)O)N1CCC(C)(CC1)OCCCC[C@H](C)Oc1cc(F)ccc1-c1cc-3ccc1F]

(2S)-2-(tert-Butoxy)-2-[(22S)-13,18-difluoro-4,22,28-trimethyl-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid A solution of (S)-methyl 2-(7-(4-(allyloxy)-4-methylpiperidin-1-yl)-2-(4',6-difluoro-2'-((S)-pent-4-en-2-yloxy)-[1,1'-biphenyl]-3-yl)-5-methylpyrazolo[1,5-a]pyrimidin-6-yl)-2-(tert-butoxy)acetate (210 mg, 0.299 mmol, 1 equiv) in DCE (150 mL) was heated to 90° C. The Hoyveda Grubbs 2$^{nd}$ generation catalyst (28 mg, 0.045 mmol, 0.15 equiv) was added. After 5 h, the reaction was allowed to cool to ambient temperature and concentrated in vacuo to provide crude product (150 mg). The residue was dissolved in MeOH (5 mL) was added 10% Pd/C (24 mg, 0.022 mmol, 0.1 equiv). The reaction was put under a balloon of H₂ and stirred 2 h. Upon completion, the reaction was filtered through Celite. To the filtrate was added LiOH (53 mg, 2.223 mmol, 10 equiv). The reaction was heated at 60° C. for 2 h. Upon cooling to ambient temperature, the reaction was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. The product was isolated (35 mg, 24%). ¹H NMR (500 MHz, DMSO-d₆) δ 8.18 (d, J=6.1 Hz, 1H), 7.92 (br. s., 1H), 7.33 (t, J=9.0 Hz, 1H), 7.24 (t, J=6.9 Hz, 1H), 7.08 (d, J=11.6 Hz, 1H), 7.00 (s, 1H), 6.78 (t, J=7.5 Hz, 1H), 5.66 (br. s., 1H), 4.61 (br. s., 1H), 4.42 (t, J=11.6 Hz, 1H), 3.49 (t, J=11.7 Hz, 1H), 3.33 (br. s., 1H), 3.23 (d, J=7.6 Hz, 2H), 2.70 (d, J=11.9 Hz, 1H), 2.47 (s, 3H), 1.88 (d, J=13.4 Hz, 1H), 1.79 (d, J=13.1 Hz, 2H), 1.57 (d, J=12.2 Hz, 5H), 1.35 (br. s., 2H), 1.11 (s, 9H), 1.04 (d, J=5.8 Hz, 3H);

The following compounds could be synthesized by following the procedures described for the above examples 1-32.

EXAMPLE 29

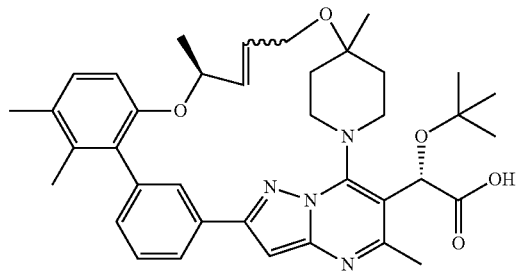 [SMILES: Cc1ccc2c(c1C)-c1cccc(c1)-c1cc3nc(C)c([C@H](OC(C)(C)C)C(=O)O)c(n3n1)N1CCC(C)(CC1)OCC=C[C@H](C)O2]

(2S)-2-(tert-Butoxy)-2-[(22S)-4,16,17,22,27-pentamethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid

EXAMPLE 30

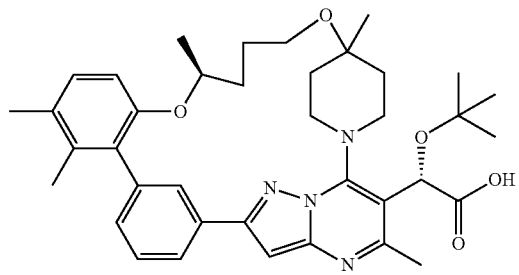 [SMILES: Cc1ccc2c(c1C)-c1cccc(c1)-c1cc3nc(C)c([C@H](OC(C)(C)C)C(=O)O)c(n3n1)N1CCC(C)(CC1)OCCC[C@H](C)O2]

(2S)-2-(tert-Butoxy)-2-[(22S)-4,16,17,22,27-pentamethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid

EXAMPLE 31

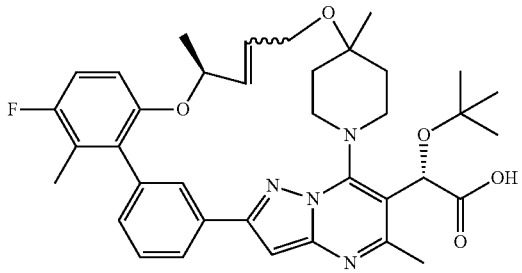 [SMILES: Cc1nc2cc3nn2c(c1[C@H](OC(C)(C)C)C(=O)O)N1CCC(C)(CC1)OCC=C[C@H](C)Oc1ccc(F)c(C)c1-c1cccc-3c1]

103

(2S)-2-(tert-Butoxy)-2-[(22S)-17-fluoro-4,16,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid

EXAMPLE 32

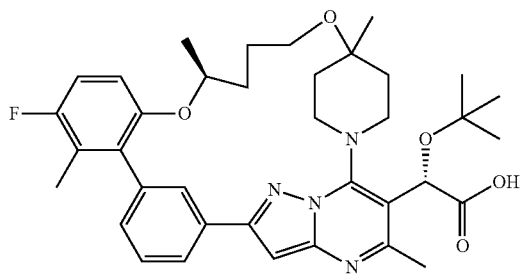 [SMILES: Cc1nc2cc3nn2c(c1[C@H](OC(C)(C)C)C(=O)O)N1CCC(C)(CC1)OCCC[C@H](C)Oc1ccc(F)c(C)c1-c1cccc-3c1]

(2S)-2-(tert-Butoxy)-2-[(22S)-17-fluoro-4,16,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid

EXAMPLE 33

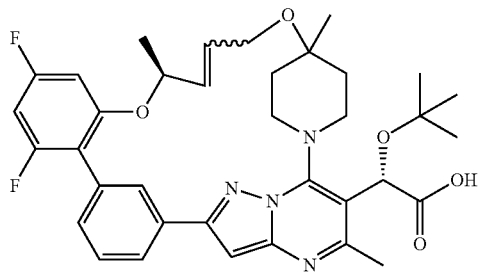 [SMILES: Cc1nc2cc3nn2c(c1[C@H](OC(C)(C)C)C(=O)O)N1CCC(C)(CC1)OCC=C[C@H](C)Oc1cc(F)cc(F)c1-c1cccc-3c1]

(2S)-2-(tert-Butoxy)-2-[(22S)-16,18-difluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid

EXAMPLE 34

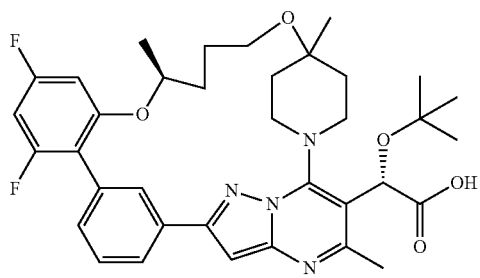 [SMILES: Cc1nc2cc3nn2c(c1[C@H](OC(C)(C)C)C(=O)O)N1CCC(C)(CC1)OCCC[C@H](C)Oc1cc(F)cc(F)c1-c1cccc-3c1]

104

(2S)-2-(tert-Butoxy)-2-[(22S)-16,18-difluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid

EXAMPLE 35

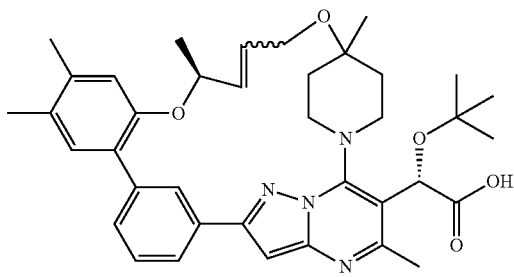 [SMILES: Cc1cc2c(cc1C)-c1cccc(c1)-c1cc3nc(C)c([C@H](OC(C)(C)C)C(=O)O)c(n3n1)N1CCC(C)(CC1)OCC=C[C@H](C)O2]

(2S)-2-(tert-Butoxy)-2-[(22S)-4,17,18,22,27-pentamethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid

EXAMPLE 36

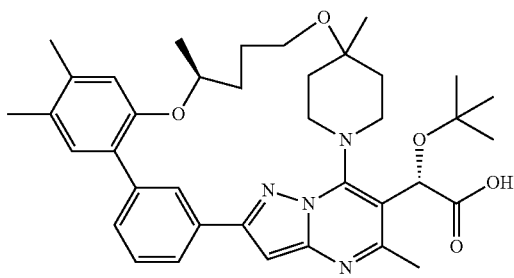 [SMILES: Cc1cc2c(cc1C)-c1cccc(c1)-c1cc3nc(C)c([C@H](OC(C)(C)C)C(=O)O)c(n3n1)N1CCC(C)(CC1)OCCC[C@H](C)O2]

(2S)-2-(tert-Butoxy)-2-[(22S)-4,17,18,22,27-pentamethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid

EXAMPLE 37

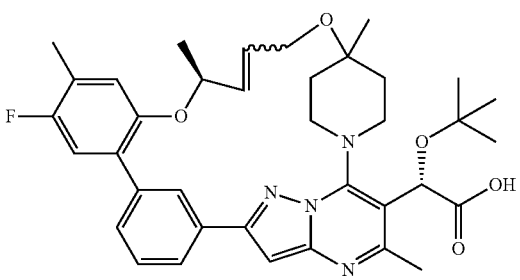 [SMILES: Cc1cc2c(cc1F)-c1cccc(c1)-c1cc3nc(C)c([C@H](OC(C)(C)C)C(=O)O)c(n3n1)N1CCC(C)(CC1)OCC=C[C@H](C)O2]

(2S)-2-(tert-Butoxy)-2-[(22S)-17-fluoro-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid

EXAMPLE 38

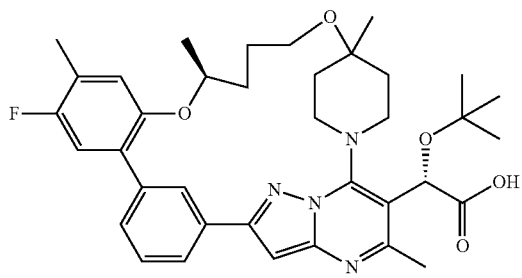 [SMILES: Cc1cc2c(cc1F)-c1cccc(c1)-c1cc3nc(C)c([C@H](OC(C)(C)C)C(=O)O)c(n3n1)N1CCC(C)(CC1)OCCC[C@H](C)O2]

(2S)-2-(tert-Butoxy)-2-[(22S)-17-fluoro-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid

EXAMPLE 39

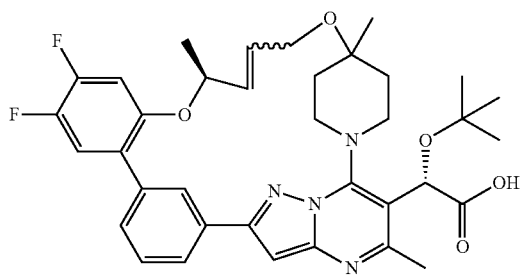 [SMILES: Cc1nc2cc3nn2c(c1[C@H](OC(C)(C)C)C(=O)O)N1CCC(C)(CC1)OCC=C[C@H](C)Oc1cc(F)c(F)cc1-c1cccc-3c1]

(2S)-2-(tert-Butoxy)-2-[(22S)-17,18-difluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid

EXAMPLE 40

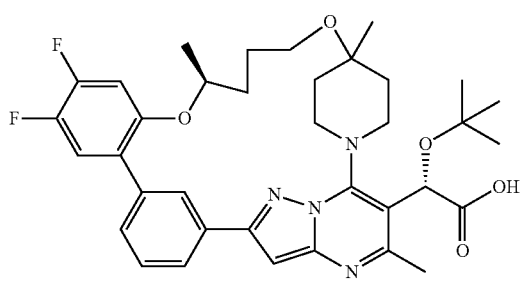 [SMILES: Cc1nc2cc3nn2c(c1[C@H](OC(C)(C)C)C(=O)O)N1CCC(C)(CC1)OCCC[C@H](C)Oc1cc(F)c(F)cc1-c1cccc-3c1]

(2S)-2-(tert-Butoxy)-2-[(22S)-17,18-difluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid

EXAMPLE 41

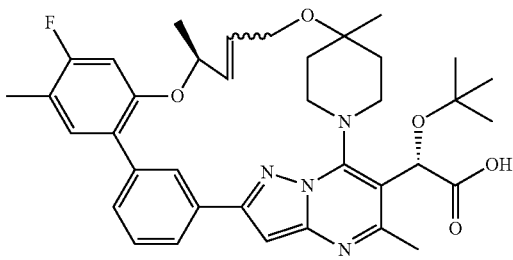 [SMILES: Cc1cc2c(cc1F)O[C@@H](C)C=CCOC1(C)CCN(CC1)c1c([C@H](OC(C)(C)C)C(=O)O)c(C)nc3cc(nn13)-c1cccc-2c1]

(2S)-2-(tert-Butoxy)-2-[(22S)-18-fluoro-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid

EXAMPLE 42

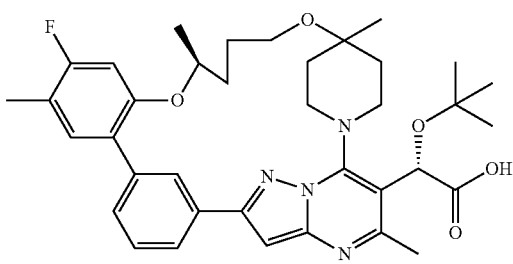 [SMILES: Cc1cc2c(cc1F)O[C@@H](C)CCCOC1(C)CCN(CC1)c1c([C@H](OC(C)(C)C)C(=O)O)c(C)nc3cc(nn13)-c1cccc-2c1]

(2S)-2-(tert-Butoxy)-2-[(22S)-18-fluoro-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid

EXAMPLE 43

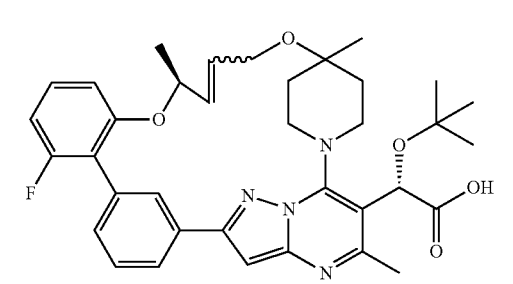 [SMILES: Cc1nc2cc3nn2c(c1[C@H](OC(C)(C)C)C(=O)O)N1CCC(C)(CC1)OCC=C[C@H](C)Oc1cccc(F)c1-c1cccc-3c1]

(2S)-2-(tert-Butoxy)-2-[(22S)-16-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid

EXAMPLE 44

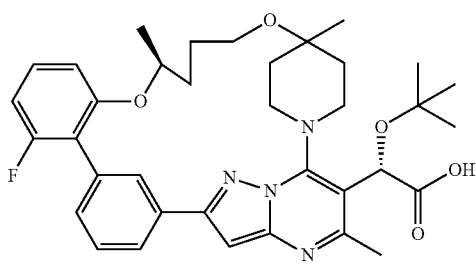 [SMILES: Cc1nc2cc3nn2c(c1[C@H](OC(C)(C)C)C(=O)O)N1CCC(C)(CC1)OCCC[C@H](C)Oc1cccc(F)c1-c1cccc-3c1]

(2S)-2-(tert-Butoxy)-2-[(22S)-16-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid

EXAMPLE 45

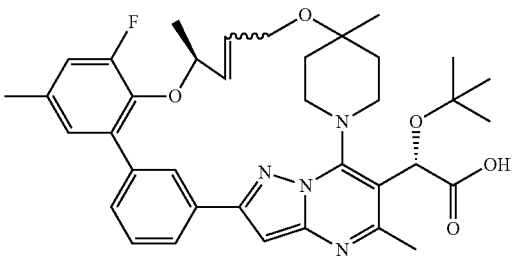 [SMILES: Cc1cc(F)c2c(c1)-c1cccc(c1)-c1cc3nc(C)c([C@H](OC(C)(C)C)C(=O)O)c(n3n1)N1CCC(C)(CC1)OCC=C[C@H](C)O2]

(2S)-2-(tert-Butoxy)-2-[(22S)-19-fluoro-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid

EXAMPLE 46

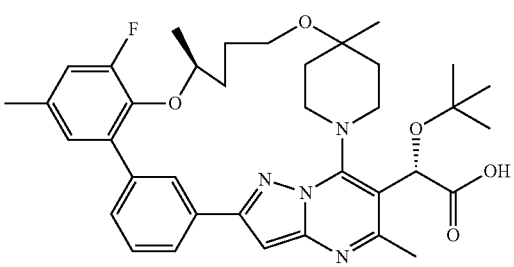 [SMILES: Cc1cc(F)c2c(c1)-c1cccc(c1)-c1cc3nc(C)c([C@H](OC(C)(C)C)C(=O)O)c(n3n1)N1CCC(C)(CC1)OCCC[C@H](C)O2]

(2S)-2-(tert-Butoxy)-2-[(22S)-19-fluoro-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid

EXAMPLE 47

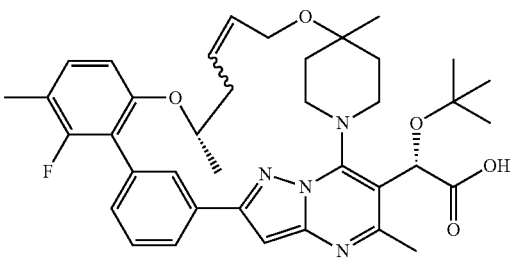 [SMILES: Cc1ccc2c(c1F)-c1cccc(c1)-c1cc3nc(C)c([C@H](OC(C)(C)C)C(=O)O)c(n3n1)N1CCC(C)(CC1)OCC=CC[C@H](C)O2]

(2S)-2-(tert-Butoxy)-2-[(22S)-16-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid

EXAMPLE 48

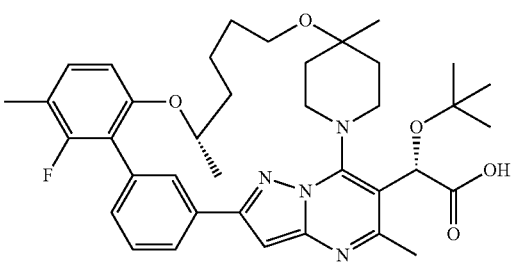 [SMILES: Cc1ccc2c(c1F)-c1cccc(c1)-c1cc3nc(C)c([C@H](OC(C)(C)C)C(=O)O)c(n3n1)N1CCC(C)(CC1)OCCCC[C@H](C)O2]

(2S)-2-(tert-Butoxy)-2-[(22S)-16-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid

EXAMPLE 49

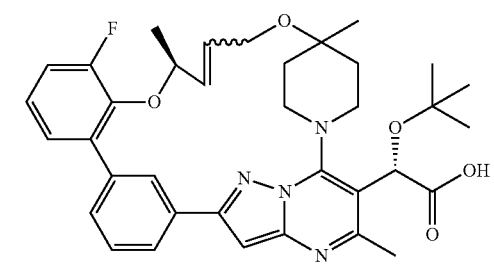 [SMILES: Cc1nc2cc3nn2c(c1[C@H](OC(C)(C)C)C(=O)O)N1CCC(C)(CC1)OCC=C[C@H](C)Oc1c(F)cccc1-c1cccc-3c1]

(2S)-2-(tert-Butoxy)-2-[(22S)-19-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid

EXAMPLE 50

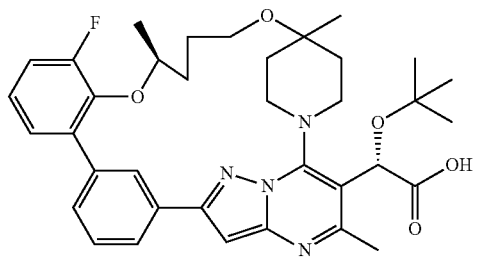 [SMILES: Cc1nc2cc3nn2c(c1[C@H](OC(C)(C)C)C(=O)O)N1CCC(C)(CC1)OCCC[C@H](C)Oc1c(F)cccc1-c1cccc-3c1]

(2S)-2-(tert-Butoxy)-2-[(22S)-19-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid

EXAMPLE 51

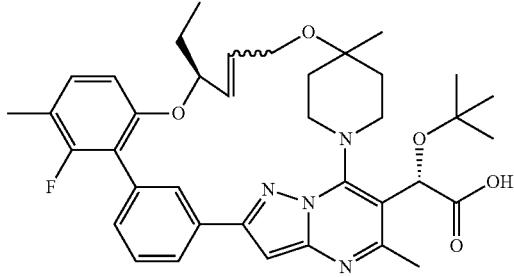 [SMILES: CC[C@H]1C=CCOC2(C)CCN(CC2)c2c([C@H](OC(C)(C)C)C(=O)O)c(C)nc3cc(nn23)-c2cccc(c2)-c2c(ccc(C)c2F)O1]

(2S)-2-(tert-Butoxy)-2-[(22S)-19-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid

EXAMPLE 52

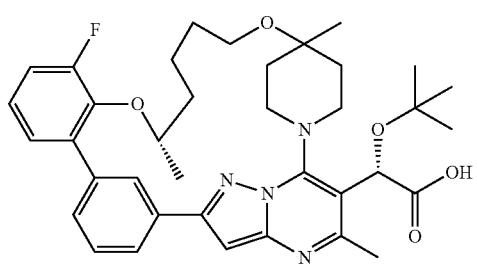 [SMILES: Cc1nc2cc3nn2c(c1[C@H](OC(C)(C)C)C(=O)O)N1CCC(C)(CC1)OCCCC[C@H](C)Oc1c(F)cccc1-c1cccc-3c1]

(2S)-2-(tert-Butoxy)-2-[(22S)-19-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid

EXAMPLE 53

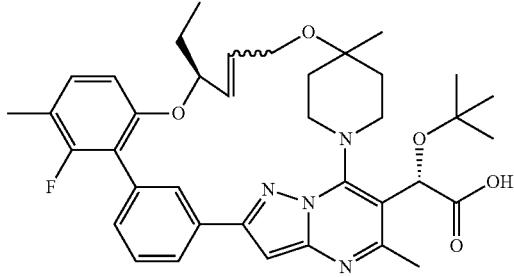 [SMILES: CC[C@H]1C=CCOC2(C)CCN(CC2)c2c([C@H](OC(C)(C)C)C(=O)O)c(C)nc3cc(nn23)-c2cccc(c2)-c2c(ccc(C)c2F)O1]

(2S)-2-(tert-Butoxy)-2-[(22S)-22-ethyl-16-fluoro-4,17,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid

EXAMPLE 54

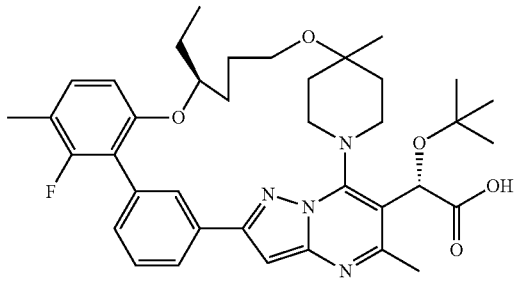 [SMILES: CC[C@H]1CCCOC2(C)CCN(CC2)c2c([C@H](OC(C)(C)C)C(=O)O)c(C)nc3cc(nn23)-c2cccc(c2)-c2c(ccc(C)c2F)O1]

(2S)-2-(tert-Butoxy)-2-[(22S)-22-ethyl-16-fluoro-4,17,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound or salt selected from the group consisting of
(2S)-2-(tert-Butoxy)-2-[(22S)-4,22,28-trimethyl-17-(trifluoromethyl)-21,27-dioxa-1,5,7,8-tetraazahexacyclo

[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17,18-difluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-16,18-difluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S,24E)-16-fluoro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid;

(2S)-2-(tert-Butoxy)-2-[(22S)-16-fluoro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-ethyl-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid;

(2S)-2-(tert-Butoxy)-2-[(22S)-17-ethyl-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-methoxy-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(23E)-18-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-18-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S,23E)-16-fluoro-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-16-fluoro-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S,23E)-17-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-17-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S,23E)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S,23E)-16-fluoro-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-16-fluoro-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S,25Z)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,25-undecaen-3-yl]acetic acid;

(2S)-2-(tert-Butoxy)-2-[(22S)-4,17,22,28-tetramethyl-21-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid;

(2S)-2-(tert-Butoxy)-2-[(22S)-4,17,22,28-tetramethyl-21-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-cyano-4,22,28-trimethyl-21-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid;

(2S)-2-(tert-Butoxy)-2-[(22S)-17-cyano-4,22,28-trimethyl-21-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-butoxy)-2-[(22S)-17-carbamoyl-4,22,28-trimethyl-21-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-[(3,3-dimethylbutyl)carbamoyl]-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-11,18-difluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-12,18-difluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-13,18-difluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-4,16,17,22,27-pentamethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-4,16,17,22,27-pentamethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S)-17-fluoro-4,16,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-17-fluoro-4,16,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S)-16,18-difluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-16,18-difluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S)-4,17,18,22,27-pentamethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-4,17,18,22,27-pentamethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S)-17-fluoro-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-17-fluoro-4,18,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S)-17,18-difluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-17,18-difluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S)-18-fluoro-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-18-fluoro-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S)-16-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-16-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S)-19-fluoro-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-19-fluoro-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S)-16-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid;

(2S)-2-(tert-Butoxy)-2-[(22S)-16-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-19-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid;

(2S)-2-(tert-Butoxy)-2-[(22S)-19-fluoro-4,22,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid;

(2S)-2-(tert-Butoxy)-2-[(22S)-19-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid;

(2S)-2-(tert-Butoxy)-2-[(22S)-19-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-22-ethyl-16-fluoro-4,17,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid; and (2S)-2-(tert-Butoxy)-2-[(22S)-22-ethyl-16-fluoro-4,17,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid or a pharmaceutically acceptable salt thereof.

2. A composition comprising a therapeutic amount of a compound or salt of claim 1 and a pharmaceutically acceptable carrier.

3. A method for treating HIV infection comprising administering of a compound of claim 1, or a pharmaceutically acceptable salt thereof, to a patient in need thereof.

4. The method of claim 3 further comprising administering at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *